US009376663B2

(12) United States Patent
Littman et al.

(10) Patent No.: US 9,376,663 B2
(45) Date of Patent: Jun. 28, 2016

(54) GPR15-MEDIATED HOMING AND USES THEREOF

(71) Applicants: Dan R. Littman, New York, NY (US); Sang-Won Kim, New York, NY (US)

(72) Inventors: Dan R. Littman, New York, NY (US); Sang-Won Kim, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/243,290

(22) Filed: Apr. 2, 2014

(65) Prior Publication Data

US 2014/0294793 A1 Oct. 2, 2014

Related U.S. Application Data

(60) Provisional application No. 61/807,484, filed on Apr. 2, 2013.

(51) Int. Cl.
*C12N 5/0783* (2010.01)
*A61K 35/00* (2006.01)
*A01K 67/027* (2006.01)

(52) U.S. Cl.
CPC .......... *C12N 5/0636* (2013.01); *A01K 67/0271* (2013.01); *C12N 5/0637* (2013.01); *A61K 35/00* (2013.01)

(58) Field of Classification Search
CPC ..... C12N 5/0636; C12N 5/0637; A61K 35/17
See application file for complete search history.

(56) References Cited

U.S. PATENT DOCUMENTS

| | | | |
|---|---|---|---|
| 6,281,012 B1 | 8/2001 | McIntosh et al. | |
| 8,241,621 B2 | 8/2012 | Ichim | |
| 2006/0062763 A1 | 3/2006 | Godfrey et al. | |
| 2006/0115899 A1 | 6/2006 | Buckner et al. | |
| 2006/0233751 A1 | 10/2006 | Bluestone et al. | |
| 2006/0263340 A1 | 11/2006 | Andrian et al. | |
| 2010/0183575 A1* | 7/2010 | Noelle | 424/93.71 |
| 2011/0268752 A1 | 11/2011 | Riley et al. | |
| 2011/0300119 A1 | 12/2011 | Tran et al. | |

OTHER PUBLICATIONS

Xiao et al., J Immunol 2008; 181:2277-2284.*
Wang et al., J Immunol. Sep. 15, 2009;183(6):4119-4126.*
Wu et al. PLoS One. Dec. 17, 2010;5(12):e15150. doi: 10.1371/journal.pone.0015150.*
Kang et al., J. Immunology 179:3724-3733.*
Fleissner et al., Eur J Microbiol Immunol. Sep. 2011;1(3):208-214.*
Maloy et al., "Intestinal homeostasis and its breakdown in inflammatory bowel disease", Nature, 2011, 474:298-306.
Agace et al., "T-cell recruitment to the intestinal mucosa", Trends in Immunology, 2008, 29:514-522.
Mora et al., "Vitamin effects on the immune system: vitamins A and D take centre stage", Nat Rev Immunol, 2008, 8:685-698.
Sigmundsdottir et al., "Environmental cues, dendritic cells and the programming of tissue-selective lymphocyte trafficking", Nat Immunol, 2008, 9:981-987.
Iwata et al., "Retinoic acid imprints gut-homing specificity on T cells", Immunity 21, 2004, 527-538.
Mora et al., "Generation of gut-homing IgA-secreting B cells by intestinal dendritic cells", Science 314, 2006, 1157-1160.
Mucida et al., "Reciprocal TH17 and regulatory T cell differentiation mediated by retinoic acid", Science 317, 2007, 256-260.
Benson et al. "All-trans retinoic acid mediates enhanced T reg cell growth, differentiation, and gut homing in the face of high levels of co-stimulation", J Exp Med 204, 2007, 1765-1774.
Coombes et al., "A functionally specialized population of mucosal CD103+ DCs induces Foxp3+ regulatory T cells via a TGF-beta and retinoic acid-dependent mechanism", J Exp Med 204, 2007, 1757-1764.
Sun et al., "Small intestine lamina propria dendritic cells promote de novo generation of Foxp3 T reg cells via retinoic acid", J Exp Med 204, 2007, 1775-1785.
Bilate et al. "Induced CD4(+)Foxp3(+) Regulatory T Cells in Immune Tolerance", Annu Rev Immunol 30, 2012, 733-758.
Deng et al. "Expression cloning of new receptors used by simian and human immunodeficiency viruses", Nature 388, 1997, 296-300.
Farzan et al., "Two orphan seven-transmembrane segment receptors which are expressed in CD4-positive cells support simian immunodeficiency virus infection", J Exp Med 186, 1997, 405-411.
Yoshinaga et al., "Perturbation of transforming growth factor (TGF)-ss1 association with latent TGF-beta binding protein yields inflammation and tumors", Proc Natl Acad Sci USA 105, 2008, 18758-18763.
Maloy et al., "CD4+CD25+ T(R) cells suppress innate immune pathology through cytokine-dependent mechanisms", J Exp Med 197, 2003, 111-119.
Garrett et al., "Communicable Ulcerative Colitis Induced by T-bet Deficiency in the Innate Immune System", Cell 131, 2007, 33-45.
Rivera-Nieves et al., "L-selectin, alpha 4 beta 1, and alpha 4 beta 7 integrins participate in CD4+ T cell recruitment to chronically inflamed small intestine", J Immunol 174, 2005, 2343-2352.
Cassani et al., "Gut-tropic T cells that express integrin α4β7 and CCR9 are required for induction of oral immune tolerance in mice", Gastroenterology 141, 2011, 2109-2118.
Riley et al., "Human T Regulatory Cells as Therapeutic Agents: Take a Billion or So of These and Call Me in the Morning", Immunity, 2009, 30(5): 656-665.
Tang et al., "CD4+Foxp3+ regulatory T cell therapy in transplantation", Journal of Molecular Cell Biology, 2012, 4, 11-21.
Bluestone et al., "Regulatory T-cell therapy: is it ready for the clinic?", Nature Reviews, Immunology, vol. 5, 2005.

(Continued)

*Primary Examiner* — Daniel C Gamett

(74) *Attorney, Agent, or Firm* — Klauber & Jackson LLC

(57) ABSTRACT

The present invention is directed to in vitro methods for promoting expression of G-protein coupled receptor 15 (GPR15) on T cells, GPR15+ enriched populations of T cells generated using these methods and compositions thereof, as well as methods of using these T cell populations for therapeutic purposes.

27 Claims, 38 Drawing Sheets

(56) References Cited

OTHER PUBLICATIONS

Schließer et al., "Tregs: application for solid-organ transplantation", 2010, 17:1.

Safinia et al., "Adoptive regulatory T cell therapy: challenges in clinical transplantation", Curr Opin Organ Transplant, 2010, 15:427-434.

Strainic et al., "Absence of signaling into CD4+ cells via C3aR and C5aR enables autoinductive TGF-••1 signaling and induction of Foxp3+ regulatory T cells", Nature Immunology, 2013, 14, 162-172.

Johansson-Lindbom et al., "Generation of gut-homing T cells and their localization to the small intestinal mucosa", Immunological Reviews, 2007, 215:226-242.

Di Ianni et al., "Tregs prevent GVHD and promote immune reconstitution in HLA-haploidentical transplantation", Blood, 2011, 117:3921-3928.

Mora et al., "Selective imprinting of gut-homing T cells by Peyer's patch dendritic cells", Nature, 2003, 424.

McDermott et al., "Impaired intestinal localization of mesenteric lymphoblasts associated with vitamin A deficiency and protein-calorie malnutrition", Immunology, 1982, 45:1-5.

Wang et al., "Retinoic Acid Determines the Precise Tissue Tropism of Inflammatory Th17 Cells in the Intestine", The Journal of Immunology, 2010, 184: 5519-5526.

Kim et al., "GPR15 controls localization of regulatory T cells to the large intestine", New York University School of Medicine.

Kim et al., GPR15-mediated homing controls immune homeostasis in the large intestine mucosa, Science, 2013, 340:1456-1459.

Golovina et al., "CD28 Costimulation Is Essential for Human T Regulatory Expansion and Function1", J Immunol, 2008, 181:2855-2868.

Basu et al., "Cutting Edge: Foxp3-Mediated Induction of Pim 2 Allows Human T Regulatory Cells to Preferentially Expand in Rapamycin1", J Immunol, 2008, 180:5794-5798.

Zhao et al., "Transcriptomic assay of CD8+ T cells in treatment-naïve HIV, HCV-mono-infected and HIV/HCV-co-infected Chinese", PloS One, 2012, 7:1-9.

Battaglia et al., "Rapamycin selectively expands CD4+D25+FoxP3+ regulatory T cells", Blood, 2005, 105:4743-4748.

Godfrey et al., "Cord blood CD4+D25+derived T regulatory cell lines express FoxP3 protein and manifest potent suppressor function", Blood, 2005, 105:750-758.

Godfrey et al., "In vitro—expanded human CD4+CD25+ T-regulatory cells can markedly inhibit allogeneic dendritic cell-stimulated MLR cultures", Blood, 2004, 104:453-461.

Trzonkowski et al., "First-in-man clinical results of the treatment of patients with graft versus host disease with human ex vivo expanded CD4+CD25+CD127—Tregulatory cells", Clin Immunol, 2009, 133:22-26.

\* cited by examiner

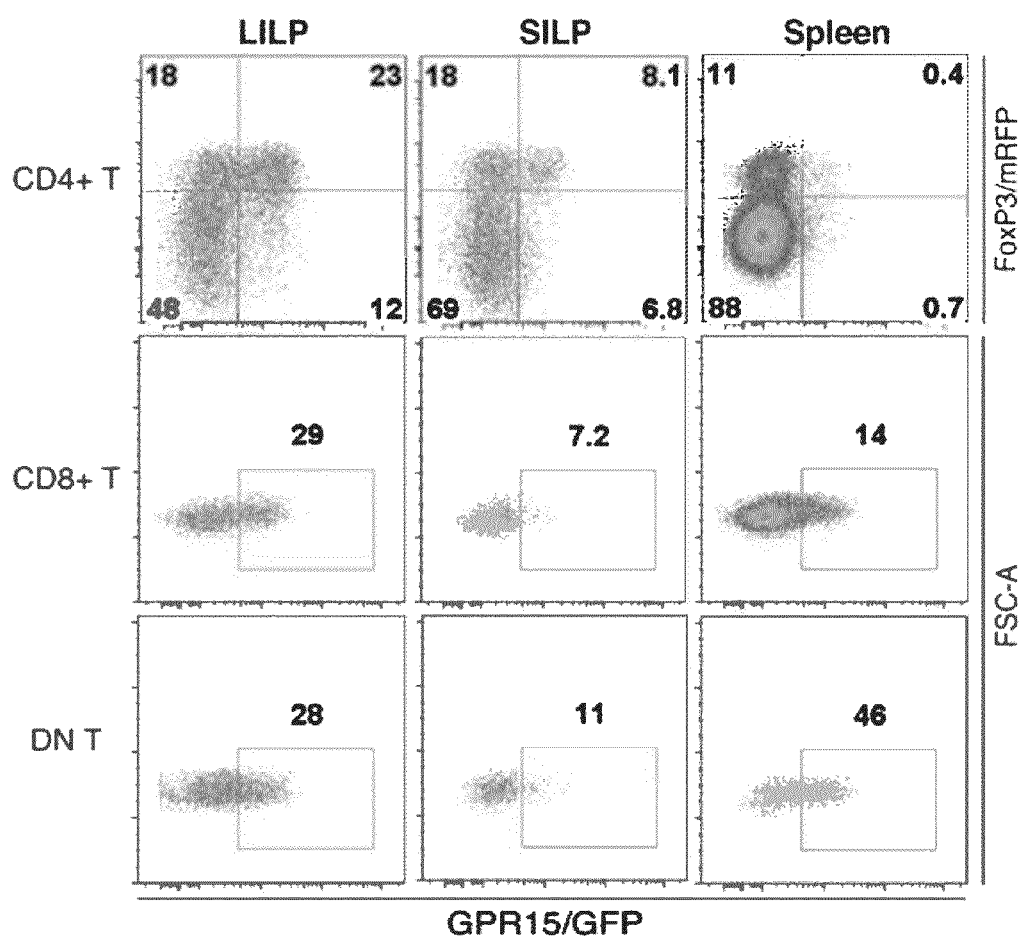

After infection

Foxp3^{sf} + WT

Foxp3^{sf} + KO

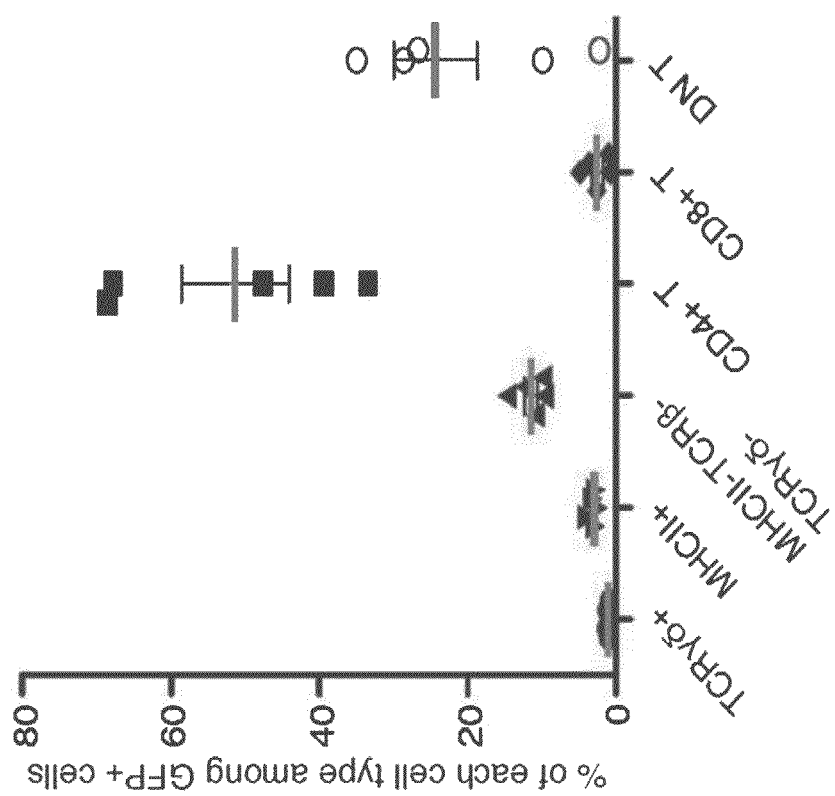

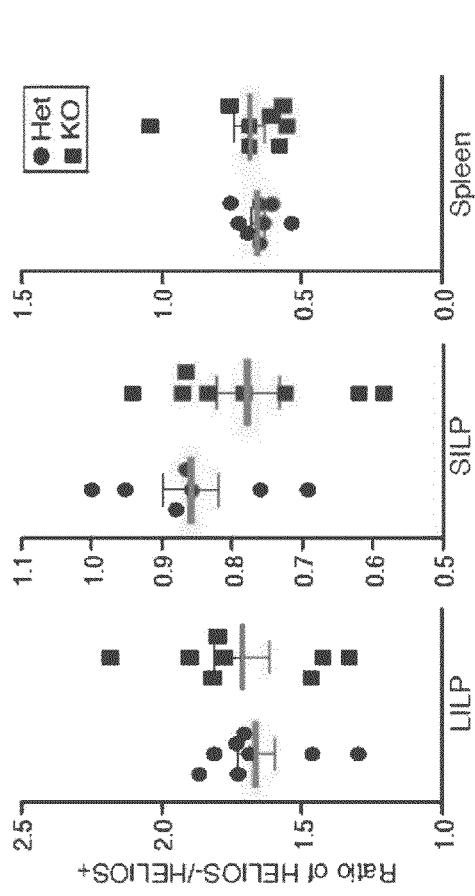
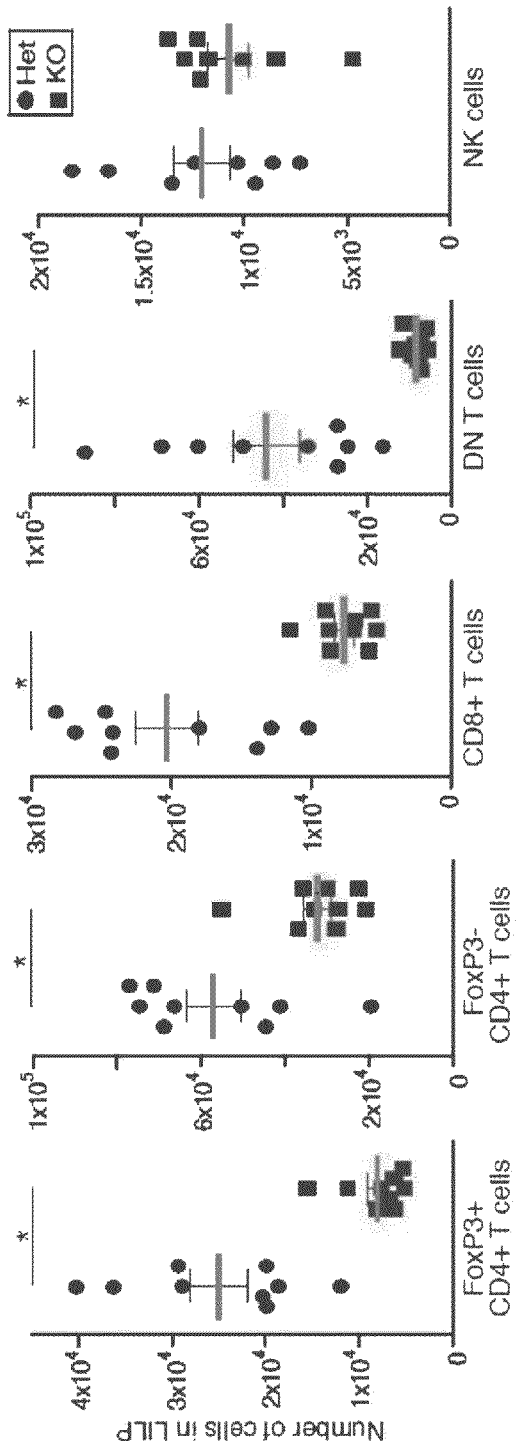

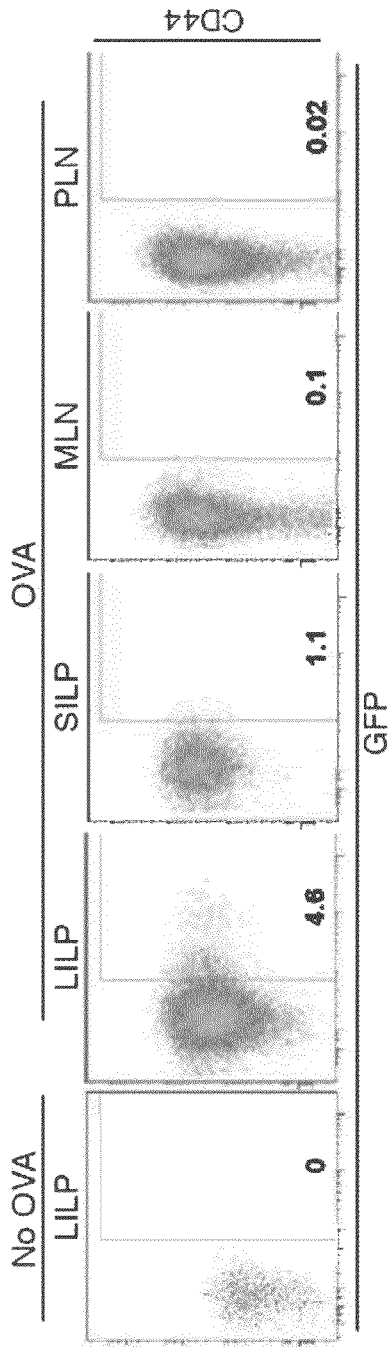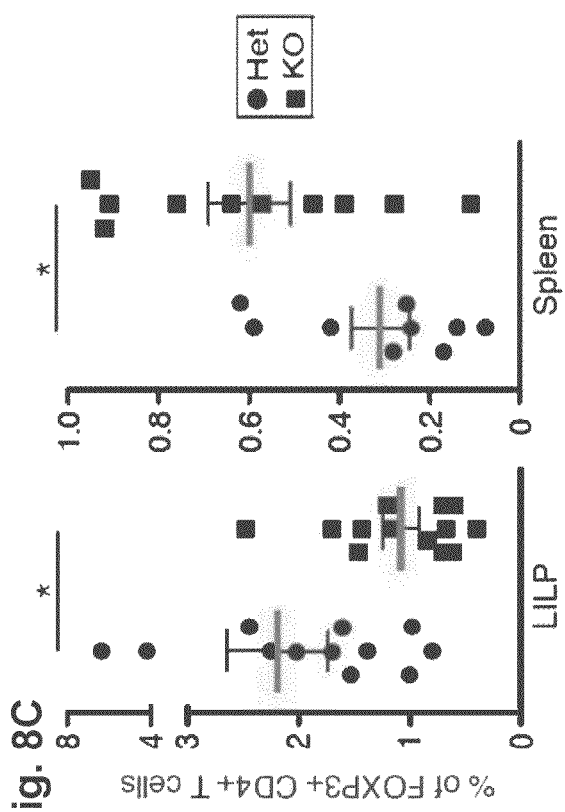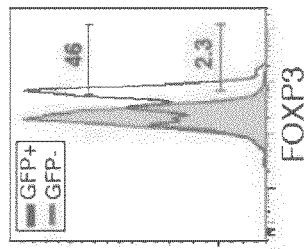
Fig. 8A
Fig. 8B
Fig. 8C

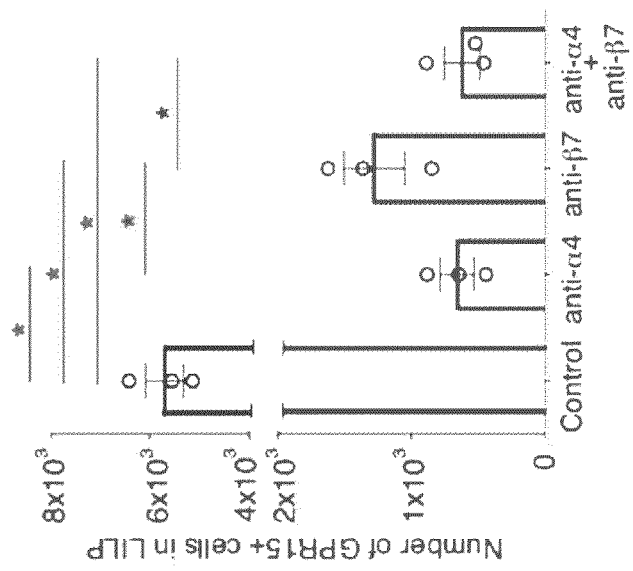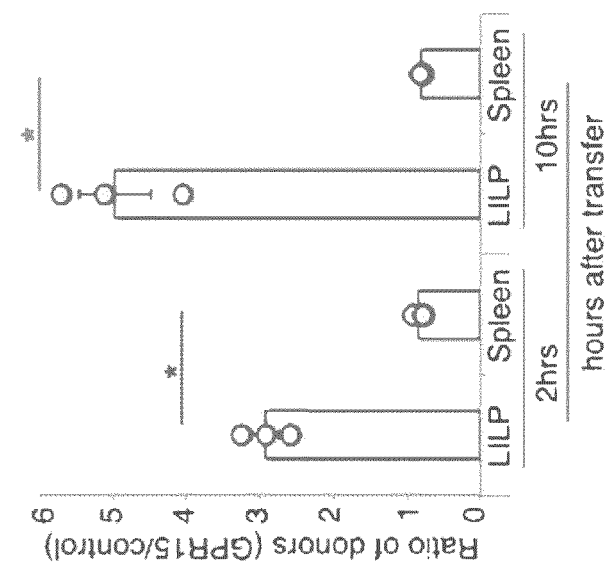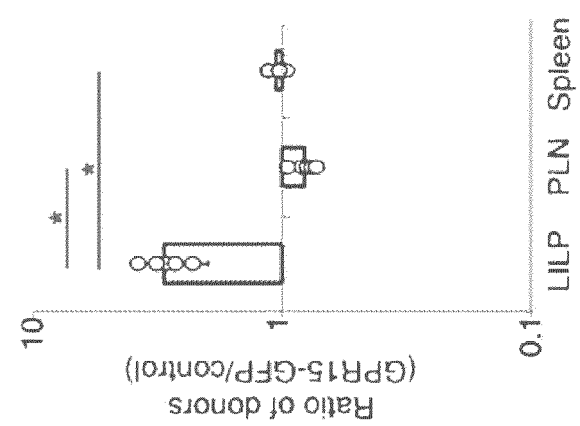

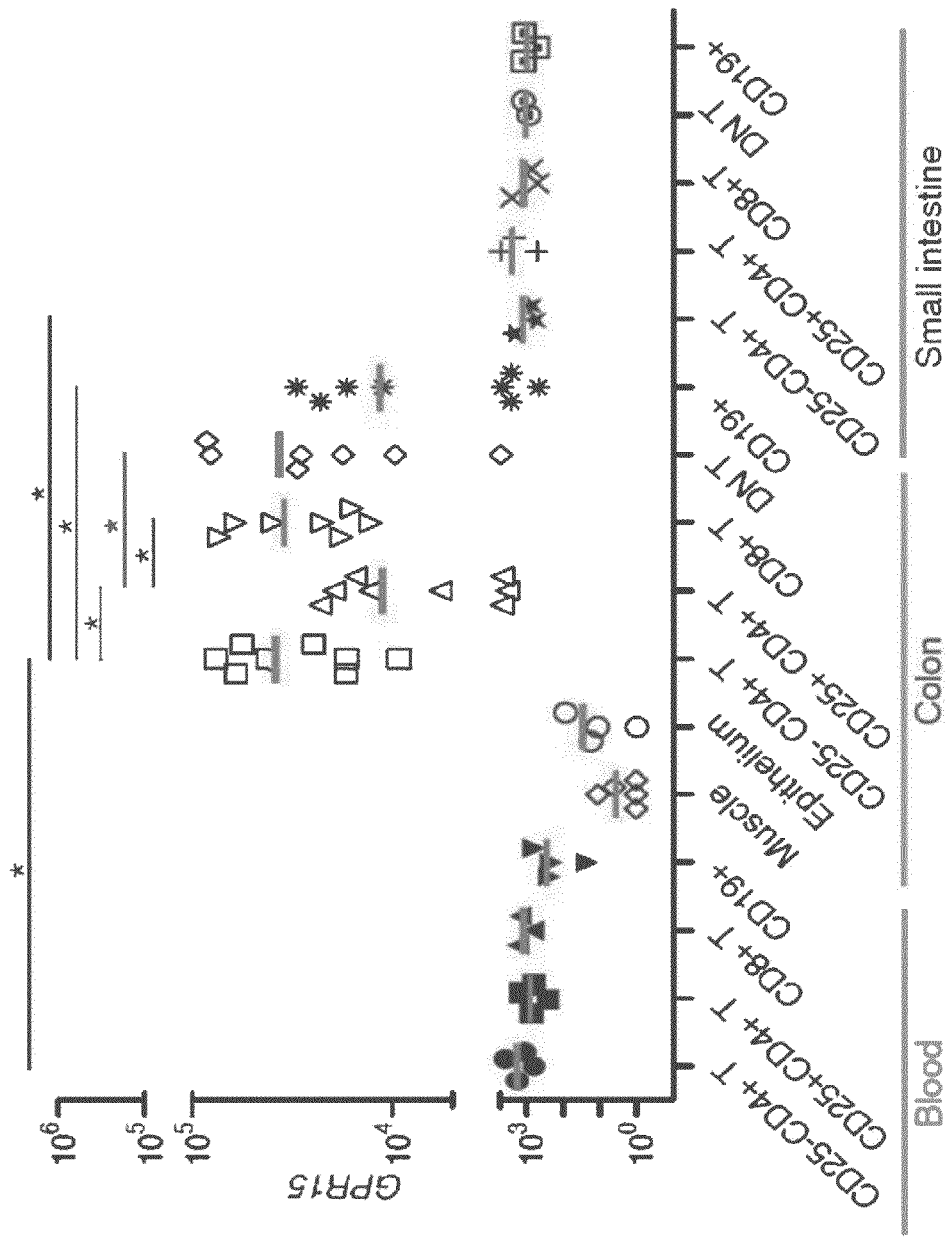

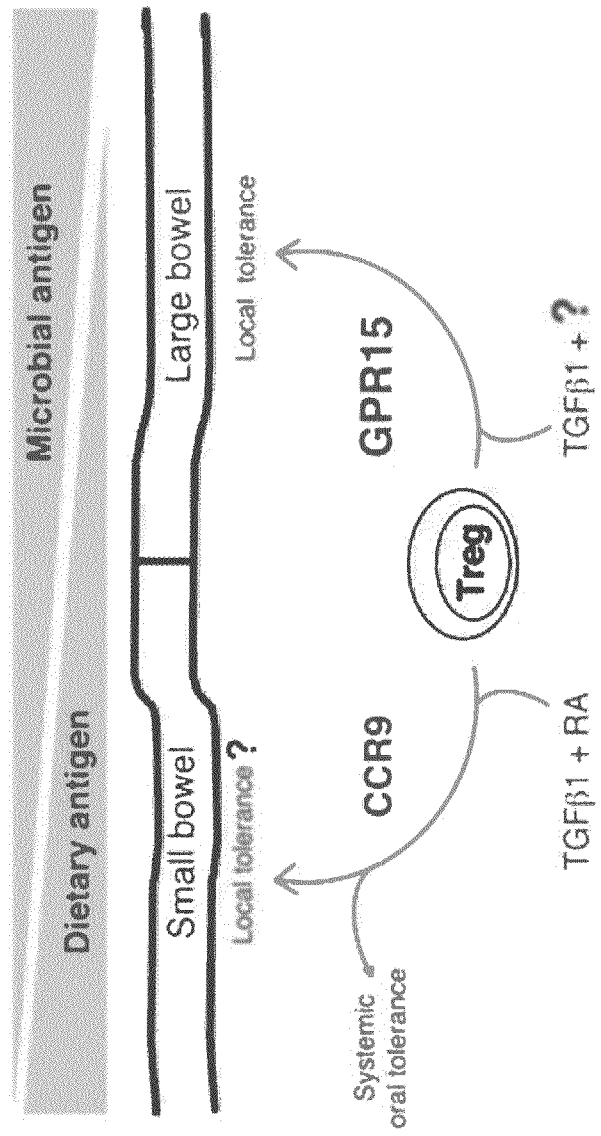

SEQUENCE LISTING

```
<160> NUMBER OF SEQ ID NOS: 26

<210> SEQ ID NO 1
<211> LENGTH: 1083
<212> TYPE: DNA
<213> ORGANISM: Homo sapiens

<400> SEQUENCE: 1 atggaccag aagaaacttc agtttatttg gattattact atgctacgag cccaaactct      60
gacatcaggg agacccactc ccatgttcct tacacctctg tcttccttcc agtcttttac     120
acagctgtgt tcctgactgg agtgctgggg aaccttgttc tcatgggagc gttgcatttc    180
aaacccggca gccgaagact gatcgacatc tttatcatca atctggctgc ctctgacttc    240
atttttcttg tcacattgcc tctctgggtg gataagaag catctctagg actgtggagg     300
acgggctcct tcctgtgcaa agggagctcc tacatgatct ccgtcaatat gcactgcagt    360
gtcctcctgc tcacttgcat gagtgttgac cgctacctgg ccattgtgtg gccagtcgta    420
tccaggaaat tcagaaggac agactgtgca tatgtagtct gtgccagcat ctggtttatc    480
tcctgcctgc tggggttgcc tactcttctg tccagggagc tcacgctgat tgatgataag    540
ccatactgtg cagagaaaaa ggcaactcca attaaactca tatggtccct ggtggcctta    600
attttcacct tttttgtccc tttgttgagc attgtgacct gctactgttg cattgcaagg    660
```

```
aagctgtgtg cccattacca gcaatcagga aagcacaaca aaaagctgaa gaaatctata    720
aagatcatct ttattgtcgt ggcagccttt cttgtctcct ggctgccctt caatactttc    780
aagttcctgg ccattgtctc tgggttgcgg caagaacact atttaccctc agctattctt    840
cagcttggta tggaggtgag tggacccttg gcatttgcca acagctgtgt caacccttc     900 atttactata tcttcgacag ctacatccgc cgggccattg tccactgctt gtgcccttgc    960
ctgaaaaact atgactttgg gagtagcact gagacatcag atagtcacct cactaaggct    1020
ctctccacct tcattcatgc agaagatttt gccaggagga ggaagaggtc tgtgtcactc    1080
taa                                                                  1083

<210> SEQ ID NO 2
<211> LENGTH: 360
<212> TYPE: PRT
<213> ORGANISM: Homo sapiens

<400> SEQUENCE: 2

Met Asp Pro Glu Glu Thr Ser Val Tyr Leu Asp Tyr Tyr Tyr Ala Thr
 1               5                  10                  15

Ser Pro Asn Ser Asp Ile Arg Glu Thr His Ser His Val Pro Tyr Thr
            20                  25                  30

Ser Val Phe Leu Pro Val Phe Tyr Thr Ala Val Phe Leu Thr Gly Val
        35                  40                  45

Leu Gly Asn Leu Val Leu Met Gly Ala Leu His Phe Lys Pro Gly Ser
    50                  55                  60

Arg Arg Leu Ile Asp Ile Phe Ile Ile Asn Leu Ala Ala Ser Asp Phe
65                  70                  75                  80

Ile Phe Leu Val Thr Leu Pro Leu Trp Val Asp Lys Glu Ala Ser Leu
                85                  90                  95

Gly Leu Trp Arg Thr Gly Ser Phe Leu Cys Lys Gly Ser Ser Tyr Met
            100                 105                 110

Ile Ser Val Asn Met His Cys Ser Val Leu Leu Leu Thr Cys Met Ser
        115                 120                 125

Val Asp Arg Tyr Leu Ala Ile Val Trp Pro Val Val Ser Arg Lys Phe
    130                 135                 140

Arg Arg Thr Asp Cys Ala Tyr Val Val Cys Ala Ser Ile Trp Phe Ile
145                 150                 155                 160

Ser Cys Leu Leu Gly Leu Pro Thr Leu Leu Ser Arg Glu Leu Thr Leu
                165                 170                 175

Ile Asp Asp Lys Pro Tyr Cys Ala Glu Lys Lys Ala Thr Pro Ile Lys
            180                 185                 190

Leu Ile Trp Ser Leu Val Ala Leu Ile Phe Thr Phe Phe Val Pro Leu
        195                 200                 205

Leu Ser Ile Val Thr Cys Tyr Cys Cys Ile Ala Arg Lys Leu Cys Ala
    210                 215                 220

His Tyr Gln Gln Ser Gly Lys His Asn Lys Leu Lys Lys Ser Ile
225                 230                 235                 240

Lys Ile Ile Phe Ile Val Val Ala Ala Phe Leu Val Ser Trp Leu Pro
                245                 250                 255

Phe Asn Thr Phe Lys Phe Leu Ala Ile Val Ser Gly Leu Arg Gln Glu
            260                 265                 270

His Tyr Leu Pro Ser Ala Ile Leu Gln Leu Gly Met Glu Val Ser Gly
        275                 280                 285
```

Pro Leu Ala Phe Ala Asn Ser Cys Val Asn Pro Phe Ile Tyr Tyr Ile
290                 295                 300

Phe Asp Ser Tyr Ile Arg Arg Ala Ile Val His Cys Leu Cys Pro Cys
305                 310                 315                 320

Leu Lys Asn Tyr Asp Phe Gly Ser Ser Thr Glu Thr Ser Asp Ser His
            325                 330                 335

Leu Thr Lys Ala Leu Ser Thr Phe Ile His Ala Glu Asp Phe Ala Arg
            340                 345                 350

Arg Arg Lys Arg Ser Val Ser Leu
            355                 360

<210> SEQ ID NO 3
<211> LENGTH: 1083
<212> TYPE: DNA
<213> ORGANISM: Mus musculus

<400> SEQUENCE: 3
atggaaccag caacagccct gctgattgtg gattactatg actacacaag cccagatcct      60
cctttcctgg agactccctc ccacctgtcc tacacatctg tcttcctccc tatctttttac    120
acagttgtat tcttgactgg agtggtgggg aatttcatcc tcatgatagc tctgcatttc     180
aaacgcggca accgaagatt gatcgacatc tttatcatca acctggctgc tctgacttc      240
attttccttg tcacagtgcc tctttggatg ataaggaag cctctctagg actatggagg      300
actggctctt tcctgtgcaa aggcagctcc tatgtgatct ccgtgaacat gcactgtagt     360
gtcttcttgc tcacatgcat gagcatggac cgttacctgg ctatcatgca cccagcctta    420
gccaagagat tacgaaggag aagctctgca tatgcagtgt gtgccgtcgt ctggatcatc     480
tcatgcgtcc tggggttgcc cactcttctg tccagggagc tcactcacat tgaaggcaaa     540
ccatactgtg cagagaagaa acccacgtcc ttaaaactga tgtggggcct ggtagccttg    600
attaccacct ttttcgtccc cctcctgagc attgtgacct gctactgttg catcacaagg    660
aggctgtgtg ctcattacca gcagtcggga aagcataaca agaaactaaa gaagtccata     720
aagatcgtta ttattgcggt ggcggccttc accgtctcct gggtacccctt taacactttc    780
aagctcctag ccattgtttc agggttccag ccagaaggcc ttttttcactc cgaggctttg    840
cagctggcca tgaatgtgac tgggcccttg gcctttgcca gcagctgtgt caaccctctc    900
atttactatg tctttgacag ctatatccgc cgggccattg tacgttgtct gtgcccttgt    960
ctgaagaccc acaactttgg gagcagcact gagacatcgg acagtcacct cactaaggct   1020
cttttccaact tcattcatgc agaggatttc atccggcgga ggaagagatc tgtgtcactc   1080
taa                                                                 1083

<210> SEQ ID NO 4
<211> LENGTH: 360
<212> TYPE: PRT
<213> ORGANISM: Mus musculus

<400> SEQUENCE: 4

Met Glu Pro Ala Thr Ala Leu Leu Ile Val Asp Tyr Tyr Asp Tyr Thr
1               5                   10                  15

Ser Pro Asp Pro Pro Phe Leu Glu Thr Pro Ser His Leu Ser Tyr Thr
            20                  25                  30

Ser Val Phe Leu Pro Ile Phe Tyr Thr Val Val Phe Leu Thr Gly Val
        35                  40                  45

Val Gly Asn Phe Ile Leu Met Ile Ala Leu His Phe Lys Arg Gly Asn

```
            50                  55                  60
Arg Arg Leu Ile Asp Ile Phe Ile Ile Asn Leu Ala Ala Ser Asp Phe
 65                  70                  75                  80

Ile Phe Leu Val Thr Val Pro Leu Trp Met Asp Lys Glu Ala Ser Leu
                 85                  90                  95

Gly Leu Trp Arg Thr Gly Ser Phe Leu Cys Lys Gly Ser Ser Tyr Val
            100                 105                 110

Ile Ser Val Asn Met His Cys Ser Val Phe Leu Leu Thr Cys Met Ser
            115                 120                 125

Met Asp Arg Tyr Leu Ala Ile Met His Pro Ala Leu Ala Lys Arg Leu
        130                 135                 140

Arg Arg Arg Ser Ser Ala Tyr Ala Val Cys Ala Val Val Trp Ile Ile
145                 150                 155                 160

Ser Cys Val Leu Gly Leu Pro Thr Leu Leu Ser Arg Glu Leu Thr His
                165                 170                 175

Ile Glu Gly Lys Pro Tyr Cys Ala Glu Lys Lys Pro Thr Ser Leu Lys
            180                 185                 190

Leu Met Trp Gly Leu Val Ala Leu Ile Thr Thr Phe Phe Val Pro Leu
        195                 200                 205

Leu Ser Ile Val Thr Cys Tyr Cys Cys Ile Thr Arg Arg Leu Cys Ala
210                 215                 220

His Tyr Gln Gln Ser Gly Lys His Asn Lys Lys Leu Lys Lys Ser Ile
225                 230                 235                 240

Lys Ile Val Ile Ile Ala Val Ala Ala Phe Thr Val Ser Trp Val Pro
                245                 250                 255

Phe Asn Thr Phe Lys Leu Leu Ala Ile Val Ser Gly Phe Gln Pro Glu
            260                 265                 270

Gly Leu Phe His Ser Glu Ala Leu Gln Leu Ala Met Asn Val Thr Gly
        275                 280                 285

Pro Leu Ala Phe Ala Ser Ser Cys Val Asn Pro Leu Ile Tyr Tyr Val
290                 295                 300

Phe Asp Ser Tyr Ile Arg Arg Ala Ile Val Arg Cys Leu Cys Pro Cys
305                 310                 315                 320

Leu Lys Thr His Asn Phe Gly Ser Ser Thr Glu Thr Ser Asp Ser His
                325                 330                 335

Leu Thr Lys Ala Leu Ser Asn Phe Ile His Ala Glu Asp Phe Ile Arg
            340                 345                 350

Arg Arg Lys Arg Ser Val Ser Leu
        355                 360

<210> SEQ ID NO 5
<211> LENGTH: 3099
<212> TYPE: DNA
<213> ORGANISM: Homo sapiens

<400> SEQUENCE: 5
atggcttggg aagcgaggcg cgaacccggc ccccgaaggg ccgccgtccg ggagacggtg      60
atgctgttgc tgtgcctggg ggtcccgacc ggccgcccct acaacgtgga cactgagagc     120
gcgctgcttt accagggccc ccacaacacg ctgttcggct actcggtcgt gctgcacagc     180
cacggggcga accgatggct cctagtgggt gcgcccactg ccaactggct cgccaacgct     240
tcagtgatca atcccggggc gatttacaga tgcaggatcg aaagaatccc ggccagacg      300 tgcgaacagc tccagctggg tagccctaat ggagaacctt gtggaaagac ttgtttggaa     360
```

```
gagagagaca atcagtggtt gggggtcaca ctttccagac agccaggaga aaatggatcc    420
atcgtgactt gtgggcatag atggaaaaat atattttaca taaagaatga aaataagctc    480
cccactggtg gttgctatgg agtgcccct gatttacgaa cagaactgag taaaagaata    540
gctccgtgtt atcaagatta tgtgaaaaaa tttggagaaa attttgcatc atgtcaagct    600
ggaatatcca gttttacac aaaggattta attgtgatgg gggcccagg atcatcttac    660 tggactggct ctcttttgt ctacaatata actacaaata aatacaaggc tttttagac    720 aaacaaaatc aagtaaaatt tggaagttat ttaggatatt cagtcggagc tggtcatttt    780
cggagccagc atactaccga agtagtcgga ggagctcctc aacatgagca gattggtaag    840
gcatatatat tcagcattga tgaaaagaa ctaaatatct tacatgaaat gaaaggtaaa    900
aagcttggat cgtactttgg agcttctgtc tgtgctgtgg acctcaatgc agatggcttc    960
tcagatctgc tcgtgggagc acccatgcag agcaccatca gagaggaagg aagagtgttt   1020
gtgtacatca actctggctc gggagcagta atgaatgcaa tggaaacaaa cctcgttgga   1080
agtgacaaat atgctgcaag atttggggaa tctatagtta atcttggcga cattgacaat   1140
gatggctttg aagatgttgc tatcggagct ccacaagaag atgacttgca aggtgctatt   1200
tatatttaca atggccgtgc agatgggatc tcgtcaacct tctcacagag aattgaagga   1260
cttcagatca gcaaatcgtt aagtatgttt ggacagtcta tatcaggaca aattgatgca   1320
gataataatg gctatgtaga tgtagcagtt ggtgcttttc ggtctgattc tgctgtcttg   1380
ctaaggacaa gacctgtagt aattgttgac gcttctttaa gccaccctga gtcagtaaat   1440
agaacgaaat ttgactgtgt tgaaaatgga tggccttctg tgtgcataga tctaacactt   1500
tgtttctcat ataagggcaa ggaagttcca ggttacattg ttttgttta aacatgagt   1560 ttggatgtga acagaaaggc agagtctcca ccaagattct atttctcttc taatggaact   1620
tctgacgtga ttacaggaag catacaggtg tccagcagag aagctaactg tagaacacat   1680
caagcattta tgcggaaaga tgtgcgggac atcctcaccc caattcagat tgaagctgct   1740
taccaccttg gtcctcatgt catcagtaaa cgaagtacag aggaattccc accacttcag   1800
ccaattcttc agcagaagaa agaaaaagac ataatgaaaa aaacaataaa ctttgcaagg   1860
ttttgtgccc atgaaaattg ttctgctgat ttacaggttt ctgcaaagat tgggtttttg   1920 aagcccatg aaaataaaac atatcttgct gttgggagta tgaagacatt gatgttgaat   1980
gtgtccttgt ttaatgctgg agatgatgca tatgaaacga ctctacatgt caaactaccc   2040
gtgggtcttt atttcattaa gattttagag ctggaagaga agcaaataaa ctgtgaagtc   2100
acagataact ctggcgtggt acaacttgac tgcagtattg gctatatata tgtagatcat   2160
ctctcaagga tagatattag ctttctcctg gatgtgagct cactcagcag agcggaagag   2220
gacctcagta tcacagtgca tgctacctgt gaaaatgaag aggaaatgga caatctaaag   2280
cacagcagag tgactgtagc aatacctta aaatatgagg ttaagctgac tgttcatggg   2340
tttgtaaacc caacttcatt tgtgtatgga tcaaatgatg aaaatgagcc tgaaacgtgc   2400
atggtggaga aaatgaactt aactttccat gttatcaaca ctggcaatag tatggctccc   2460
aatgttagtg tggaaataat ggtaccaaat tctttagcc cccaaactga taagctgttc   2520
aacattttgg atgtccagac tactactgga gaatgccact ttgaaaatta tcaaagagtg   2580
tgtgcattag agcagcaaaa gagtgcaatg cagaccttga aaggcatagt ccggttcttg   2640
tccaagactg ataagaggct attgtactgc ataaaagctg atccacattg tttaaatttc   2700
ttgtgtaatt ttgggaaaat ggaaagtgga aagaagcca gtgttcatat ccaactggaa   2760
```

-continued

```
ggccggccat ccatttagaa aatggatgag acttcagcac tcaagtttga aataagagca    2820
acaggttttc cagagccaaa tccaagagta attgaactaa acaaggatga gaatgttgcg    2880
catgttctac tggaaggact acatcatcaa agacccaaac gttatttcac catagtgatt    2940
atttcaagta gcttgctact tggacttatt gtacttctgt tgatctcata tgttatgtgg    3000
aaggctggct tctttaaaag acaatacaaa tctatcctac aagaagaaaa cagaagagac    3060
agttggagtt atatcaacag taaaagcaat gatgattaa                           3099
```

<210> SEQ ID NO 6
<211> LENGTH: 1032
<212> TYPE: PRT
<213> ORGANISM: Homo sapiens

<400> SEQUENCE: 6

```
Met Ala Trp Glu Ala Arg Arg Glu Pro Gly Pro Arg Arg Ala Val
 1               5                  10                  15

Arg Glu Thr Val Met Leu Leu Cys Leu Gly Val Pro Thr Gly Arg
                20                  25                  30

Pro Tyr Asn Val Asp Thr Glu Ser Ala Leu Leu Tyr Gln Gly Pro His
                35                  40                  45

Asn Thr Leu Phe Gly Tyr Ser Val Val Leu His Ser His Gly Ala Asn
 50                  55                  60

Arg Trp Leu Leu Val Gly Ala Pro Thr Ala Asn Trp Leu Ala Asn Ala
 65                  70                  75                  80

Ser Val Ile Asn Pro Gly Ala Ile Tyr Arg Cys Arg Ile Gly Lys Asn
                85                  90                  95

Pro Gly Gln Thr Cys Glu Gln Leu Gln Leu Gly Ser Pro Asn Gly Glu
                100                 105                 110

Pro Cys Gly Lys Thr Cys Leu Glu Glu Arg Asp Asn Gln Trp Leu Gly
                115                 120                 125

Val Thr Leu Ser Arg Gln Pro Gly Glu Asn Gly Ser Ile Val Thr Cys
                130                 135                 140

Gly His Arg Trp Lys Asn Ile Phe Tyr Ile Lys Asn Glu Asn Lys Leu
145                 150                 155                 160

Pro Thr Gly Gly Cys Tyr Gly Val Pro Pro Asp Leu Arg Thr Glu Leu
                165                 170                 175

Ser Lys Arg Ile Ala Pro Cys Tyr Gln Asp Tyr Val Lys Lys Phe Gly
                180                 185                 190

Glu Asn Phe Ala Ser Cys Gln Ala Gly Ile Ser Ser Phe Tyr Thr Lys
                195                 200                 205

Asp Leu Ile Val Met Gly Ala Pro Gly Ser Ser Tyr Trp Thr Gly Ser
                210                 215                 220

Leu Phe Val Tyr Asn Ile Thr Thr Asn Lys Tyr Lys Ala Phe Leu Asp
225                 230                 235                 240

Lys Gln Asn Gln Val Lys Phe Gly Ser Tyr Leu Gly Tyr Ser Val Gly
                245                 250                 255

Ala Gly His Phe Arg Ser Gln His Thr Thr Glu Val Val Gly Gly Ala
                260                 265                 270

Pro Gln His Glu Gln Ile Gly Lys Ala Tyr Ile Phe Ser Ile Asp Glu
                275                 280                 285

Lys Glu Leu Asn Ile Leu His Glu Met Lys Gly Lys Lys Leu Gly Ser
                290                 295                 300

Tyr Phe Gly Ala Ser Val Cys Ala Val Asp Leu Asn Ala Asp Gly Phe
```

```
            305                 310                 315                 320
Ser Asp Leu Leu Val Gly Ala Pro Met Gln Ser Thr Ile Arg Glu Glu
                    325                 330                 335
Gly Arg Val Phe Val Tyr Ile Asn Ser Gly Ser Gly Ala Val Met Asn
                    340                 345                 350
Ala Met Glu Thr Asn Leu Val Gly Ser Asp Lys Tyr Ala Ala Arg Phe
                    355                 360                 365
Gly Glu Ser Ile Val Asn Leu Gly Asp Ile Asp Asn Asp Gly Phe Glu
                    370                 375                 380
Asp Val Ala Ile Gly Ala Pro Gln Glu Asp Asp Leu Gln Gly Ala Ile
385                 390                 395                 400
Tyr Ile Tyr Asn Gly Arg Ala Asp Gly Ile Ser Ser Thr Phe Ser Gln
                    405                 410                 415
Arg Ile Glu Gly Leu Gln Ile Ser Lys Ser Leu Ser Met Phe Gly Gln
                    420                 425                 430
Ser Ile Ser Gly Gln Ile Asp Ala Asp Asn Asn Gly Tyr Val Asp Val
                    435                 440                 445
Ala Val Gly Ala Phe Arg Ser Asp Ser Ala Val Leu Leu Arg Thr Arg
                    450                 455                 460
Pro Val Val Ile Val Asp Ala Ser Leu Ser His Pro Glu Ser Val Asn
465                 470                 475                 480
Arg Thr Lys Phe Asp Cys Val Glu Asn Gly Trp Pro Ser Val Cys Ile
                    485                 490                 495
Asp Leu Thr Leu Cys Phe Ser Tyr Lys Gly Lys Glu Val Pro Gly Tyr
                    500                 505                 510
Ile Val Leu Phe Tyr Asn Met Ser Leu Asp Val Asn Arg Lys Ala Glu
                    515                 520                 525
Ser Pro Pro Arg Phe Tyr Phe Ser Ser Asn Gly Thr Ser Asp Val Ile
                    530                 535                 540
Thr Gly Ser Ile Gln Val Ser Ser Arg Glu Ala Asn Cys Arg Thr His
545                 550                 555                 560
Gln Ala Phe Met Arg Lys Asp Val Arg Asp Ile Leu Thr Pro Ile Gln
                    565                 570                 575
Ile Glu Ala Ala Tyr His Leu Gly Pro His Val Ile Ser Lys Arg Ser
                    580                 585                 590
Thr Glu Glu Phe Pro Pro Leu Gln Pro Ile Leu Gln Gln Lys Lys Glu
                    595                 600                 605
Lys Asp Ile Met Lys Lys Thr Ile Asn Phe Ala Arg Phe Cys Ala His
                    610                 615                 620
Glu Asn Cys Ser Ala Asp Leu Gln Val Ser Ala Lys Ile Gly Phe Leu
625                 630                 635                 640
Lys Pro His Glu Asn Lys Thr Tyr Leu Ala Val Gly Ser Met Lys Thr
                    645                 650                 655
Leu Met Leu Asn Val Ser Leu Phe Asn Ala Gly Asp Asp Ala Tyr Glu
                    660                 665                 670
Thr Thr Leu His Val Lys Leu Pro Val Gly Leu Tyr Phe Ile Lys Ile
                    675                 680                 685
Leu Glu Leu Glu Glu Lys Gln Ile Asn Cys Glu Val Thr Asp Asn Ser
                    690                 695                 700
Gly Val Val Gln Leu Asp Cys Ser Ile Gly Tyr Ile Tyr Val Asp His
705                 710                 715                 720
Leu Ser Arg Ile Asp Ile Ser Phe Leu Leu Asp Val Ser Ser Leu Ser
                    725                 730                 735
```

| | | | | | | | | | | | |
|---|---|---|---|---|---|---|---|---|---|---|---|
| Arg | Ala | Glu | Glu | Asp | Leu | Ser | Ile | Thr | Val | His | Ala | Thr | Cys | Glu | Asn |
| | | | 740 | | | | 745 | | | | 750 | | | |

Arg Ala Glu Glu Asp Leu Ser Ile Thr Val His Ala Thr Cys Glu Asn
          740                 745                 750

Glu Glu Glu Met Asp Asn Leu Lys His Ser Arg Val Thr Val Ala Ile
              755                 760                 765

Pro Leu Lys Tyr Glu Val Lys Leu Thr Val His Gly Phe Val Asn Pro
      770                 775                 780

Thr Ser Phe Val Tyr Gly Ser Asn Asp Glu Asn Glu Pro Glu Thr Cys
785                 790                 795                 800

Met Val Glu Lys Met Asn Leu Thr Phe His Val Ile Asn Thr Gly Asn
                  805                 810                 815

Ser Met Ala Pro Asn Val Ser Val Glu Ile Met Val Pro Asn Ser Phe
              820                 825                 830

Ser Pro Gln Thr Asp Lys Leu Phe Asn Ile Leu Asp Val Gln Thr Thr
          835                 840                 845

Thr Gly Glu Cys His Phe Glu Asn Tyr Gln Arg Val Cys Ala Leu Glu
      850                 855                 860

Gln Gln Lys Ser Ala Met Gln Thr Leu Lys Gly Ile Val Arg Phe Leu
865                 870                 875                 880

Ser Lys Thr Asp Lys Arg Leu Leu Tyr Cys Ile Lys Ala Asp Pro His
                  885                 890                 895

Cys Leu Asn Phe Leu Cys Asn Phe Gly Lys Met Glu Ser Gly Lys Glu
              900                 905                 910

Ala Ser Val His Ile Gln Leu Glu Gly Arg Pro Ser Ile Leu Glu Met
          915                 920                 925

Asp Glu Thr Ser Ala Leu Lys Phe Glu Ile Arg Ala Thr Gly Phe Pro
      930                 935                 940

Glu Pro Asn Pro Arg Val Ile Glu Leu Asn Lys Asp Glu Asn Val Ala
945                 950                 955                 960

His Val Leu Leu Glu Gly Leu His His Gln Arg Pro Lys Arg Tyr Phe
                  965                 970                 975

Thr Ile Val Ile Ile Ser Ser Ser Leu Leu Leu Gly Leu Ile Val Leu
              980                 985                 990

Leu Leu Ile Ser Tyr Val Met Trp Lys Ala Gly Phe Phe Lys Arg Gln
          995                 1000                1005

Tyr Lys Ser Ile Leu Gln Glu Glu Asn Arg Arg Asp Ser Trp Ser Tyr
    1010                1015                1020

Ile Asn Ser Lys Ser Asn Asp Asp
1025                1030

<210> SEQ ID NO 7
<211> LENGTH: 3099
<212> TYPE: DNA
<213> ORGANISM: Mus musculus

<400> SEQUENCE: 7
atggctgcgg aagcgaggtg cagaccgagg tcccgaggga tcgccctccg ggaagcggtg     60
atgctgttgt tgtacttcgg ggtgccaacc gggcactcct acaacctgga cccggagaat    120
gcactgctgt accagggccc ctccggcacg ctgtttggct actcggtggt gctgcacagc    180
cacgggtcga agcgctggct catcgtgggg gctcccactg ccagctggct ctctaatgcc    240
tcagtggtca tcctggggc gatttacaga tgcgggatca gaagaatcc aaaccagacc     300 tgcgaacagc tccagctggg tagccccagt ggagagcctt gtgggaagac atgcctggag    360
gagagggata ccagtggct gggggtcacc ctttccagac agcctggaga aaatggctct    420

```
atcgtgactt gtgggcacag gtggaaaaat attttttaca tgaagagcga taacaaactc    480
cccactggca tttgctacgt catgccttct gatttgcgga cagaactgag taaaaggatg    540
gccccgtgtt acaaagatta tacgagaaaa tttggagaaa attttgcatc atgtcaagct    600
ggaatatcta gttttacac acaggattta attgtgatgg gggcccgggg atcatcgtac     660
tggactggca ccgtctttgt ctacaatata actacaaacc aatacaaagc atttgtagac    720
agacagaacc aagtaaaatt tggaagctac ttaggctact cagttggagc tggacatttt    780
cgaagtccac atactaccga agtcgtggga ggagcccctc aacacgaaca gataggaaaa    840
gcatatatat ttagcattga tgaaaacgaa ctgaacatcg tatatgaaat gaaaggtaaa    900
aagcttggct catactttgg agcttctgtc tgcgctgtgg acctcaatgc agatggcttc    960
tcagatctcc ttgttggagc tcccatgcag agcaccatca gggaggaagg aagagtattc    1020
gtgtacatca actctggcat gggagctgtg atggttgaaa tggaaagggt ccttgtcgga    1080
agtgacaaat atgctgcaag atttggggag tctatagcga atcttggcga cattgacaat    1140
gacggctttg aagatattgc tattggtgca ccacaagaag acgacttgag aggtgctgtc    1200
tacatttaca atggccgagt cgatggaatc tcctccacct actcacagag aattgaagga    1260
cagcaaatca gcaaatcatt aaggatgttt ggacaatcta tctcaggaca aattgatgca    1320
gacaacaatg gatatgttga tgtagccgtt ggtgcatttc aatctgattc tgcagtgttg    1380
ctaaggacaa ggcctgtagt gattgttgaa gcatctttaa gccatcctga gtctgtaaat    1440
aggacaaagt ttgactgtac tgaaaatgga cttccatctg tgtgcatgca tcttacactg    1500
tgtttctcat ataaaggcaa agaggtccca ggctacatcg ttttgttta caatgtgagc     1560
ttggatgtgc acaggaaggc agagtctccg tcaagatttt atttcttctc taatgggact    1620
tctgacgtga ttacaggaag catacgagtt tcaagcagtg gagagaaatg taggacacac    1680
caggcattca tgcggaaaga cgtgcgagac atccttaccc ccattcatgt agaggccaca    1740
taccaccttg ggcatcatgt gatcaccaaa cgaaacactg aggaatttcc accactccag    1800
ccgatcccttc agcagaagaa agaaaaagac gttattagaa aaatgataaa cttttgcaagg   1860
ttttgtgcct atgaaaattg ctctgctgat ctccaagttt ctgcaaaagt tggattttg    1920
aagccatatg aaaataaaac ctatcttgct gttgggagca tgaagaccat aatgctaaac    1980
gtgtccttgt tcaacgctgg cgatgatgct tacgaaacca ctctgaatgt ccaactcccc    2040
acaggccttt atttcattaa gatcttagac ctggaagaga acaaataaa ctgcgaagtg     2100
actgagagct caggcatagt gaagcttgcc tgcagcctag ttacatata tgtggatcgc      2160
ctctcaagga tagacattag ctttctcctg gatgtgagct cactcagcag ggcacatgag    2220
gacctcagca tcagtgtgca tgcctcctgt gaaaacgagg gcgaattgga ccaagtgagg    2280
gacaacagag tgaccttaac gatacctcta aggtatgagg ttatgctgac tgttcatggg    2340
cttgtgaacc caacttcatt tgtgtatgga tctagcgaag aaaacgagcc agaaacatgc    2400
atggccgaga agctgaacct cactttccat gttataaaca ctgggattag catggctcca    2460
aatgttagtg tgaaaataat ggtaccaaat tcttttctcc ctcaagatga taagttgttc    2520
aacgttttgg atgtccagac aactacaggg caatgccatt ttaaacacta tggaagagag    2580
tgtacatttg cacagcaaaa aggcatagcg gggacgttga ccgatatagt caaattccta    2640
tcaaagactg ataagagact cctgtattgc atgaaagctg atcaacactg tttagatttc    2700
ttatgcaatt tcggaaaaat ggaaagtggg aaggaagcca gcgttcatat tcagctggag    2760
```

```
ggcaggccat ccatcttgga aatggatgag acctcatcac tcaagtttga aataaaagca      2820
acagcttttc cagagccaca cccaaaagtt attgaactaa ataaagatga gaacgtggcc      2880
catgttttct tggaagggct ccatcatcaa agacccaaac gacatttcac catcattatt      2940
attaccatca gcttgctact tggacttatt gtacttttat taatttcatg tgttatgtgg      3000
aaggctggat tctttaaaag acagtacaaa tctatcctac aagaagaaaa caggagagac      3060
agctggagtt atgtcaacag caaaagcaat gatgactga                             3099
```

<210> SEQ ID NO 8
<211> LENGTH: 1032
<212> TYPE: PRT
<213> ORGANISM: Mus musculus

<400> SEQUENCE: 8

```
Met Ala Ala Glu Ala Arg Cys Arg Pro Arg Ser Arg Gly Ile Ala Leu
 1               5                  10                  15

Arg Glu Ala Val Met Leu Leu Leu Tyr Phe Gly Val Pro Thr Gly His
            20                  25                  30

Ser Tyr Asn Leu Asp Pro Glu Asn Ala Leu Leu Tyr Gln Gly Pro Ser
        35                  40                  45

Gly Thr Leu Phe Gly Tyr Ser Val Val Leu His Ser His Gly Ser Lys
    50                  55                  60

Arg Trp Leu Ile Val Gly Ala Pro Thr Ala Ser Trp Leu Ser Asn Ala
65                  70                  75                  80

Ser Val Val Asn Pro Gly Ala Ile Tyr Arg Cys Gly Ile Arg Lys Asn
                85                  90                  95

Pro Asn Gln Thr Cys Glu Gln Leu Gln Leu Gly Ser Pro Ser Gly Glu
           100                 105                 110

Pro Cys Gly Lys Thr Cys Leu Glu Arg Asp Asn Gln Trp Leu Gly
           115                 120                 125

Val Thr Leu Ser Arg Gln Pro Gly Glu Asn Gly Ser Ile Val Thr Cys
       130                 135                 140

Gly His Arg Trp Lys Asn Ile Phe Tyr Met Lys Ser Asp Asn Lys Leu
145                 150                 155                 160

Pro Thr Gly Ile Cys Tyr Val Met Pro Ser Asp Leu Arg Thr Glu Leu
                165                 170                 175

Ser Lys Arg Met Ala Pro Cys Tyr Lys Asp Tyr Thr Arg Lys Phe Gly
            180                 185                 190

Glu Asn Phe Ala Ser Cys Gln Ala Gly Ile Ser Ser Phe Tyr Thr Gln
        195                 200                 205

Asp Leu Ile Val Met Gly Ala Pro Gly Ser Ser Tyr Trp Thr Gly Thr
    210                 215                 220

Val Phe Val Tyr Asn Ile Thr Thr Asn Gln Tyr Lys Ala Phe Val Asp
225                 230                 235                 240

Arg Gln Asn Gln Val Lys Phe Gly Ser Tyr Leu Gly Tyr Ser Val Gly
                245                 250                 255

Ala Gly His Phe Arg Ser Pro His Thr Thr Glu Val Val Gly Gly Ala
            260                 265                 270

Pro Gln His Glu Gln Ile Gly Lys Ala Tyr Ile Phe Ser Ile Asp Glu
        275                 280                 285

Asn Glu Leu Asn Ile Val Tyr Glu Met Lys Gly Lys Lys Leu Gly Ser
    290                 295                 300

Tyr Phe Gly Ala Ser Val Cys Ala Val Asp Leu Asn Ala Asp Gly Phe
305                 310                 315                 320
```

```
Ser Asp Leu Leu Val Gly Ala Pro Met Gln Ser Thr Ile Arg Glu Glu
            325                 330                 335

Gly Arg Val Phe Val Tyr Ile Asn Ser Gly Met Gly Ala Val Met Val
            340                 345                 350

Glu Met Glu Arg Val Leu Val Gly Ser Asp Lys Tyr Ala Ala Arg Phe
            355                 360                 365

Gly Glu Ser Ile Ala Asn Leu Gly Asp Ile Asp Asn Asp Gly Phe Glu
            370                 375                 380

Asp Ile Ala Ile Gly Ala Pro Gln Glu Asp Asp Leu Arg Gly Ala Val
385                 390                 395                 400

Tyr Ile Tyr Asn Gly Arg Val Asp Gly Ile Ser Ser Thr Tyr Ser Gln
            405                 410                 415

Arg Ile Glu Gly Gln Gln Ile Ser Lys Ser Leu Arg Met Phe Gly Gln
            420                 425                 430

Ser Ile Ser Gly Gln Ile Asp Ala Asp Asn Asn Gly Tyr Val Asp Val
            435                 440                 445

Ala Val Gly Ala Phe Gln Ser Asp Ser Ala Val Leu Leu Arg Thr Arg
            450                 455                 460

Pro Val Val Ile Val Glu Ala Ser Leu Ser His Pro Glu Ser Val Asn
465                 470                 475                 480

Arg Thr Lys Phe Asp Cys Thr Glu Asn Gly Leu Pro Ser Val Cys Met
            485                 490                 495

His Leu Thr Leu Cys Phe Ser Tyr Lys Gly Lys Glu Val Pro Gly Tyr
            500                 505                 510

Ile Val Leu Phe Tyr Asn Val Ser Leu Asp Val His Arg Lys Ala Glu
            515                 520                 525

Ser Pro Ser Arg Phe Tyr Phe Phe Ser Asn Gly Thr Ser Asp Val Ile
            530                 535                 540

Thr Gly Ser Ile Arg Val Ser Ser Ser Gly Glu Lys Cys Arg Thr His
545                 550                 555                 560

Gln Ala Phe Met Arg Lys Asp Val Arg Asp Ile Leu Thr Pro Ile His
            565                 570                 575

Val Glu Ala Thr Tyr His Leu Gly His His Val Ile Thr Lys Arg Asn
            580                 585                 590

Thr Glu Glu Phe Pro Pro Leu Gln Pro Ile Leu Gln Gln Lys Lys Glu
            595                 600                 605

Lys Asp Val Ile Arg Lys Met Ile Asn Phe Ala Arg Phe Cys Ala Tyr
            610                 615                 620

Glu Asn Cys Ser Ala Asp Leu Gln Val Ser Ala Lys Val Gly Phe Leu
625                 630                 635                 640

Lys Pro Tyr Glu Asn Lys Thr Tyr Leu Ala Val Gly Ser Met Lys Thr
            645                 650                 655

Ile Met Leu Asn Val Ser Leu Phe Asn Ala Gly Asp Asp Ala Tyr Glu
            660                 665                 670

Thr Thr Leu Asn Val Gln Leu Pro Thr Gly Leu Tyr Phe Ile Lys Ile
            675                 680                 685

Leu Asp Leu Glu Glu Lys Gln Ile Asn Cys Glu Val Thr Glu Ser Ser
            690                 695                 700

Gly Ile Val Lys Leu Ala Cys Ser Leu Gly Tyr Ile Tyr Val Asp Arg
705                 710                 715                 720

Leu Ser Arg Ile Asp Ile Ser Phe Leu Leu Asp Val Ser Ser Leu Ser
            725                 730                 735
```

Arg Ala His Glu Asp Leu Ser Ile Ser Val His Ala Ser Cys Glu Asn
            740                 745                 750

Glu Gly Glu Leu Asp Gln Val Arg Asp Asn Arg Val Thr Leu Thr Ile
        755                 760                 765

Pro Leu Arg Tyr Glu Val Met Leu Thr Val His Gly Leu Val Asn Pro
    770                 775                 780

Thr Ser Phe Val Tyr Gly Ser Glu Glu Asn Glu Pro Glu Thr Cys
785                 790                 795                 800

Met Ala Glu Lys Leu Asn Leu Thr Phe His Val Ile Asn Thr Gly Ile
                805                 810                 815

Ser Met Ala Pro Asn Val Ser Val Lys Ile Met Val Pro Asn Ser Phe
            820                 825                 830

Leu Pro Gln Asp Asp Lys Leu Phe Asn Val Leu Asp Val Gln Thr Thr
        835                 840                 845

Thr Gly Gln Cys His Phe Lys His Tyr Gly Arg Glu Cys Thr Phe Ala
    850                 855                 860

Gln Gln Lys Gly Ile Ala Gly Thr Leu Thr Asp Ile Val Lys Phe Leu
865                 870                 875                 880

Ser Lys Thr Asp Lys Arg Leu Leu Tyr Cys Met Lys Ala Asp Gln His
                885                 890                 895

Cys Leu Asp Phe Leu Cys Asn Phe Gly Lys Met Glu Ser Gly Lys Glu
            900                 905                 910

Ala Ser Val His Ile Gln Leu Glu Gly Arg Pro Ser Ile Leu Glu Met
        915                 920                 925

Asp Glu Thr Ser Ser Leu Lys Phe Glu Ile Lys Ala Thr Ala Phe Pro
    930                 935                 940

Glu Pro His Pro Lys Val Ile Glu Leu Asn Lys Asp Glu Asn Val Ala
945                 950                 955                 960

His Val Phe Leu Glu Gly Leu His Gln Arg Pro Lys Arg His Phe
                965                 970                 975

Thr Ile Ile Ile Thr Ile Ser Leu Leu Leu Gly Leu Ile Val Leu
            980                 985                 990

Leu Leu Ile Ser Cys Val Met Trp Lys Ala Gly Phe Phe Lys Arg Gln
        995                 1000                1005

Tyr Lys Ser Ile Leu Gln Glu Glu Asn Arg Arg Asp Ser Trp Ser Tyr
    1010                1015                1020

Val Asn Ser Lys Ser Asn Asp Asp
1025                1030

<210> SEQ ID NO 9
<211> LENGTH: 2397
<212> TYPE: DNA
<213> ORGANISM: Homo sapiens

<400> SEQUENCE: 9
atggtggctt tgccaatggt ccttgttttg ctgctggtcc tgagcagagg tgagagtgaa    60
ttggacgcca agatcccatc cacagggat gccacagaat ggcggaatcc tcacctgtcc   120 atgctgggt cctgccagcc agcccctcc tgccagaagt gcatcctctc acacccagc    180 tgtgcatggt gcaagcaact gaacttcacc gcgtcgggag aggcggaggc gcggcgctgc   240
gcccgacgag aggagctgct ggctcgaggc tgcccgctgg aggagctgga ggagccccgc   300
ggccagcagg aggtgctgca ggaccagccg ctcagccagg gcgcccgcgg agagggtgcc   360
acccagctgg cgccgcagcg ggtccgggtc acgctgcggc tggggagcc ccagcagctc   420

```
caggtccgct tccttcgtgc tgagggatac ccggtggacc tgtactacct tatggacctg    480
agctactcca tgaaggacga cctggaacgc gtgcgccagc tcgggcacgc tctgctggtc    540
cggctgcagg aagtcaccca ttctgtgcgc attggttttg gttcctttgt ggacaaaacg    600
gtgctgccct tgtgagcac agtaccctcc aaactcgcc accctgccc acccggctg        660 gagcgctgcc agtcaccatt cagctttcac catgtgctgt ccctgacggg ggacgcacaa    720
gccttcgagc gggaggtggg cgccagagt gtgtccggca atctggactc gcctgaaggt    780
ggcttcgatg ccattctgca ggctgcactc tgccaggagc agattggctg gagaaatgtg    840
tcccggctgc tggtgttcac ttcagacgac acattccata cagctgggga cgggaagttg    900
ggcggcattt tcatgcccag tgatgggcac tgccacttgg acagcaatgg cctctacagt    960
cgcagcacag agtttgacta cccttctgtg ggtcaggtag cccaggccct ctctgcagca    1020
aatatccagc ccatctttgc tgtcaccagt gccgcactgc ctgtctacca ggagctgagt    1080
aaactgattc ctaagtctgc agttggggag ctgagtgagg actccagcaa cgtggtacag    1140
ctcatcatgg atgcttataa tagcctgtct tccaccgtga cccttgaaca ctcttcactc    1200
cctcctgggg tccacatttc ttacgaatcc cagtgtgagg gtcctgagaa gagggagggt    1260
aaggctgagg atcgaggaca gtgcaaccac gtccgaatca accagacggt gactttctgg    1320
gtttctctcc aagccaccca ctgcctccca gagccccatc tcctgaggct ccgggccctt    1380
ggcttctcag aggagctgat tgtggagttg cacacgctgt gtgactgtaa ttgcagtgac    1440
acccagcccc aggctcccca ctgcagtgat ggccagggac acctacaatg tggtgtatgc    1500
agctgtgccc ctggccgcct aggtcggctc tgtgagtgct ctgtggcaga gctgtcctcc    1560
ccagacctgg aatctgggtg ccgggctccc aatggcacag gccctgtg cagtggaaag      1620 ggtcactgtc aatgtggacg ctgcagctgc agtggacaga gctctgggca tctgtgcgag    1680
tgtgacgatg ccagctgtga gcgacatgag ggcatcctct gcggaggctt tggtcgctgc    1740
caatgtggag tatgtcactg tcatgccaac cgcacgggca agcatgcga atgcagtggg    1800 gacatggaca gttgcatcag tcccgaggga gggctctgca gtgggcatgg acgctgcaaa    1860
tgcaaccgct gccagtgctt ggacggctac tatggtgctc tatgcgacca atgcccaggc    1920
tgcaagacac catgcgagag acaccgggac tgtgcagagt gtgggccctt caggactggc    1980
ccactggcca ccaactgcag tacagcttgt gcccatacca atgtgaccct ggccttggcc    2040
cctatcttgg atgatggctg gtgcaaagag cggaccctgg acaaccagct gttcttcttc    2100
ttggtggagg atgacgccag aggcacggtc gtgctcagag tgagaccccca agaaaaggga   2160 gcagaccaca cgcaggccat tgtgctgggc tgcgtagggg catcgtggc agtggggctg     2220 gggctggtcc tggcttaccg gctctcggtg gaaatctatg accgccggga atacagtcgc    2280
tttgagaagg agcagcaaca actcaactgg aagcaggaca gtaatcctct ctacaaaagt    2340
gccatcacga ccaccatcaa tcctcgcttt caagaggcag acagtcccac tctctga       2397
```

<210> SEQ ID NO 10
<211> LENGTH: 798
<212> TYPE: PRT
<213> ORGANISM: Homo sapiens

<400> SEQUENCE: 10

```
Met Val Ala Leu Pro Met Val Leu Val Leu Leu Val Leu Ser Arg
  1               5                  10                  15

Gly Glu Ser Glu Leu Asp Ala Lys Ile Pro Ser Thr Gly Asp Ala Thr
                 20                  25                  30
```

```
Glu Trp Arg Asn Pro His Leu Ser Met Leu Gly Ser Cys Gln Pro Ala
             35                  40                  45

Pro Ser Cys Gln Lys Cys Ile Leu Ser His Pro Ser Cys Ala Trp Cys
 50                  55                  60

Lys Gln Leu Asn Phe Thr Ala Ser Gly Glu Ala Glu Ala Arg Arg Cys
 65                  70                  75                  80

Ala Arg Arg Glu Glu Leu Leu Ala Arg Gly Cys Pro Leu Glu Glu Leu
                     85                  90                  95

Glu Glu Pro Arg Gly Gln Gln Glu Val Leu Gln Asp Gln Pro Leu Ser
             100                 105                 110

Gln Gly Ala Arg Gly Glu Gly Ala Thr Gln Leu Ala Pro Gln Arg Val
             115                 120                 125

Arg Val Thr Leu Arg Pro Gly Glu Pro Gln Gln Leu Gln Val Arg Phe
 130                 135                 140

Leu Arg Ala Glu Gly Tyr Pro Val Asp Leu Tyr Tyr Leu Met Asp Leu
145                 150                 155                 160

Ser Tyr Ser Met Lys Asp Asp Leu Glu Arg Val Arg Gln Leu Gly His
                 165                 170                 175

Ala Leu Leu Val Arg Leu Gln Glu Val Thr His Ser Val Arg Ile Gly
             180                 185                 190

Phe Gly Ser Phe Val Asp Lys Thr Val Leu Pro Phe Val Ser Thr Val
             195                 200                 205

Pro Ser Lys Leu Arg His Pro Cys Pro Thr Arg Leu Glu Arg Cys Gln
 210                 215                 220

Ser Pro Phe Ser Phe His His Val Leu Ser Leu Thr Gly Asp Ala Gln
225                 230                 235                 240

Ala Phe Glu Arg Glu Val Gly Arg Gln Ser Val Ser Gly Asn Leu Asp
                 245                 250                 255

Ser Pro Glu Gly Gly Phe Asp Ala Ile Leu Gln Ala Ala Leu Cys Gln
             260                 265                 270

Glu Gln Ile Gly Trp Arg Asn Val Ser Arg Leu Leu Val Phe Thr Ser
             275                 280                 285

Asp Asp Thr Phe His Thr Ala Gly Asp Gly Lys Leu Gly Gly Ile Phe
 290                 295                 300

Met Pro Ser Asp Gly His Cys His Leu Asp Ser Asn Gly Leu Tyr Ser
305                 310                 315                 320

Arg Ser Thr Glu Phe Asp Tyr Pro Ser Val Gly Gln Val Ala Gln Ala
                 325                 330                 335

Leu Ser Ala Ala Asn Ile Gln Pro Ile Phe Ala Val Thr Ser Ala Ala
             340                 345                 350

Leu Pro Val Tyr Gln Glu Leu Ser Lys Leu Ile Pro Lys Ser Ala Val
             355                 360                 365

Gly Glu Leu Ser Glu Asp Ser Ser Asn Val Val Gln Leu Ile Met Asp
 370                 375                 380

Ala Tyr Asn Ser Leu Ser Ser Thr Val Thr Leu Glu His Ser Ser Leu
385                 390                 395                 400

Pro Pro Gly Val His Ile Ser Tyr Glu Ser Gln Cys Glu Gly Pro Glu
                 405                 410                 415

Lys Arg Glu Gly Lys Ala Glu Asp Arg Gly Gln Cys Asn His Val Arg
             420                 425                 430

Ile Asn Gln Thr Val Thr Phe Trp Val Ser Leu Gln Ala Thr His Cys
             435                 440                 445
```

| | | | | | | | | | | | |
|---|---|---|---|---|---|---|---|---|---|---|---|
| Leu | Pro | Glu | Pro | His | Leu | Leu | Arg | Leu | Arg | Ala | Leu | Gly | Phe | Ser | Glu |
| 450 | | | | 455 | | | | 460 | | | |

Leu Pro Glu Pro His Leu Leu Arg Leu Arg Ala Leu Gly Phe Ser Glu
      450                 455                 460

Glu Leu Ile Val Glu Leu His Thr Leu Cys Asp Cys Asn Cys Ser Asp
465                 470                 475                 480

Thr Gln Pro Gln Ala Pro His Cys Ser Asp Gly Gln Gly His Leu Gln
                485                 490                 495

Cys Gly Val Cys Ser Cys Ala Pro Gly Arg Leu Gly Arg Leu Cys Glu
            500                 505                 510

Cys Ser Val Ala Glu Leu Ser Ser Pro Asp Leu Glu Ser Gly Cys Arg
                515                 520                 525

Ala Pro Asn Gly Thr Gly Pro Leu Cys Ser Gly Lys Gly His Cys Gln
530                 535                 540

Cys Gly Arg Cys Ser Cys Ser Gly Gln Ser Ser Gly His Leu Cys Glu
545                 550                 555                 560

Cys Asp Asp Ala Ser Cys Glu Arg His Glu Gly Ile Leu Cys Gly Gly
                565                 570                 575

Phe Gly Arg Cys Gln Cys Gly Val Cys His Cys His Ala Asn Arg Thr
            580                 585                 590

Gly Arg Ala Cys Glu Cys Ser Gly Asp Met Asp Ser Cys Ile Ser Pro
        595                 600                 605

Glu Gly Gly Leu Cys Ser Gly His Gly Arg Cys Lys Cys Asn Arg Cys
610                 615                 620

Gln Cys Leu Asp Gly Tyr Tyr Gly Ala Leu Cys Asp Gln Cys Pro Gly
625                 630                 635                 640

Cys Lys Thr Pro Cys Glu Arg His Arg Asp Cys Ala Glu Cys Gly Ala
                645                 650                 655

Phe Arg Thr Gly Pro Leu Ala Thr Asn Cys Ser Thr Ala Cys Ala His
                660                 665                 670

Thr Asn Val Thr Leu Ala Leu Ala Pro Ile Leu Asp Asp Gly Trp Cys
            675                 680                 685

Lys Glu Arg Thr Leu Asp Asn Gln Leu Phe Phe Phe Leu Val Glu Asp
        690                 695                 700

Asp Ala Arg Gly Thr Val Val Leu Arg Val Arg Pro Gln Glu Lys Gly
705                 710                 715                 720

Ala Asp His Thr Gln Ala Ile Val Leu Gly Cys Val Gly Gly Ile Val
                725                 730                 735

Ala Val Gly Leu Gly Leu Val Leu Ala Tyr Arg Leu Ser Val Glu Ile
            740                 745                 750

Tyr Asp Arg Arg Glu Tyr Ser Arg Phe Glu Lys Glu Gln Gln Gln Leu
        755                 760                 765

Asn Trp Lys Gln Asp Ser Asn Pro Leu Tyr Lys Ser Ala Ile Thr Thr
770                 775                 780

Thr Ile Asn Pro Arg Phe Gln Glu Ala Asp Ser Pro Thr Leu
785                 790                 795

<210> SEQ ID NO 11
<211> LENGTH: 2421
<212> TYPE: DNA
<213> ORGANISM: Mus musculus

<400> SEQUENCE: 11
atggtggatt catcaactgt tctcattttt ctgctggttc tgggcggagg tcagagtgag        60
ttagatacca agattacatc ctctggggag gccgcagaat gggaggatcc tgacctgtct       120
ctgcagggat cctgccagcc agttccttcc tgccagaagt gtattctctc acatcccagc       180

```
tgtgcatggt gcaaacaact gaacttcact gcctcgggag aggcagaggc gaggcgctgc    240
gcgcggcgag aggagctact ggctcgcggg tgccccgcgc aggagctaga ggagccgaga    300
ggccgccagg aggtgctgca ggacaagccg ctcagccagg agatcgcgg cgagggggcc     360 acccagctgg ccccgcagcg gatccgcgtc acgctgcgac caggggagcc ccagaaattc    420
cgggtccgct tcctccgagc tgcggggtac cccgtggacc tatattacct tatggacctg    480
agctactcaa tgaaggacga cttggaacgt gtgcgccagc tagggcatgc cctgctggtc    540
aggctgcagg aggtcacaca ttctgtgcgc ataggttttg gctccttcgt ggacaaaacg    600
gtgctgccct ttgtaagcac cgtgccctcc aagcttcacc acccatgccc cagccgactg    660
gagcgttgtc agccacccct cagctttcac cacgtgctgt ccctcaccgg ggacgctcaa    720
gccttcgaga gagaggtggg acgcagaat gtctctggca acctggactc acccgaaggc     780
ggctttgatg ccattttgca ggctgccctc tgccaggaac agattggctg gagaaatgtc    840
tcccgtcttc tagtgttcac ttcagacgat acattccaca cagctgggga tgggaaactg    900
ggtggcattt tcatgcccag cgacgggcgg tgccatctgg acagcaatgg tgtctacacg    960
aacagcgcag agtttgacta tccctctgtg ggtcaagtag cccaggccct cactgcagcg   1020
aatatccaac ctatctttgc tgtcaccggt gcaacactgc ctgtgtatca ggagctgaga   1080
cagttgattc ccaagtctgc tgtcggggag ctgagtgagg actccagcaa tgtggtgcag   1140
ctcatcatgg atgcttatga tagcctgtca tccactgtga ctcttgagca ctctccactc   1200
ccaccaggag tcagcatctc ctttgaatct cactgtaagg gtcctgagaa gacggagggt   1260
gaggctgggg accggggaca gtgcaatgat gtccgagtca accagacggt ggatttctgg   1320
gtcactcttc aagctactca ctgcctccca gaagcccacg tcctacgact ctgggctctt   1380
ggcttctcag aggagttaac tgtggagctg cacacagtgt gcgactgtaa ctgtggtgat   1440
gcccagcctc acgctcccta ctgcagtgat ggacagggg accttcagtg cgggatatgc    1500
agctgtgccc ctggccgtct tggtcagctg tgtgaatgct ctgaggctga cctgtcctcc   1560
ccagatttgg aatctggttg ccgggcccca aacgggacag ggcccctatg cagcgggaag   1620
ggtcgatgcc aatgtggacg ctgcagctgc agtgggcaga gctctgggcg tctgtgcgag   1680
tgtgatgatg ccagctgtga gcgacatgag ggcatcctct gtggaggctt tggccactgc   1740
cagtgtggag tatgtcactg tcacgccaac cacaccggca gagcttgcga gtgcagcaag   1800
agtgtagaca gctgtgtcag tcctgaagga gggctctgca gtgggcacgg atactgcaaa   1860
tgcaaccgtt gccagtgcct ggatggctac tacggggctc tgtgtgacca gtgcctaggc   1920
tgcaagtcac catgtgagca gtacaggga  tgtgcagagt gcgggcatt tggtaccggt   1980 cccctggcag ccaactgtag tgtggtctgt gctgacgtga atgtgacctt gaccttggcc   2040
cctaacttgg atgatggctg gtgcaaagaa aggacaatag acaaccagct gttcttcttc   2100
ctggtggagc atgcagccag cgggatcgta ctgagagtga cccccaaga gaagggagtg    2160 gatcacaccc gtgccatcat actgggctgc acaggggca tcgtggcagt gggactaggg    2220
ctggttctgg cttaccggct ctctgtggaa atctacgacc gacgggagta caggcgcttt   2280
gagaaggagc agcagcaact caactggaag caggacaaca atcctctcta caaaagtgcg   2340
atcacaacca ctgtcaaccc ccgcttccaa gggacaaacg gtcggtcgcc atccctctct   2400
ctgaccaggg aagcagactg a                                             2421
```

<210> SEQ ID NO 12

```
<211> LENGTH: 806
<212> TYPE: PRT
<213> ORGANISM: Mus musculus

<400> SEQUENCE: 12
```

| | | | | | | | | | | | | | | | |
|---|---|---|---|---|---|---|---|---|---|---|---|---|---|---|---|
| Met | Val | Asp | Ser | Ser | Thr | Val | Leu | Ile | Phe | Leu | Leu | Val | Leu | Gly | Gly |
| 1 | | | | 5 | | | | | 10 | | | | | 15 | |
| Gly | Gln | Ser | Glu | Leu | Asp | Thr | Lys | Ile | Thr | Ser | Ser | Gly | Glu | Ala | Ala |
| | | | 20 | | | | | 25 | | | | | 30 | | |
| Glu | Trp | Glu | Asp | Pro | Asp | Leu | Ser | Leu | Gln | Gly | Ser | Cys | Gln | Pro | Val |
| | | 35 | | | | | 40 | | | | | 45 | | | |
| Pro | Ser | Cys | Gln | Lys | Cys | Ile | Leu | Ser | His | Pro | Ser | Cys | Ala | Trp | Cys |
| | 50 | | | | | 55 | | | | | 60 | | | | |
| Lys | Gln | Leu | Asn | Phe | Thr | Ala | Ser | Gly | Glu | Ala | Glu | Ala | Arg | Arg | Cys |
| 65 | | | | | 70 | | | | | 75 | | | | | 80 |
| Ala | Arg | Arg | Glu | Glu | Leu | Leu | Ala | Arg | Gly | Cys | Pro | Ala | Gln | Glu | Leu |
| | | | | 85 | | | | | 90 | | | | | 95 | |
| Glu | Glu | Pro | Arg | Gly | Arg | Gln | Glu | Val | Leu | Gln | Asp | Lys | Pro | Leu | Ser |
| | | | 100 | | | | | 105 | | | | | 110 | | |
| Gln | Gly | Asp | Arg | Gly | Glu | Gly | Ala | Thr | Gln | Leu | Ala | Pro | Gln | Arg | Ile |
| | | | 115 | | | | | 120 | | | | | 125 | | |
| Arg | Val | Thr | Leu | Arg | Pro | Gly | Glu | Pro | Gln | Lys | Phe | Arg | Val | Arg | Phe |
| | | 130 | | | | | 135 | | | | | 140 | | | |
| Leu | Arg | Ala | Ala | Gly | Tyr | Pro | Val | Asp | Leu | Tyr | Tyr | Leu | Met | Asp | Leu |
| 145 | | | | | 150 | | | | | 155 | | | | | 160 |
| Ser | Tyr | Ser | Met | Lys | Asp | Asp | Leu | Glu | Arg | Val | Arg | Gln | Leu | Gly | His |
| | | | | 165 | | | | | 170 | | | | | 175 | |
| Ala | Leu | Leu | Val | Arg | Leu | Gln | Glu | Val | Thr | His | Ser | Val | Arg | Ile | Gly |
| | | | 180 | | | | | 185 | | | | | 190 | | |
| Phe | Gly | Ser | Phe | Val | Asp | Lys | Thr | Val | Leu | Pro | Phe | Val | Ser | Thr | Val |
| | | | 195 | | | | | 200 | | | | | 205 | | |
| Pro | Ser | Lys | Leu | His | His | Pro | Cys | Pro | Ser | Arg | Leu | Glu | Arg | Cys | Gln |
| | | 210 | | | | | 215 | | | | | 220 | | | |
| Pro | Pro | Phe | Ser | Phe | His | His | Val | Leu | Ser | Leu | Thr | Gly | Asp | Ala | Gln |
| 225 | | | | | 230 | | | | | 235 | | | | | 240 |
| Ala | Phe | Glu | Arg | Glu | Val | Gly | Arg | Gln | Asn | Val | Ser | Gly | Asn | Leu | Asp |
| | | | | 245 | | | | | 250 | | | | | 255 | |
| Ser | Pro | Glu | Gly | Gly | Phe | Asp | Ala | Ile | Leu | Gln | Ala | Ala | Leu | Cys | Gln |
| | | | 260 | | | | | 265 | | | | | 270 | | |
| Glu | Gln | Ile | Gly | Trp | Arg | Asn | Val | Ser | Arg | Leu | Leu | Val | Phe | Thr | Ser |
| | | | 275 | | | | | 280 | | | | | 285 | | |
| Asp | Asp | Thr | Phe | His | Thr | Ala | Gly | Asp | Gly | Lys | Leu | Gly | Gly | Ile | Phe |
| | | 290 | | | | | 295 | | | | | 300 | | | |
| Met | Pro | Ser | Asp | Gly | Arg | Cys | His | Leu | Asp | Ser | Asn | Gly | Val | Tyr | Thr |
| 305 | | | | | 310 | | | | | 315 | | | | | 320 |
| Asn | Ser | Ala | Glu | Phe | Asp | Tyr | Pro | Ser | Val | Gly | Gln | Val | Ala | Gln | Ala |
| | | | | 325 | | | | | 330 | | | | | 335 | |
| Leu | Thr | Ala | Ala | Asn | Ile | Gln | Pro | Ile | Phe | Ala | Val | Thr | Gly | Ala | Thr |
| | | | 340 | | | | | 345 | | | | | 350 | | |
| Leu | Pro | Val | Tyr | Gln | Glu | Leu | Arg | Gln | Leu | Ile | Pro | Lys | Ser | Ala | Val |
| | | | 355 | | | | | 360 | | | | | 365 | | |
| Gly | Glu | Leu | Ser | Glu | Asp | Ser | Ser | Asn | Val | Val | Gln | Leu | Ile | Met | Asp |
| | | 370 | | | | | 375 | | | | | 380 | | | |
| Ala | Tyr | Asp | Ser | Leu | Ser | Ser | Thr | Val | Thr | Leu | Glu | His | Ser | Pro | Leu |

-continued

```
            385                 390                 395                 400
Pro Pro Gly Val Ser Ile Ser Phe Glu Ser His Cys Lys Gly Pro Glu
                405                 410                 415
Lys Thr Glu Gly Glu Ala Gly Asp Arg Gly Gln Cys Asn Asp Val Arg
                420                 425                 430
Val Asn Gln Thr Val Asp Phe Trp Val Thr Leu Gln Ala Thr His Cys
                435                 440                 445
Leu Pro Glu Ala His Val Leu Arg Leu Trp Ala Leu Gly Phe Ser Glu
                450                 455                 460
Glu Leu Thr Val Glu Leu His Thr Val Cys Asp Cys Asn Cys Gly Asp
465                 470                 475                 480
Ala Gln Pro His Ala Pro Tyr Cys Ser Asp Gly Gln Gly Asp Leu Gln
                485                 490                 495
Cys Gly Ile Cys Ser Cys Ala Pro Gly Arg Leu Gly Gln Leu Cys Glu
                500                 505                 510
Cys Ser Glu Ala Asp Leu Ser Ser Pro Asp Leu Glu Ser Gly Cys Arg
                515                 520                 525
Ala Pro Asn Gly Thr Gly Pro Leu Cys Ser Gly Lys Gly Arg Cys Gln
530                 535                 540
Cys Gly Arg Cys Ser Cys Ser Gly Gln Ser Ser Gly Arg Leu Cys Glu
545                 550                 555                 560
Cys Asp Asp Ala Ser Cys Glu Arg His Glu Gly Ile Leu Cys Gly Gly
                565                 570                 575
Phe Gly His Cys Gln Cys Gly Val Cys His Cys His Ala Asn His Thr
                580                 585                 590
Gly Arg Ala Cys Glu Cys Ser Lys Ser Val Asp Ser Cys Val Ser Pro
                595                 600                 605
Glu Gly Gly Leu Cys Ser Gly His Gly Tyr Cys Lys Cys Asn Arg Cys
                610                 615                 620
Gln Cys Leu Asp Gly Tyr Tyr Gly Ala Leu Cys Asp Gln Cys Leu Gly
625                 630                 635                 640
Cys Lys Ser Pro Cys Glu Gln Tyr Arg Asp Cys Ala Glu Cys Gly Ala
                645                 650                 655
Phe Gly Thr Gly Pro Leu Ala Ala Asn Cys Ser Val Val Cys Ala Asp
                660                 665                 670
Val Asn Val Thr Leu Thr Leu Ala Pro Asn Leu Asp Asp Gly Trp Cys
                675                 680                 685
Lys Glu Arg Thr Ile Asp Asn Gln Leu Phe Phe Leu Val Glu His
                690                 695                 700
Ala Ala Ser Gly Ile Val Leu Arg Val Arg Pro Gln Glu Lys Gly Val
705                 710                 715                 720
Asp His Thr Arg Ala Ile Ile Leu Gly Cys Thr Gly Gly Ile Val Ala
                725                 730                 735
Val Gly Leu Gly Leu Val Leu Ala Tyr Arg Leu Ser Val Glu Ile Tyr
                740                 745                 750
Asp Arg Arg Glu Tyr Arg Arg Phe Glu Lys Glu Gln Gln Gln Leu Asn
                755                 760                 765
Trp Lys Gln Asp Asn Asn Pro Leu Tyr Lys Ser Ala Ile Thr Thr Thr
                770                 775                 780
Val Asn Pro Arg Phe Gln Gly Thr Asn Gly Arg Ser Pro Ser Leu Ser
785                 790                 795                 800
Leu Thr Arg Glu Ala Asp
                805
```

<210> SEQ ID NO 13
<211> LENGTH: 1173
<212> TYPE: DNA
<213> ORGANISM: Homo sapiens

<400> SEQUENCE: 13

```
atgccgccct ccgggctgcg gctgctgccg ctgctgctac cgctgctgtg gctactggtg      60
ctgacgcctg gccggccggc cgcgggacta tccacctgca agactatcga catggagctg     120
gtgaagcgga agcgcatcga ggccatccgc ggccagatcc tgtccaagct gcggctcgcc     180
agccccccga gccaggggga ggtgccgccc ggcccgctgc cgaggccgt gctcgccctg     240
tacaacagca cccgcgaccg ggtggccggg agagtgcag accggagcc cgagcctgag     300
gccgactact acgccaagga ggtcaccgc gtgctaatgg tggaaaccca caacgaaatc     360
tatgacaagt tcaagcagag tacacacagc atatatatgt tcttcaacac atcagagctc     420
cgagaagcgg tacctgaacc cgtgttgctc tcccgggcag agctgcgtct gctgaggctc     480
aagttaaaag tggagcagca cgtggagctg taccagaaat acagcaacaa ttcctggcga     540
tacctcagca accggctgct ggcacccagc gactcgccag agtggttatc ttttgatgtc     600
accggagttg tgcggcagtg gttgagccgt ggaggggaaa ttgagggctt tcgccttagc     660
gcccactgct cctgtgacag cagggataac acactgcaag tggacatcaa cgggttcact     720
accggccgcc gaggtgacct ggccaccatt catggcatga accggccttt cctgcttctc     780
atggccaccc cgctggagag ggcccagcat ctgcaaagct cccggcaccg ccgagccctg     840
gacaccaact attgcttcag ctccacggag aagaactgct gcgtgcggca gctgtacatt     900
gacttccgca aggacctcgg ctggaagtgg atccacgagc caagggcta ccatgccaac     960
ttctgcctcg ggccctgccc ctacatttgg agcctggaca cgcagtacag caaggtcctg    1020
gccctgtaca accagcataa cccgggcgcc tcggcggcgc cgtgctgcgt gccgcaggcg    1080
ctggagccgc tgcccatcgt gtactacgtg ggccgcaagc ccaaggtgga gcagctgtcc    1140
aacatgatcg tgcgctcctg caagtgcagc tga                                 1173
```

<210> SEQ ID NO 14
<211> LENGTH: 390
<212> TYPE: PRT
<213> ORGANISM: Homo sapiens

<400> SEQUENCE: 14

```
Met Pro Pro Ser Gly Leu Arg Leu Leu Pro Leu Leu Pro Leu Leu
 1               5                  10                  15

Trp Leu Leu Val Leu Thr Pro Gly Arg Pro Ala Ala Gly Leu Ser Thr
                20                  25                  30

Cys Lys Thr Ile Asp Met Glu Leu Val Lys Arg Lys Arg Ile Glu Ala
                35                  40                  45

Ile Arg Gly Gln Ile Leu Ser Lys Leu Arg Leu Ala Ser Pro Pro Ser
        50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
                100                 105                 110

Met Val Glu Thr His Asn Glu Ile Tyr Asp Lys Phe Lys Gln Ser Thr
```

```
                    115                 120                 125
His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390
```

<210> SEQ ID NO 15
<211> LENGTH: 489
<212> TYPE: DNA
<213> ORGANISM: Homo sapiens

<400> SEQUENCE: 15

```
atgagatcca gtcctggcaa catggagagg attgtcatct gtctgatggt catcttcttg      60
gggacactgg tccacaaatc aagctcccaa ggtcaagatc gccacatgat tagaatgcgt     120
caacttatag atattgttga tcagctgaaa aattatgtga atgacttggt ccctgaattt     180
ctgccagctc cagaagatgt agagacaaac tgtgagtggt cagcttttc ctgctttcag      240 aaggcccaac taaagtcagc aaatacagga acaatgaaa ggataatcaa tgtatcaatt      300
aaaaagctga gaggaaacc accttccaca atgcaggga gaagcagaa acacagacta       360 acatgccctt catgtgattc ttatgagaaa aaaccaccca agaattcct agaaagattc       420 aaatcacttc tccaaaagat gattcatcag catctgtcct ctagaacaca cggaagtgaa      480
gattcctga                                                              489
```

<210> SEQ ID NO 16
<211> LENGTH: 162
<212> TYPE: PRT
<213> ORGANISM: Homo sapiens

<400> SEQUENCE: 16

Met Arg Ser Ser Pro Gly Asn Met Glu Arg Ile Val Ile Cys Leu Met
1               5                   10                  15

Val Ile Phe Leu Gly Thr Leu Val His Lys Ser Ser Gln Gly Gln
            20                  25                  30

Asp Arg His Met Ile Arg Met Arg Gln Leu Ile Asp Ile Val Asp Gln
        35                  40                  45

Leu Lys Asn Tyr Val Asn Asp Leu Val Pro Glu Phe Leu Pro Ala Pro
    50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
            100                 105                 110

Gly Arg Arg Gln Lys His Arg Leu Thr Cys Pro Ser Cys Asp Ser Tyr
        115                 120                 125

Glu Lys Lys Pro Pro Lys Glu Phe Leu Glu Arg Phe Lys Ser Leu Leu
    130                 135                 140

Gln Lys Met Ile His Gln His Leu Ser Ser Arg Thr His Gly Ser Glu
145                 150                 155                 160

Asp Ser

<210> SEQ ID NO 17
<211> LENGTH: 462
<212> TYPE: DNA
<213> ORGANISM: Homo sapiens

<400> SEQUENCE: 17
atgagatcca gtcctggcaa catggagagg attgtcatct gtctgatggt catcttcttg     60
gggacactgg tccacaaatc aagctcccaa ggtcaagatc gccacatgat tagaatgcgt    120
caacttatag atattgttga tcagctgaaa aattatgtga atgacttggt ccctgaattt    180
ctgccagctc cagaagatgt agagacaaac tgtgagtggt cagcttttc ctgctttcag    240 aaggcccaac taaagtcagc aaatacagga acaatgaaa ggataatcaa tgtatcaatt    300
aaaaagctga agaggaaacc accttccaca aatgcaggga agacagaa acacagacta    360 acatgccctt catgtgattc ttatgagaaa aaaccaccca agaattcct agaaagattc    420 aaatcacttc tccaaaaggt atctacctta agtttcattt ga                      462

<210> SEQ ID NO 18
<211> LENGTH: 153
<212> TYPE: PRT
<213> ORGANISM: Homo sapiens

<400> SEQUENCE: 18

Met Arg Ser Ser Pro Gly Asn Met Glu Arg Ile Val Ile Cys Leu Met
1               5                   10                  15

Val Ile Phe Leu Gly Thr Leu Val His Lys Ser Ser Gln Gly Gln
            20                  25                  30

Asp Arg His Met Ile Arg Met Arg Gln Leu Ile Asp Ile Val Asp Gln

```
                35                  40                  45
Leu Lys Asn Tyr Val Asn Asp Leu Val Pro Glu Phe Leu Pro Ala Pro
 50                  55                  60

Glu Asp Val Glu Thr Asn Cys Glu Trp Ser Ala Phe Ser Cys Phe Gln
 65                  70                  75                  80

Lys Ala Gln Leu Lys Ser Ala Asn Thr Gly Asn Glu Arg Ile Ile
                 85                  90                  95

Asn Val Ser Ile Lys Lys Leu Lys Arg Lys Pro Pro Ser Thr Asn Ala
                100                 105                 110

Gly Arg Arg Gln Lys His Arg Leu Thr Cys Pro Ser Cys Asp Ser Tyr
                115                 120                 125

Glu Lys Lys Pro Pro Lys Glu Phe Leu Glu Arg Phe Lys Ser Leu Leu
130                 135                 140

Gln Lys Val Ser Thr Leu Ser Phe Ile
145                 150

<210> SEQ ID NO 19
<211> LENGTH: 639
<212> TYPE: DNA
<213> ORGANISM: Homo sapiens

<400> SEQUENCE: 19
atgaactcct tctccacaag cgccttcggt ccagttgcct ctccctggg gctgctcctg      60 gtgttgcctg ctgccttccc tgccccagta cccccaggag aagattccaa agatgtagcc    120
gccccacaca gacagccact cacctcttca gaacgaattg acaaacaaat tcggtacatc    180
ctcgacggca tctcagccct gagaaaggag acatgtaaca gagtaacat gtgtgaaagc    240 agcaaagagg cactggcaga aaacaacctg aaccttccaa agatggctga aaaagatgga    300
tgcttccaat ctggattcaa tgaggagact tgcctggtga aaatcatcac tggtctttg     360 gagtttgagg tatacctaga gtacctccag aacagatttg agagtagtga ggaacaagcc    420
agagctgtgc agatgagtac aaaagtcctg atccagttcc tgcagaaaaa ggcaaagaat    480
ctagatgcaa taaccacccc tgacccaacc acaaatgcca gcctgctgac gaagctgcag    540
gcacagaacc agtggctgca ggacatgaca actcatctca ttctgcgcag ctttaaggag    600
ttcctgcagt ccagcctgag ggctcttcgg caaatgtag                           639

<210> SEQ ID NO 20
<211> LENGTH: 212
<212> TYPE: PRT
<213> ORGANISM: Homo sapiens

<400> SEQUENCE: 20

Met Asn Ser Phe Ser Thr Ser Ala Phe Gly Pro Val Ala Phe Ser Leu
  1               5                  10                  15

Gly Leu Leu Leu Val Leu Pro Ala Ala Phe Pro Ala Pro Val Pro Pro
                 20                  25                  30

Gly Glu Asp Ser Lys Asp Val Ala Ala Pro His Arg Gln Pro Leu Thr
                 35                  40                  45

Ser Ser Glu Arg Ile Asp Lys Gln Ile Arg Tyr Ile Leu Asp Gly Ile
 50                  55                  60

Ser Ala Leu Arg Lys Glu Thr Cys Asn Lys Ser Asn Met Cys Glu Ser
 65                  70                  75                  80

Ser Lys Glu Ala Leu Ala Glu Asn Asn Leu Asn Leu Pro Lys Met Ala
                 85                  90                  95
```

```
Glu Lys Asp Gly Cys Phe Gln Ser Gly Phe Asn Glu Glu Thr Cys Leu
                100                 105                 110
Val Lys Ile Ile Thr Gly Leu Leu Glu Phe Glu Val Tyr Leu Glu Tyr
            115                 120                 125
Leu Gln Asn Arg Phe Glu Ser Ser Glu Glu Gln Ala Arg Ala Val Gln
        130                 135                 140
Met Ser Thr Lys Val Leu Ile Gln Phe Leu Gln Lys Lys Ala Lys Asn
145                 150                 155                 160
Leu Asp Ala Ile Thr Thr Pro Asp Pro Thr Thr Asn Ala Ser Leu Leu
                165                 170                 175
Thr Lys Leu Gln Ala Gln Asn Gln Trp Leu Gln Asp Met Thr Thr His
            180                 185                 190
Leu Ile Leu Arg Ser Phe Lys Glu Phe Leu Gln Ser Ser Leu Arg Ala
        195                 200                 205
Leu Arg Gln Met
    210
```

<210> SEQ ID NO 21
<211> LENGTH: 732
<212> TYPE: DNA
<213> ORGANISM: Homo sapiens

<400> SEQUENCE: 21

```
atgggccaga cggcaggcga ccttggctgg cggctcagcc tgttgctgct tcccttgctc      60
ctggttcaag ctggtgtctg gggattccca aggcccccag gaggccccca gctgagcctg     120
caggagctgc ggagggagtt cacagtcagc ctgcatctcg ccaggaagct gctctccgag     180
gttcggggcc aggcccaccg ctttgcggaa tctcacctgc caggagtgaa cctgtacctc     240
ctgcccctgg gagagcagct ccctgatgtt tccctgacct tccaggcctg cgccgcctc      300
tctgacccgg agcgtctctg cttcatctcc accacgcttc agcccttcca tgccctgctg     360
ggagggctgg ggacccaggg ccgctggacc aacatggaga ggatgcagct gtgggccatg     420
aggctggacc tccgcgatct gcagcggcac ctccgcttcc aggtgctggc tgcaggattc     480
aacctcccgg aggaggagga ggaggaagag gaggaggagg aggaggagag gaaggggctg     540
ctcccagggg cactgggcag cgccttacag ggcccggccc aggtgtcctg gccccagctc     600
ctctccacct accgcctgct gcactccttg gagctcgtct atctcgggc cgtgcgggag      660
ttgctgctgc tgtccaaggc tgggcactca gtctggccct tggggttccc aacattgagc     720
ccccagccct ga                                                         732
```

<210> SEQ ID NO 22
<211> LENGTH: 243
<212> TYPE: PRT
<213> ORGANISM: Homo sapiens

<400> SEQUENCE: 22

```
Met Gly Gln Thr Ala Gly Asp Leu Gly Trp Arg Leu Ser Leu Leu Leu
1               5                   10                  15
Leu Pro Leu Leu Leu Val Gln Ala Gly Val Trp Gly Phe Pro Arg Pro
            20                  25                  30
Pro Gly Arg Pro Gln Leu Ser Leu Gln Glu Leu Arg Arg Glu Phe Thr
        35                  40                  45
Val Ser Leu His Leu Ala Arg Lys Leu Leu Ser Glu Val Arg Gly Gln
    50                  55                  60
Ala His Arg Phe Ala Glu Ser His Leu Pro Gly Val Asn Leu Tyr Leu
```

```
                65                  70                  75                  80
Leu Pro Leu Gly Glu Gln Leu Pro Asp Val Ser Leu Thr Phe Gln Ala
                    85                  90                  95

Trp Arg Arg Leu Ser Asp Pro Glu Arg Leu Cys Phe Ile Ser Thr Thr
                100                 105                 110

Leu Gln Pro Phe His Ala Leu Leu Gly Gly Leu Gly Thr Gln Gly Arg
            115                 120                 125

Trp Thr Asn Met Glu Arg Met Gln Leu Trp Ala Met Arg Leu Asp Leu
        130                 135                 140

Arg Asp Leu Gln Arg His Leu Arg Phe Gln Val Leu Ala Ala Gly Phe
145                 150                 155                 160

Asn Leu Pro Glu Glu Glu Glu Glu Glu Glu Glu Glu Glu Glu Glu Glu
                165                 170                 175

Arg Lys Gly Leu Leu Pro Gly Ala Leu Gly Ser Ala Leu Gln Gly Pro
                180                 185                 190

Ala Gln Val Ser Trp Pro Gln Leu Leu Ser Thr Tyr Arg Leu Leu His
            195                 200                 205

Ser Leu Glu Leu Val Leu Ser Arg Ala Val Arg Glu Leu Leu Leu Leu
        210                 215                 220

Ser Lys Ala Gly His Ser Val Trp Pro Leu Gly Phe Pro Thr Leu Ser
225                 230                 235                 240

Pro Gln Pro

<210> SEQ ID NO 23
<211> LENGTH: 690
<212> TYPE: DNA
<213> ORGANISM: Homo sapiens

<400> SEQUENCE: 23
atgaccccgc agcttctcct ggcccttgtc ctctgggcca gctgcccgcc ctgcagtgga      60
aggaaagggc ccccagcagc tctgacactg cccgggtgc aatgccgagc ctctcggtac     120
ccgatcgccg tggattgctc ctggaccctg ccgcctgctc caaactccac cagccccgtg    180
tccttcattg ccacgtacag gctcggcatg gctgcccggg ccacagctg ccctgcctg      240 cagcagacgc caacgtccac cagctgcacc atcacggatg tccagctgtt ctccatggct    300
ccctacgtgc tcaatgtcac cgccgtccac ccctgggggct ccagcagcag cttcgtgcct   360
ttcataacag agcacatcat caagcccgac cctccagaag gcgtgcgcct aagccccctc    420
gctgagcgcc agctacaggt gcagtgggag cctcccgggt cctggccctt cccagagatc    480
ttctcactga gtactggat ccgttacaag cgtcaggag ctgcgcgctt ccaccgggtg      540
gggcccattg aagccacgtc cttcatcctc agggctgtgc ggccccgagc caggtactac    600
gtccaagtgg cggctcagga cctcacagac tacggggaac tgagtgactg gagtctcccc    660
gccactgcca caatgagcct gggcaagtag                                     690

<210> SEQ ID NO 24
<211> LENGTH: 229
<212> TYPE: PRT
<213> ORGANISM: Homo sapiens

<400> SEQUENCE: 24

Met Thr Pro Gln Leu Leu Leu Ala Leu Val Leu Trp Ala Ser Cys Pro
1               5                   10                  15

Pro Cys Ser Gly Arg Lys Gly Pro Pro Ala Ala Leu Thr Leu Pro Arg
            20                  25                  30
```

```
Val Gln Cys Arg Ala Ser Arg Tyr Pro Ile Ala Val Asp Cys Ser Trp
             35                  40                  45

Thr Leu Pro Pro Ala Pro Asn Ser Thr Ser Pro Val Ser Phe Ile Ala
     50                  55                  60

Thr Tyr Arg Leu Gly Met Ala Ala Arg Gly His Ser Trp Pro Cys Leu
 65                  70                  75                  80

Gln Gln Thr Pro Thr Ser Thr Ser Cys Thr Ile Thr Asp Val Gln Leu
                 85                  90                  95

Phe Ser Met Ala Pro Tyr Val Leu Asn Val Thr Ala Val His Pro Trp
            100                 105                 110

Gly Ser Ser Ser Phe Val Pro Phe Ile Thr Glu His Ile Ile Lys
            115                 120                 125

Pro Asp Pro Pro Glu Gly Val Arg Leu Ser Pro Leu Ala Glu Arg Gln
        130                 135                 140

Leu Gln Val Gln Trp Glu Pro Pro Gly Ser Trp Pro Phe Pro Glu Ile
145                 150                 155                 160

Phe Ser Leu Lys Tyr Trp Ile Arg Tyr Lys Arg Gln Gly Ala Ala Arg
                165                 170                 175

Phe His Arg Val Gly Pro Ile Glu Ala Thr Ser Phe Ile Leu Arg Ala
            180                 185                 190

Val Arg Pro Arg Ala Arg Tyr Tyr Val Gln Val Ala Ala Gln Asp Leu
        195                 200                 205

Thr Asp Tyr Gly Glu Leu Ser Asp Trp Ser Leu Pro Ala Thr Ala Thr
    210                 215                 220

Met Ser Leu Gly Lys
225

<210> SEQ ID NO 25
<211> LENGTH: 462
<212> TYPE: DNA
<213> ORGANISM: Homo sapiens

<400> SEQUENCE: 25
atgtacagga tgcaactcct gtcttgcatt gcactaagtc ttgcacttgt cacaaacagt      60
gcacctactt caagttctac aaagaaaaca cagctacaac tggagcattt actgctggat     120
ttacagatga ttttgaatgg aattaataat tacaagaatc ccaaactcac caggatgctc     180
acatttaagt tttacatgcc aagaaggcc acagaactga acatcttca gtgtctagaa       240 gaagaactca aacctctgga ggaagtgcta aatttagctc aaagcaaaaa ctttcactta     300
agacccaggg acttaatcag caatatcaac gtaatagttc tggaactaaa gggatctgaa     360
acaacattca tgtgtgaata tgctgatgag acagcaacca ttgtagaatt tctgaacaga     420
tggattacct tttgtcaaag catcatctca acactgactt ga                       462

<210> SEQ ID NO 26
<211> LENGTH: 153
<212> TYPE: PRT
<213> ORGANISM: Homo sapiens

<400> SEQUENCE: 26

Met Tyr Arg Met Gln Leu Leu Ser Cys Ile Ala Leu Ser Leu Ala Leu
  1               5                  10                  15

Val Thr Asn Ser Ala Pro Thr Ser Ser Ser Thr Lys Lys Thr Gln Leu
             20                  25                  30

Gln Leu Glu His Leu Leu Leu Asp Leu Gln Met Ile Leu Asn Gly Ile
```

-continued

```
                35                  40                  45
Asn Asn Tyr Lys Asn Pro Lys Leu Thr Arg Met Leu Thr Phe Lys Phe
        50                  55                  60

Tyr Met Pro Lys Lys Ala Thr Glu Leu Lys His Leu Gln Cys Leu Glu
65              70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
        130                 135                 140

Cys Gln Ser Ile Ile Ser Thr Leu Thr
145                 150
```

GPR15-MEDIATED HOMING AND USES THEREOF

CROSS REFERENCE TO RELATED APPLICATION

This application claims priority under 35 USC §119(e) from U.S Provisional Application Ser. No. 61/807,484, filed Apr. 2, 2013, which application is herein specifically incorporated by reference in its entirety.

GOVERNMENTAL SUPPORT

The research leading to the present invention was funded in part by NIH/NCI grant 5P30CA016087-32, NIH/NCRR grant UL1RR029893, and NIH/NCI P30 CA016087-30. The United States government has certain rights in the invention.

FIELD OF THE INVENTION

The present invention relates to T cells that migrate or home specifically to the large intestine and methods for generating same. T cells having such exquisite organ targeting specificity may be regulatory T (Treg) cells or effector/conventional T (Teff) cells. More specifically, the invention relates to in vitro methods directed to promoting expression of G-protein coupled receptor 15 (GPR15; also known as BOB) on T cells, populations of GPR15+ enriched T cells generated using these methods, and methods for using GPR15+ enriched T cell populations generated using the methods described herein. With respect to Treg cells having enhanced expression of GPR15, such cells can be used in immunotherapy and for the suppression of autoimmune responses. With respect to Teff cells having enhanced expression of GPR15, such cells can be used in immunotherapy and for the enhancement of immune responses against, for example, cancers or infections of the large intestine. GPR15+ enriched Treg or Teff cells made in accordance with methods described herein and/or compositions thereof for use in treating an autoimmune and/or inflammatory disorder of the large intestine (Treg cells) or a cancer or an infection of the large intestine (Teff cells) is also encompassed herein. Use of GPR15+ enriched Treg or Teff cells made in accordance with methods described herein and/or compositions thereof in the preparation of a medicament for treating an autoimmune and/or inflammatory disorder of the large intestine (Treg cells) or a cancer or an infection of the large intestine (Teff cells) is also encompassed herein. Also encompassed herein are methods for screening to identify modulators of GRP15 expression.

BACKGROUND OF THE INVENTION

Several publications and patent documents are referenced in this application in order to more fully describe the state of the art to which this invention pertains. The disclosure of each of these publications and documents is incorporated by reference herein.

The human gut harbors an enormous number of bacteria, which have coevolved with the host and play important roles in the development of the immune system (1), resistance to intestinal infection (2), and nutrient metabolism and absorption (3). The coexistence of host and microbiota is due in large part to the equilibrium established between the host immune system and microbiota (4) through a variety of mechanisms (5). In the gastrointestinal tract, the large intestine harbors significantly more microbiota ($10^{10}$-$10^{12}$ bacteria per gram of feces) than the small intestine ($10^5$-$10^7$ bacteria per gram of feces) (6) and contains higher frequencies of FOXP3+ regulatory T cells (Treg), of which at least some have T cell antigen receptors (TCRs) specific for microbial antigens (7-9). Disruption of the equilibrium between the host immune system and microbiota can trigger inflammatory bowel disease in mouse models and, in humans, likely contributes to Crohn's disease and ulcerative colitis (10), in which the large intestine is the primary site of inflammation. While T cell responses have critical roles in inflammatory bowel diseases (10), it remains unclear how T cells migrate to the large intestine (11-13). Lymphocyte migration to the small intestine is dependent on retinoic acid-mediated induction of integrin α4β7 and CCR9 (14, 15). In addition, retinoic acid together with TGFβ induces the extrathymic differentiation of FOXP3+ Treg cells (16-19), which are essential for oral tolerance to food antigens (20). Retinoic acid is not, however, sufficient to induce T cell migration to the large intestine (11, 12), indicating that there is a separate mechanism for this process.

SUMMARY OF INVENTION

The large intestine is the site most commonly affected in inflammatory bowel disease. Lymphocyte homing, which contributes to inflammation, has been studied extensively in the small intestine, but there is little known about homing to the large intestine. The present inventors demonstrate herein that GPR15, an orphan G-protein coupled receptor known as a SIV/HIV co-receptor, controls the specific homing of T cells, particularly FOXP3+ regulatory T cells (Tregs), to the large intestine lamina propria (LILP). As shown herein, GPR15 expression is modulated by gut microbiota and TGF-β1, but not by retinoic acid. GPR15-deficient mice were prone to develop more severe large intestine inflammation, which was rescued by the transfer of GPR15-sufficient Tregs. Findings presented herein thus describe a T cell homing receptor for LILP, namely GPR15, and indicate that GPR15 plays a key role in mucosal immune homeostasis, largely by regulating the influx of Tregs. The present study also demonstrates a functional compartmentalization of immune tolerance through the differential requirements for Treg homing to the small and large bowel.

In accordance with the discoveries set forth herein, a method for generating a population of T cells that migrates preferentially to the large intestine is presented herein, the method comprising the steps of: isolating a population of T cells from a mammal; and incubating the population of T cells in culture medium comprising TGF-β, IL-21, and retinoic acid to produce a population of T cells having enhanced GPR15 expression, wherein the enhanced GPR15 expression confers on the population of T cells an ability to migrate preferentially to the large intestine. In an embodiment, the culture medium is serum-free culture medium or RPMI, for example, with serum. The method may optionally further comprise IL-2 and/or anti-CD3/CD28 activating agents in the culture medium during the incubating step. In an embodiment of methods described herein, the incubating step is at least 3 days. More particularly, the incubating step is 3-7 days.

In an aspect thereof, a method for generating a population of CD4+CD3+CD25+T cells that migrates preferentially to the large intestine is presented herein, the method comprising the steps of: isolating a population of CD4+CD3+CD25+T cells from a mammal; and incubating the population of CD4+ CD3+CD25+T cells in culture medium comprising TGF-β, IL-21, and retinoic acid to produce a population of CD4+ CD3+CD25+T cells having enhanced GPR15 expression, wherein the enhanced GPR15 expression confers on the population of CD4+CD3+CD25+T cells an ability to migrate preferentially to the large intestine. The population of CD4+ CD3+CD25+T cells isolated from the mammal may optionally be further selected to be negative for expression of CD127 (CD127−).

In a particular embodiment, the population of CD4+CD3+ CD25+ T cells or CD4+CD3+CD25+ CD127− T cells is isolated from whole blood or buffy coats of adults.

In an embodiment of the method for generating CD4+ CD3+CD25+ T cells or CD4+CD3+CD25+ CD127− T cells having enhanced GPR15 expression and ability to migrate preferentially to the large intestine, the culture medium comprises TGF-β at a concentration of at least 0.1 ng/ml; IL-21 at a concentration of at least 0.1 ng/ml; and retinoic acid at a concentration of less than or equal to 5 nM. In a more particular embodiment, the culture medium comprises TGF-β at a concentration of about 5-20 ng/ml; IL-21 at a concentration of about 10-20 ng/ml; and retinoic acid at a concentration of about 0.01-1 nM. In accordance with the present findings, the presence of TGF-β, IL-21, and retinoic acid in the culture medium is sufficient to confer upon T cells (e.g., CD4+CD3+ CD25+T cells or CD4+CD3+CD25+CD127−T cells) incubated therein the property of enhanced GPR15 expression and ability to migrate preferentially to the large intestine. Accordingly, no additional supplements (e.g., cytokines, lymphokines, growth factors, or nutrients) are necessary to confer these properties, so the culture medium can be viewed as consisting essentially of TGF-β, IL-21, and retinoic acid with respect to its ability to confer upon T cells cultured therein enhanced GPR15 expression and ability to migrate preferentially to the large intestine. In a further embodiment thereof, the culture medium further comprises IL-2. In a particular embodiment, the culture medium comprises IL-2 at a concentration of at least 20 U/ml. In a more particular embodiment, the culture medium comprises IL-2 at a concentration of about 100 U/ml. In a further embodiment, the culture medium further comprises anti-CD3/CD28 activating agents. In another embodiment, the culture medium is serum-free culture medium or RPMI, for example, with serum. In an embodiment thereof, the incubating step is at least 3 days. More particularly, the incubating step is 3-7 days.

In a particular embodiment, the population of CD4+CD3+ CD25+T cells or CD4+CD3+CD25+CD127−T cells is isolated based on positive cell surface staining for cell surface antigens or receptors.

In a further embodiment, the method further comprises an enrichment step, whereby the population of CD4+CD3+ CD25+T cells or CD4+CD3+CD25+CD127−T cells having enhanced GPR15 expression is selected for expression of at least one cell surface marker or cell surface antigen expressed on regulatory T (Treg) cells, wherein the at least one cell surface marker or cell surface antigen expressed on Treg cells is GPR15, integrin α4β7, Glycoprotein A repetitions predominant (GARP), or Latency-associated peptide (LAP); and/or for absence of expression of CCR9 (CCR9−).

In another embodiment, the method further comprises administering the population of CD4+CD3+CD25+T cells or CD4+CD3+CD25+CD127−T cells having enhanced GPR15 expression and ability to migrate preferentially to the large intestine in a therapeutically effective amount to the mammal, wherein the mammal is afflicted with an inflammatory condition of the large intestine. In a particular embodiment, the mammal receiving the CD4+CD3+CD25+T cells or CD4+ CD3+CD25+CD127−T cells having enhanced GPR15 expression and ability to migrate preferentially to the large intestine to the mammal is the mammal from whence the original population of CD4+CD3+CD25+T cells or CD4+ CD3+CD25+CD127−T cells was isolated. In a particular embodiment, the inflammatory condition of the large intestine is inflammatory bowel disease, idiopathic colitis, or infectious colitis. In a more particular embodiment, the inflammatory bowel disease is Crohn's disease or ulcerative colitis.

In another aspect, a method for generating a population of CD4+ or CD8+ effector T cells that migrate preferentially to the large intestine is presented, the method comprising the steps of: isolating a population of CD4+CD3+CD25− or CD8+CD3+CD25− T cells from a mammal; and incubating the CD4+CD3+CD25− or CD8+CD3+CD25− T cells in culture medium comprising TGF-β; IL-21 or IL-6 or IL-27; and retinoic acid to produce a population of CD4+ or CD8+ effector T cells having enhanced GPR15 expression, wherein the enhanced GPR15 expression confers on the population of CD4+ or CD8+ effector T cells an ability to migrate preferentially to the large intestine. The population of CD4+CD3+ CD25− T cells or CD8+CD3+CD25− T cells isolated from the mammal may optionally be further selected for expression of CD45RA (CD45RA+).

In a particular embodiment, the population of CD4+CD3+ CD25− or CD8+CD3+CD25− T cells is isolated from whole blood or buffy coats of adults.

In a further embodiment of the method for generating CD4+ or CD8+ effector T cells having enhanced GPR15 expression and ability to migrate preferentially to the large intestine, the culture medium comprises TGF-β at a concentration of at least 0.01 ng/ml; IL-21 or IL-6 or IL-27 at a concentration of at least 0.1 ng/ml; and retinoic acid at a concentration of less than or equal to 5 nM. In a more particular embodiment, the culture medium comprises TGF-β at a concentration of about 0.5-20 ng/ml; IL-21 or IL-6 or IL-27 at a concentration of about 1-20 ng/ml; and retinoic acid at a concentration of about 0.01-5 nM. In accordance with the present findings, the presence of TGF-β; IL-21 or IL-6 or IL-27; and retinoic acid in the culture medium is sufficient to confer upon T cells (e.g., CD4+CD3+CD25− T cells, CD8+ CD3+CD25− T cells, CD4+CD3+CD45RA+CD25− naive T cells, or CD8+CD3+CD45RA+CD25−naive T cells) incubated therein the property of enhanced GPR15 expression and ability to migrate preferentially to the large intestine. Accordingly, no additional supplements (e.g., cytokines, lymphokines, growth factors, or nutrients) are necessary to confer these properties, so the culture medium can be viewed as consisting essentially of TGF-β; IL-21 or IL-6 or IL-27; and retinoic acid with respect to its ability to confer upon T cells cultured therein enhanced GPR15 expression and ability to migrate preferentially to the large intestine. In a further embodiment thereof, the culture medium further comprises IL-2. In a particular embodiment, the culture medium comprises IL-2 at a concentration of at least 5 U/ml. In a more particular embodiment, the culture medium comprises IL-2 at a concentration of about 100 U/ml. In a further embodiment, the culture medium further comprises anti-CD3/CD28 activating agents. In another embodiment, the culture medium is serum-free culture medium or RPMI, for example, with serum. In particular embodiment, the incubating step is at least 3 days. More particularly, the incubating step is 3-7 days.

In a particular embodiment, the population of CD4+ CD3+ CD25− T cells, CD8+CD3+ CD25− T cells, CD4+ CD3+ CD45RA+CD25−naive T cells, or CD8+CD3+ CD45RA+ CD25−naive T cells is isolated based on positive cell surface staining for cell surface antigens or receptors.

In a further embodiment, the method further comprises an enrichment step, whereby the population of CD4+ or CD8+ effector T cells having enhanced GPR15 expression is selected for expression of a cell surface marker or cell surface antigen expressed on effector T (Teff) cells, wherein the cell surface marker or cell surface antigen expressed on Teff cells is GPR15 or integrin α4β7; and/or for absence of expression of Glycoprotein A repetitions predominant (GARP−), Latency-associated peptide (LAP−), or CCR9 (CCR9−).

In another embodiment, the method further comprises administering to the mammal in a therapeutically effective amount the population of CD4+ or CD8+ effector T cells having enhanced GPR15 expression and ability to migrate preferentially to the large intestine, wherein the mammal is afflicted with a cancer or infection of the large intestine. In a particular embodiment, the mammal receiving the population of CD4+ or CD8+ effector T cells is the mammal from whence the original population of CD4+ or CD8+ T cells was isolated. In a particular embodiment thereof, the cancer is colon cancer or a cancer that has metastasized to the large intestine. In another particular embodiment, the infection is a bacterial or viral infection. Such infections may be acquired by ingesting contaminated food. Certain strains of *Escherichia coli* (*E. coli*), for example, can cause severe, even life threatening, infections in the large intestine when ingested by a mammal in sufficient quantity.

With regard to the population of CD4+ or CD8+ effector T cells having enhanced GPR15 expression and ability to migrate preferentially to the large intestine generated using methods described herein, the method may further comprise treating the population of CD4+ or CD8+ effector T cells having these properties to induce antigen specificity in the population of CD4+ or CD8+ T cells.

In another aspect, a method for generating a population of T cells that migrates preferentially to the large intestine is presented, the method comprising the steps of: isolating a population of T cells from a mammal and transfecting/transducing the population of T cells with a nucleic acid sequence encoding GPR15 to produce a population of T cells having enhanced GPR15 expression, wherein the enhanced GPR15 expression confers on the population of T cells an ability to migrate preferentially to the large intestine. In a particular embodiment thereof, the method further comprises transfecting/transducing the population of T cells with nucleic acid sequences encoding integrin α4 and integrin β7 to confer enhanced expression of integrin α4β7 heterodimer to the T cell population. In a further embodiment, the population of T cells is isolated from whole blood or buffy coats of adult mammals.

In a particular embodiment, the population of T cells is activated prior to the transfecting/transducing step. Suitable agents for activating T cells include anti-CD3/CD28 activating agents.

The population of T cells isolated from the mammal may be selected to comprise CD4+CD3+CD25+T cells, CD4+CD3+CD25+CD127−T cells, CD4+CD3+CD25−T cells, or CD8+CD3+CD25−T cells and the transfecting/transducing step produces a population of CD4+CD3+CD25+T cells, CD4+CD3+CD25+CD127−T cells, CD4+CD3+ effector T cells, or CD8+CD3+ effector T cells, respectively, having enhanced GPR15 expression and ability to migrate preferentially to the large intestine.

In an aspect thereof, the method further comprises administering to the mammal the transfected/transduced population of CD4+CD3+CD25+T cells or CD4+CD3+CD25+CD127−T cells having enhanced GPR15 expression and ability to migrate preferentially to the large intestine or a composition thereof, wherein the mammal is afflicted with an inflammatory condition of the large intestine. In an embodiment thereof, the mammal is afflicted with inflammatory bowel disease, idiopathic colitis, or infectious colitis. In a more particular embodiment, the inflammatory bowel disease is Crohn's disease or ulcerative colitis. The transfected/transduced population of CD4+CD3+CD25+T cells or CD4+CD3+CD25+CD127−T cells having enhanced GPR15 expression and ability to migrate preferentially to the large intestine or a composition thereof is also envisioned for use in the treatment of an inflammatory condition of the large intestine in a subject, wherein the transfected/transduced population of CD4+CD3+CD25+T cells or CD4+CD3+CD25+CD127−T cells or composition thereof is administered in a therapeutically effective amount to the subject. Also encompassed herein is use of the transfected/transduced population of CD4+CD3+CD25+T cells or CD4+CD3+CD25+CD127−T cells or a composition thereof for the manufacture or preparation of a medicament for treating an inflammatory condition of the large intestine in a subject, wherein the medicament is prepared to be administrable in a dosage regimen whereby transfected/transduced T cells or a composition thereof is delivered in a therapeutically effective amount to the subject. Exemplary inflammatory conditions of the large intestine include, without limitation, inflammatory bowel disease (e.g., Crohn's disease or ulcerative colitis), idiopathic colitis, or infectious colitis. In a particular embodiment, the subject is a mammal, and more particularly, the mammal is a human.

In another aspect, the method further comprises administering to the mammal the transfected/transduced population of CD4+CD3+ effector T cells or CD8+CD3+ effector T cells having enhanced GPR15 expression and ability to migrate preferentially to the large intestine or a composition thereof, wherein the mammal is afflicted with a cancer or infection of the large intestine. In an embodiment, the mammal is afflicted with colon cancer or a cancer that has metastasized to the large intestine. In another embodiment, the mammal is afflicted with a bacterial or viral infection. The transfected/transduced population of CD4+CD3+ effector T cells or CD8+CD3+ effector T cells having enhanced GPR15 expression and ability to migrate preferentially to the large intestine or a composition thereof is also envisioned for use in the treatment of a cancer or infection of the large intestine, wherein the transfected/transduced population of CD4+CD3+ effector T cells or CD8+CD3+ effector T cells or a composition thereof is administered in a therapeutically effective amount to the subject. Also encompassed herein is the use of the transfected/transduced population of CD4+CD3+ effector T cells or CD8+CD3+ effector T cells or a composition thereof for the manufacture or preparation of a medicament for treating a cancer or infection of the large intestine, wherein the medicament is prepared to be administrable in a dosage regimen whereby the transfected/transduced population of CD4+CD3+ effector T cells or CD8+CD3+ effector T cells or a composition thereof is delivered in a therapeutically effective amount to the subject. In an embodiment, the cancer of the large intestine is colon cancer or a cancer that has metastasized to the large intestine. In another embodiment, the infection of the large intestine is a bacterial or viral infection. In a particular embodiment, the subject is a mammal, and more particularly, the mammal is a human.

Populations of T cells having enhanced GPR15 expression and ability to migrate preferentially to the large intestine are also encompassed herein. In a particular embodiment, the population comprises CD4+CD3+CD25+T cells, CD4+

CD3+CD25+CD127−T cells, or CD4+ or CD8+ effector T cells having enhanced GPR15 expression and ability to migrate preferentially to the large intestine. In a particular embodiment thereof, the population of T cells having enhanced GPR15 expression and ability to migrate preferentially to the large intestine is an essentially homogeneous population of T cells having enhanced GPR15 expression and ability to migrate preferentially to the large intestine. Such populations may be generated using any of the methods described herein. Compositions comprising the populations of T cells having enhanced GPR15 expression and ability to migrate preferentially to the large intestine (e.g., homogeneous populations of T cells) are also encompassed herein, as are methods of using same for, inter alia, therapeutic purposes.

In another aspect, a population of T cells having enhanced GPR15 expression and ability to migrate preferentially to the large intestine (e.g., a population of CD4+CD3+CD25+T cells, CD4+CD3+CD25+CD127−T cells, or CD4+ or CD8+ effector T cells having enhanced GPR15 expression and ability to migrate preferentially to the large intestine) or a composition thereof is presented for use in the treatment of a an autoimmune and/or inflammatory condition of the large intestine (Treg cells) or a cancer or an infection of the large intestine (Teff cells) in a subject, wherein the population of T cells having enhanced GPR15 expression and ability to migrate preferentially to the large intestine or a composition thereof is administered in a therapeutically effective amount to the subject. As described herein, subjects and patients may be mammals, and more particularly, may be humans. In a particular embodiment, the inflammatory condition of the large intestine is inflammatory bowel disease, idiopathic colitis, or infectious colitis. In a more particular embodiment, the inflammatory bowel disease is Crohn's disease or ulcerative colitis. In another particular embodiment, the cancer is colon cancer or a cancer that has metastasized to the large intestine. In yet another particular embodiment, the infection is a bacterial or viral infection, which may be acquired by ingesting contaminated food. Certain *E. coli* strains, for example, can cause severe, even life threatening, infections in the large intestine when ingested by a mammal in sufficient quantity.

In another aspect, use of a population of T cells having enhanced GPR15 expression and ability to migrate preferentially to the large intestine or a composition thereof for the manufacture of a medicament for treating an autoimmune and/or inflammatory condition of the large intestine (Treg cells) or a cancer or an infection of the large intestine (Teff cells) in a subject is envisioned, wherein the medicament is prepared to be administered in a dosage regime whereby the population of T cells having enhanced GPR15 expression and ability to migrate preferentially to the large intestine or a composition thereof is delivered in a therapeutically effective amount to the subject. In a particular embodiment, the subject is a mammal. In a more particular embodiment, the mammal is a human. In a particular embodiment, the inflammatory condition of the large intestine is inflammatory bowel disease, idiopathic colitis, or infectious colitis. In a more particular embodiment, the inflammatory bowel disease is Crohn's disease or ulcerative colitis. In another particular embodiment, the cancer is colon cancer or a cancer that has metastasized to the large intestine. In yet another particular embodiment, the infection is a bacterial or viral infection, which infections may be acquired by ingesting contaminated food. Certain strains of *E. coli*, for example, are known to be associated with severe and sometimes life threatening cases of food poisoning.

The aforementioned methods may further comprise performing a screening assay to identify an agent that modulates GPR15 expression, whereby the population of T cells isolated from the mammal is divided to generate a first and a second population and a candidate agent is added to the culture medium during the incubating step for the first population and a control agent (or no agent) is added to the culture medium during the incubating step for the second population, wherein a change in levels of enhanced GPR15 expression in the first population relative to the second population identifies the candidate agent as a GPR15 expression modulator. In an embodiment thereof, wherein the change is an increase in levels of enhanced GPR15 expression in the first population relative to the second population, the screening method identifies the GPR15 expression modulator as an enhancer/promoter of GPR15 expression (GPR15 activator). In another embodiment thereof, wherein the change is a decrease in levels of enhanced GPR15 expression in the first population relative to the second population, the screening method identifies the GPR15 expression modulator as an inhibitor of GPR15 expression (GPR15 inhibitor). Agents identified using the aforementioned screening methods may be used alone or in conjunction with cytokines and compounds described herein to treat isolated T cell populations ex vivo to enhance GPR15 expression therein, after which T cell populations with enhanced GPR15 expression and ability to migrate to the large intestine are administered to a subject in need thereof.

Also encompassed herein are methods for blocking GPR15-mediated homing to the large intestine. Such methods may be achieved by administering an agent that inhibits GPR15 signaling and/or inhibits GPR15-mediated binding to its ligand or ligands. Exemplary agents for blocking GPR15-mediated binding to its ligand or ligands include antibodies that inhibit interaction with the ligand via, for example, steric hindrance of interaction with the ligand or GPR15 internalization. Small molecule inhibitors are also envisioned.

Also encompassed herein is a method for assessing efficacy of a regimen for modulating immune responses in the large intestine of a subject, the method comprising measuring the number of T cells expressing GPR15 in the subject, wherein the number of T cells expressing GPR15 in the subject is positively correlated with efficacy of the regimen for the subject. In an embodiment thereof, the T cells are isolated from blood of the subject.

In a particular embodiment thereof, the regimen is intended to inhibit immune responses in the large intestine of the subject, the method comprising determining the number of regulatory T (Treg) cells expressing GPR15 before initiation of the regimen and the number of Treg cells expressing GPR15 after initiation of the regimen, wherein an increase in the number of Treg cells expressing GPR15 after initiation of the regimen relative to before initiation of the regimen is positively correlated with efficacy of the regimen. A decrease in the number of effector T (Teff) cells expressing GPR15 before initiation of the regimen and the number of Teff cells expressing GPR15 after initiation of the regimen may also be correlated with efficacy of the regimen.

In another embodiment thereof, the regimen is intended to promote or enhance immune responses in the large intestine of the subject, the method comprising determining the number of Teff cells expressing GPR15 before initiation of the regimen and the number of Teff cells expressing GPR15 after initiation of the regimen, wherein an increase in the number of Teff cells expressing GPR15 after initiation of the regimen relative to before initiation of the regimen is positively correlated with efficacy of the regimen. A decrease in the number of Treg cells expressing GPR15 before initiation of the regimen and the number of Treg cells expressing GPR15 after initiation of the regimen may also be correlated with efficacy of the regimen.

Other features and advantages of the invention will be apparent from the following description of the particular embodiments thereof, and from the claims.

BRIEF DESCRIPTION OF THE DRAWINGS

FIG. 1A-1C. GPR15 is preferentially expressed in and regulates the frequency of FOXP3$^+$ regulatory T cells in the large intestine lamina propria (LILP). (1A) Gpr15$^{gfp/+}$ mice were bred to Foxp3$^{ires-mrfp}$ mice. GFP and mRFP expression was examined in T cell subsets from different tissues (SILP: Small intestine lamina propria; DN T: CD4$^-$CD8β$^-$ T cells). Results shown are representative of at least three independent experiments. (1B) Percentage of FOXP3$^+$ Tregs among CD4$^+$ T cells in different tissues of Gpr15$^{gfp/+}$ mice (Het) and Gpr15$^{gfp/gfp}$ (KO) mice (129/B6 mixed background: n=2-8; B6N10 (C57BL/6-backcrossed 10 times): n=9; combined from at least two independent experiments). (1C) Numbers of FOXP3$^+$ (left panel) and FOXP3$^-$ cells (right panel) in the LILP were compared between OT-II Rag2$^{-/-}$ Gpr15$^{gfp/+}$ (Het) and OT-II Rag2$^{-/-}$ Gpr15$^{gfp/gfp}$ (KO) mice after OVA administration (n=12, combined from four independent experiments). *p<0.05 (t-test).

FIG. 6A-6H. GPR15 is preferentially expressed in LILP Tregs. (6A) GFP expression in different tissues of Gpr15$^{gfp/+}$ mice. GFP$^+$ populations were additionally analyzed for T cell receptor expression. Most GFP$^+$ cells were TCRβ$^+$. (6B) Cellular identity of GFP$^+$ population was determined by surface staining (DN T: CD4$^-$CD8β$^-$T cells). CD4$^+$ T cells made up the most significant population of GFP$^+$ cells in the LILP (B6/Balb/c mixed background). (6C) GFP expression was determined among CD4$^+$ T cells, CD8$^+$ T, and DN T cells from various tissues of Gpr15$^{gfp/+}$ mice. T cells from the LILP have the most significant expression of GFP. (6D) Different parts of the large intestine and the small intestine were examined for GFP$^+$ cells among CD4$^+$ T cells. (6E, 6F) GFP expression in various immune cell subsets from the LILP. (6G) GFP$^+$ and GFP$^-$ cells among CD4$^+$ T cells in the LILP of Gpr15$^{gfp/+}$ B6/Balb/c mixed background mice were sorted and stained for FOXP3. (6H) Percentage of GFP$^+$ cells in each T cell subset from the LILP. GFP$^+$ cells are most abundant among FOXP3$^+$ regulatory T cells (n=5-7).

FIG. 7A-7C. Effect of GPR15 deficiency on intestinal lymphocyte subsets. (7A) Ratio of HELIOS$^-$/HELIOS$^+$ cells among Foxp3$^+$ T cells in the LILP, SILP, and spleen of Gpr15$^{gfp/+}$ (Het) and Gpr15$^{gfp/gfp}$ (KO) mice. (7B, 7C) Cell numbers for each immune cell subset (FOXP3$^+$ Tregs, FOXP3$^-$ CD4$^+$ T cells, CD8$^+$ T cells, DN T (CD4$^-$CD8β$^-$ T cells), and NK cells) in the LILP (7B) and SILP (7C) of het and KO mice (n=9 for LILP, n=5 for SILP). Representative of at least three independent experiments. *p<0.05 (t-test).

FIG. 8A-8C. Treg frequency in the LILP decreases in the absence of GPR15 in an antigen-specific immune response. (8A, 8B) 1.5% Ovalbumin (OVA) in drinking water was provided to OT-II Rag2$^{-/-}$ Gpr15$^{gfp/+}$ mice. (8A) GFP expression in T cells from various tissues (Average percentage of GFP$^+$=4.5(±0.2)% for LILP; 0.06 (±0.02)% for MLN, 0.02 (±0.01)% for PLN (n=3), Representative of three independent experiments). (8B) GFP$^+$ and GFP$^-$ cells in the LILP were sorted and stained for FOXP3. (8C) Percentages of FOXP3$^+$ cells among CD4$^+$ T cells in LILP (left panel) and spleen (right panel) of OT-II Rag2$^{-/-}$ Gpr15$^{gfp/+}$ (Het) and OT-II Rag2$^{-/-}$ Gpr15$^{gfp/gfp}$ (KO) mice (n=9-13, combined result of three independent experiments). *p<0.05 (t-test).

FIG. 9A-9F. GPR15-mediated signaling provides a selective advantage for homing to the large intestine in cooperation with integrin α4 and β7. (9A) A diagram of short-term competitive homing assay with CD4$^+$ T cells transduced with various forms of GPR15 performed in FIG. 2A, 2B, 2C, and FIG. 9B, 9D, 9E, 9F, 13B, 13C. Gpr15-transduced and control-transduced cells express a common marker, THY1.1, and different congenic markers, CD45.1 and CD45.2, respectively (9B) Percentage of Gpr15-transduced and control-transduced donor cells among total CD4+ T cells (cells in the recipients included) in different tissues (SILP: small intestine lamina propria; MLN: Mesenteric lymph nodes; PLN: Inguinal, Brachial, and Axillary lymph nodes) (n=6, combined result of three independent experiments). (9C) Cell surface expression of GPR15-GFP and GPR15mut-GFP was confirmed in 293T cells. (9D) Homing of CD4+ T cells transduced with Gpr15 fused with gfp (GPR15-GFP) compared with those transduced with control vector (n=6, combined result of four independent experiments). (9E) Time course experiment after transfer of Gpr15-transduced and control-transduced donor CD4+ T cells. GPR15+ cells display preferential migration to the LILP at 2 h after transfer (n=3). (9F) Recipient mice were injected i.p. with 100 µg of non-specific or integrin-blocking antibodies 12 hrs before transfer. Gpr15-transduced and control-transduced donor CD4+ T cells were also treated with corresponding antibodies before transfer. Numbers of GPR15+ cells in the LILP are shown (n=3, a representative of two-independent experiments). *p<0.05 (t-test).

FIG. 15. Expression of GPR15 mRNA in cells from human tissues. Lymphocytes were sorted from human blood and tissues and Taqman RT-PCR was performed for GPR15 and normalized using BETA-ACTIN. (Blood: n=4, Colon: n=4-8, Small intestine: n=3 (1 from duodenum and 2 from ileum)). *p<0.05 (t-test).

FIG. 16A-16B. Model for regulation of lymphocyte trafficking to the small versus large intestine. (16A) Retinoic acid is well known to induce tropism for the small intestine by inducing integrin α4 and CCR9 expression in T and B cells (14, 15, 40). According to the present findings, there is an additional retinoic acid-independent pathway to induce tropism for the large intestine. TGF-β combined with unknown factors has a role in inducing GPR15 expression in vivo to enable T cells to home to the large intestine. Integrin α4 is still required for the majority of GPR15-mediated homing to the large intestine. Therefore, homing of lymphocytes to small and large intestine is controlled differentially by at least two different cues and by distinct homing receptors. (16B) According to our study, adaptive immune responses in the gut are compartmentalized between the small bowel and the large bowel. Therefore, immune tolerance in the gut is also differentially regulated in those two regions. TGF-β appears to be crucial for Treg-mediated tolerance in both cases either for differentiation of inducible Tregs or for induction of GPR15 for the large intestine. While CCR9 is important for the induction of systemic oral tolerance to food antigens (41), its role for Treg homing during the local immune regulation in the small intestine is not known.

DETAILED DESCRIPTION OF THE INVENTION

Figure 1B:
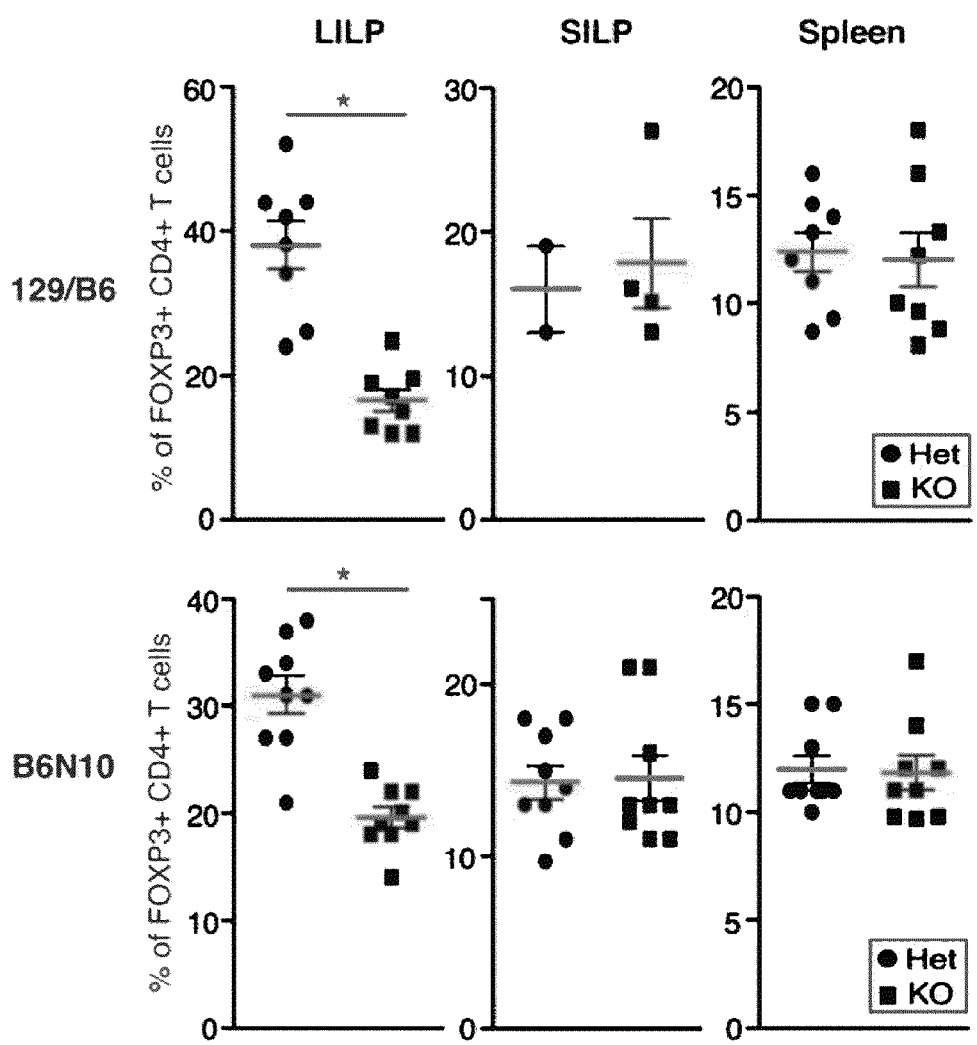

In order to more clearly set forth the parameters of the present invention, the following definitions are used:

As used in this specification and the appended claims, the singular forms "a", "an", and "the" include plural references unless the context clearly dictates otherwise. Thus for example, reference to "the method" includes one or more methods, and/or steps of the type described herein and/or which will become apparent to those persons skilled in the art upon reading this disclosure.

The term "complementary" refers to two DNA strands that exhibit substantial normal base pairing characteristics. Complementary DNA may, however, contain one or more mismatches.

The term "hybridization" refers to the hydrogen bonding that occurs between two complementary DNA strands.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. Exemplary isolated nucleic acids include, without limitation, those encoding human and mouse GPR15 (SEQ ID NOs: 1 and 3) and those encoding human and mouse integrin α4 (SEQ ID NOs: 5 and 7). Polypeptides encoded thereby, including human and mouse GPR15 (SEQ ID NOs: 2 and 4) and human and mouse integrin α4 (SEQ ID NO: 6 and 8) are also encompassed herein. Nucleic acid sequences encoding human integrin β7 (SEQ ID NO: 9) and the polypeptide encoded thereby (SEQ ID NO: 10) are also encompassed herein. Nucleic acid sequences encoding mouse integrin β7 (SEQ ID NO: 11) and the polypeptide encoded thereby (SEQ ID NO: 12) are also encompassed herein.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it is generally associated in its natural state (i.e., in cells or tissues). An isolated nucleic acid (either DNA or RNA) may further represent a molecule produced directly by biological or synthetic means and separated from other components present during its production.

The term "functional" as used herein implies that the nucleic or amino acid sequence is functional for the recited assay or purpose.

The phrase "consisting essentially of" when referring to a particular nucleotide or amino acid means a sequence having the properties of a given SEQ ID No: For example, when used in reference to an amino acid sequence, the phrase includes the sequence per se and molecular modifications that would not affect the basic and novel characteristics of the sequence. With regard to culture medium, the phrase "consisting essentially of" may be used to indicate that the presence of a recited growth factor/cytokine/nutrient combination (e.g., TGF-β, IL-21, and retinoic acid) is sufficient to confer a structural and/or functional property on cells cultured in the presence of the indicated combination.

A "replicon" is any genetic element, for example, a plasmid, cosmid, bacmid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression vector" or "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the term "operably linked" refers to a regulatory sequence capable of mediating the expression of a coding sequence and which is placed in a DNA molecule (e.g., an expression vector) in an appropriate position relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Primers may be labeled fluorescently with 6-carboxyfluorescein (6-FAM). Alternatively primers may be labeled with 4,7,2',7'-Tetrachloro-6-carboxyfluorescein (TET). Other alternative DNA labeling methods are known in the art and are contemplated to be within the scope of the invention.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

The term "substantially pure" refers to a preparation comprising at least 50-60% by weight of a given material (e.g., nucleic acid, oligonucleotide, protein, etc.). More particularly, the preparation comprises at least 75% by weight, and most particularly 90-95% by weight of the given compound. Purity is measured by methods appropriate for the given compound (e.g. chromatographic methods, agarose or polyacrylamide gel electrophoresis, HPLC analysis, and the like). "Mature protein" or "mature polypeptide" shall mean a polypeptide possessing the sequence of the polypeptide after any processing events that normally occur to the polypeptide during the course of its genesis, such as proteolytic processing from a polypeptide precursor. In designating the sequence or boundaries of a mature protein, the first amino acid of the mature protein sequence is designated as amino acid residue 1.

The term "tag", "tag sequence" or "protein tag" refers to a chemical moiety, either a nucleotide, oligonucleotide, polynucleotide or an amino acid, peptide or protein or other chemical, that when added to another sequence, provides additional utility or confers useful properties to the sequence, particularly with regard to methods relating to the detection or isolation of the sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned by, the trained artisan, and are contemplated to be within the scope of this definition.

The terms "transform", "transfect", "transduce", shall refer to any method or means by which a nucleic acid is introduced into a cell or host organism and may be used interchangeably to convey the same meaning. Such methods include, but are not limited to, viral transduction, transfection, electroporation, microinjection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. In other applications, the introduced nucleic acid may exist in the recipient cell or host organism only transiently.

A "clone" or "clonal cell population" is a population of cells derived from a single cell or common ancestor by mitosis.

A "cell line" is a clone of a primary cell or cell population that is capable of stable growth in vitro for many generations.

An "immune response" signifies any reaction produced by an antigen, such as a protein antigen, in a host having a functioning immune system. Immune responses may be either humoral, involving production of immunoglobulins or antibodies, or cellular, involving various types of B and T lymphocytes, dendritic cells, macrophages, antigen presenting cells and the like, or both. Immune responses may also involve the production or elaboration of various effector molecules such as cytokines, lymphokines and the like. Immune responses may be measured both in in vitro and in various cellular or animal systems.

An "antibody" or "antibody molecule" is any immunoglobulin, including antibodies and fragments thereof, that binds to a specific antigen. The term includes polyclonal, monoclonal, chimeric, and bispecific antibodies. As used herein, antibody or antibody molecule contemplates both an intact immunoglobulin molecule and an immunologically active portion of an immunloglobulin molecule such as those portions known in the art as Fab, Fab', F(ab')2 and F(v).

The term "about" as used herein refers to a variation in a stated value or indicated amount of up to 10%, 9%, 8%, 7%, 6%, 5%, 4%, 3%, 2%, 1%, 0.75%, 0.5%, 0.25% or 0.1%, wherein the variation can be either an increase or a decrease in the stated value or indicated amount. Use of the term may, therefore, be used to establish a range of values or amounts.

As used herein, the term "serum-free culture medium" is defined as serum-free cell culture medium that has a defined chemical composition and supports proliferation of human lymphocytes. A list of serum-free culture medium useful in the present invention would include, without limitation, LONZA XVIVO-5, XVIVO-10, XVIVO-20, Sigma StemLine I, StemLine II, Yssel's media and AimV media. An exemplary serum-free medium is serum-free XVIVO-20 (Lonza), which may optionally be supplemented with penicillin-streptomycin.

MEM and RPMI are protein-free basal media that do not contain growth factors required for lymphocytes. A skilled practitioner would appreciate that a protein-free basal media can, however, be converted to serum-free media capable of supporting lymphocyte proliferation following addition of required growth factors. Such serum-free media contain specific and defined growth factors (e.g., insulin) that are required for lymphocyte proliferation.

RPMI may further be supplemented with serum at a concentration of, for example, 5-10%. Sera suitable for use in methods described herein include human serum in general and autologous human serum.

As used herein, the term "enhanced GPR15 expression" may be used to refer to an increase in GPR15 protein levels in a population of cells and/or in individual cells. An increase in the number of GPR15 expressing cells in a cell population may be expressed as the percent (%) of GPR15+ T cells present in such a cell population relative to the total number of cells. In accordance with the present invention, methods described herein typically achieve about or at least 50% GPR15+ T cells in a treated T cell population. T cell populations isolated from mammals in accordance with the present methods do not express GPR15 at detectable levels (such populations are essentially 0% GPR15+) and thus, an increase in the number of cells expressing GPR15 to achieve 50% GPR15+ T cells in a population following incubation in the culture medium comprising the indicated cocktail represents a substantial and significant change in both expression pattern and functionality of the T cell population. The present invention is not in any way limited to achieving 50% GPR15+ T cells in a treated cell population and encompasses T cell populations treated or generated in accordance with methods presented herein that comprise equal to or greater than 10%, 20%, 30%, 40%, 50%, 60%, 70%, 80%, 90%, 95%, 96%, 97%, 98%, or 99% GPR15+ T cells. In still more particular embodiments, T cell populations treated or generated in accordance with methods presented herein are 100% GPR15+ T cell populations.

In Vitro Methods

As described herein, the present invention is directed to a method for generating a population of T cells that migrates preferentially to the large intestine, the method comprising the steps of: isolating a population of T cells from a mammal; and incubating the population of T cells in culture medium comprising TGF-β, IL-21 (which may be replaced by IL-6 or IL-27, depending on the T cell types involved as described herein), and retinoic acid, and optionally IL-2 and/or anti-CD3/CD28 activating agents to produce a population of T cells having enhanced GPR15 expression, wherein the enhanced GPR15 expression confers on the population of T cells an ability to migrate preferentially to the large intestine.

In a particular aspect, a method for generating a population of CD4+CD3+CD25+T cells or CD4+CD3+CD25+ CD127−T cells that migrates preferentially to the large intestine is described herein, the method comprising the steps of: isolating a population of CD4+CD3+CD25+T cells or CD4+CD3+CD25+CD127−T cells from a mammal; and incubating the population of CD4+CD3+CD25+T cells or CD4+CD3+ CD25+ CD127−T cells in culture medium comprising TGF-β, IL-21, and retinoic acid, and optionally IL-2 and/or anti-CD3/CD28 activating agents to produce a population of CD4+CD3+CD25+T cells or CD4+CD3+CD25+ CD127−T cells having enhanced GPR15 expression, wherein the enhanced GPR15 expression confers on the population of CD4+CD3+CD25+T cells or CD4+CD3+CD25+ CD127−T cells an ability to migrate preferentially to the large intestine.

In another particular aspect, a method for generating a population of CD4+ or CD8+ effector T cells that migrate preferentially to the large intestine is envisioned, the method comprising the steps of: isolating a population of CD4+ CD25− or CD8+CD25−T cells from a mammal; and incubating the population of CD4+CD25− or CD8+CD25−T cells in culture medium comprising TGF-β, IL-21 or IL-6 or IL-27, and retinoic acid, and optionally IL-2 and/or anti-CD3/CD28 activating agents to produce a population of CD4+ or CD8+ effector T cells having enhanced GPR15 expression, wherein the enhanced GPR15 expression confers on the population of CD4+ or CD8+ effector T cells an ability to migrate preferentially to the large intestine.

Also encompassed herein are methods for genetically engineering T cells to achieve enhanced GPR15 expression. Such methods call for transfection/transduction of exogenous nucleic acid sequences encoding GPR15 into a T cell population, as described in the Examples presented herein. See, for example, FIG. 2 and the description thereof and methodological details pertaining thereto in the Examples. Expression vectors and methods for designing and constructing same are also described herein and known in the art. In a further aspect thereof, T cell populations may be cotransfected or cotransduced with exogenous nucleic acid sequences encoding integrin α4 and integrin β7 to confer enhanced expression of the integrin α4β7 heterodimer to the T cell population. Methods for genetically engineering T cells may be performed using a population of T cells of a particular subtype or having a particular functionality. Such T cell subtypes are described herein and known in the art and include: Treg cells, CD4+ Teff cells, CD8+ Teff cells, and CD4-CD8-T cells. Methods for selecting T cell subtypes are described herein and include methods that involve selection based on expression of cell surface markers and combinations thereof. Such selection methods may involve selection based on the presence or absence of expression of such markers.

In a particular embodiment, a T cell population isolated from a donor subject and either treated with a cocktail of polypeptides, compounds, and/or agents (e.g., cytokines and retinoic acid) as indicated herein or transfected/transduced ex vivo is positively selected for enhanced GPR15 expression (and potentially enhanced α4β7 integrin expression) prior to administration to a recipient. In a particular embodiment thereof, the donor and recipient are identical, and thus, the administered T cell population may be referred to herein as an autologous transplant. In an alternate embodiment, the donor and recipient are of the same species, but not the same individual, and thus, the administered T cell population may be referred to herein as an allogeneic transplant.

The in vitro methods described herein are based on the novel and surprising discoveries of the present inventors. In short, the present inventors have discovered that the orphan G-protein coupled receptor GPR15 controls the specific homing of T cells, particularly FOXP3+ regulatory T cells (Tregs), to the large intestine lamina propria (LILP). The inventors have further determined that GPR15 expression is modulated by gut microbiota and TGF-β1, but not by retinoic acid. GPR15-deficient mice exhibit greater susceptibility to severe inflammation of the large intestine than wild type GPR15 heterozygotes. Transfer of GPR15-sufficient Tregs rescues these GPR15-deficient mice, thereby restoring normal (wild type) inflammatory responses in the large intestine. Results presented herein thus describe a T cell homing receptor for LILP and reveal that GPR15 plays a key role in mucosal immune homeostasis, at least in part by regulating the influx of Tregs. As discussed in greater detail herein below, results presented herein also demonstrate that differential requirements for Treg homing to the small and large bowel exist and this appreciation reveals at least one mechanism whereby functional compartmentalization of immune tolerance is achieved in the intestine.

Figure 11A:
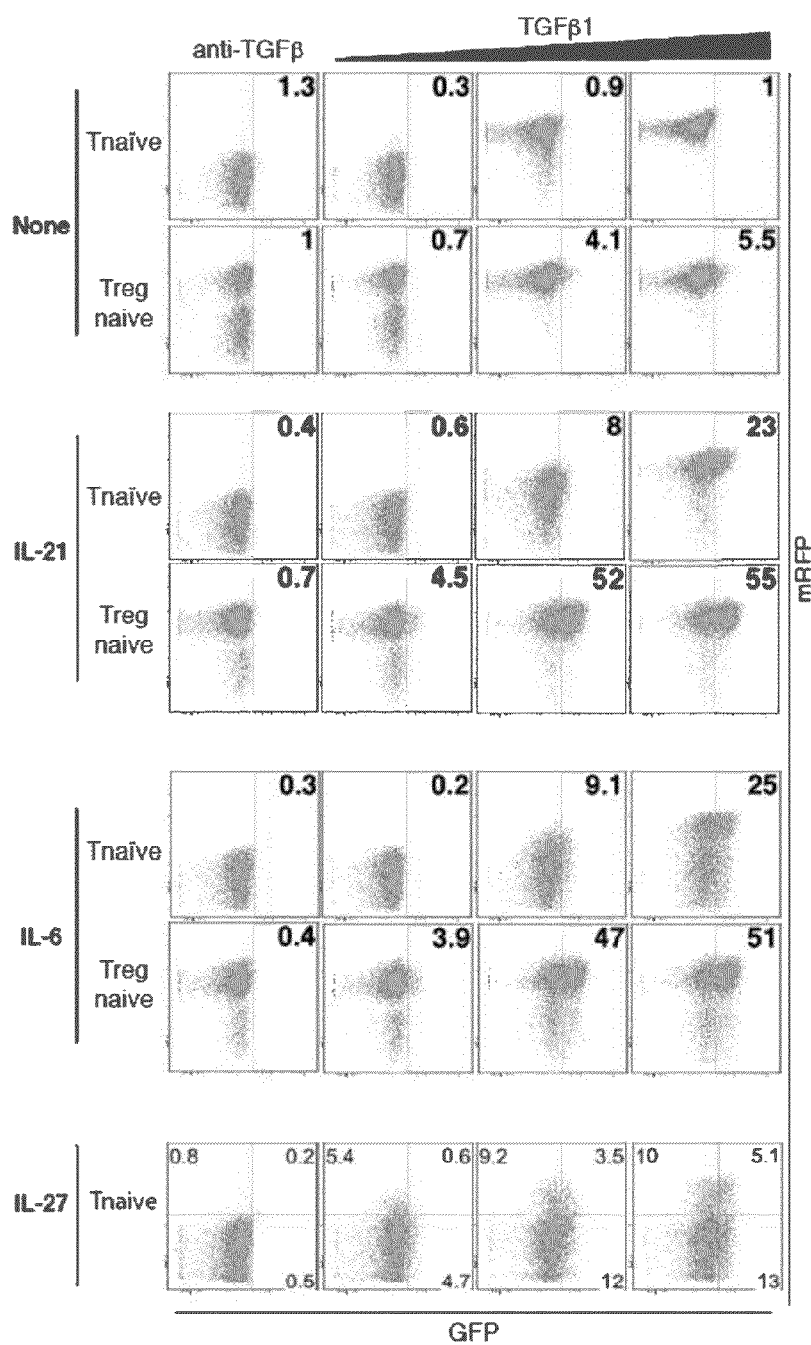
FIG. 11A-11B. GPR15 can be effectively induced in Treg cells and memory T cells in vitro. CD4+ GFP− $T_{naive}$ and Tregs with naive phenotype (11A; CD62L$^{hi}$, CD44$^{lo}$) or with memory phenotype (11B; CD62L$^{lo}$, CD44$^{lo}$) were sorted from Gpr15$^{gfp/+}$ Foxp3$^{ires-mrfp}$ mice and stimulated in the presence of IL-2 (100 U/ml) alone, or additionally with IL-21 (10 ng/ml) or IL-6 (20 ng/ml) or IL-27 (10 ng/ml) and varying concentration of TGF-β1 (αTGF-β blocking antibody, or 0, 0.5 ng/ml, 5 ng/ml of additional TGF-β1). Expression of the GPR15 and Foxp3 reporters was examined at day 3 (Representative of four independent experiments).
Figure 11B:
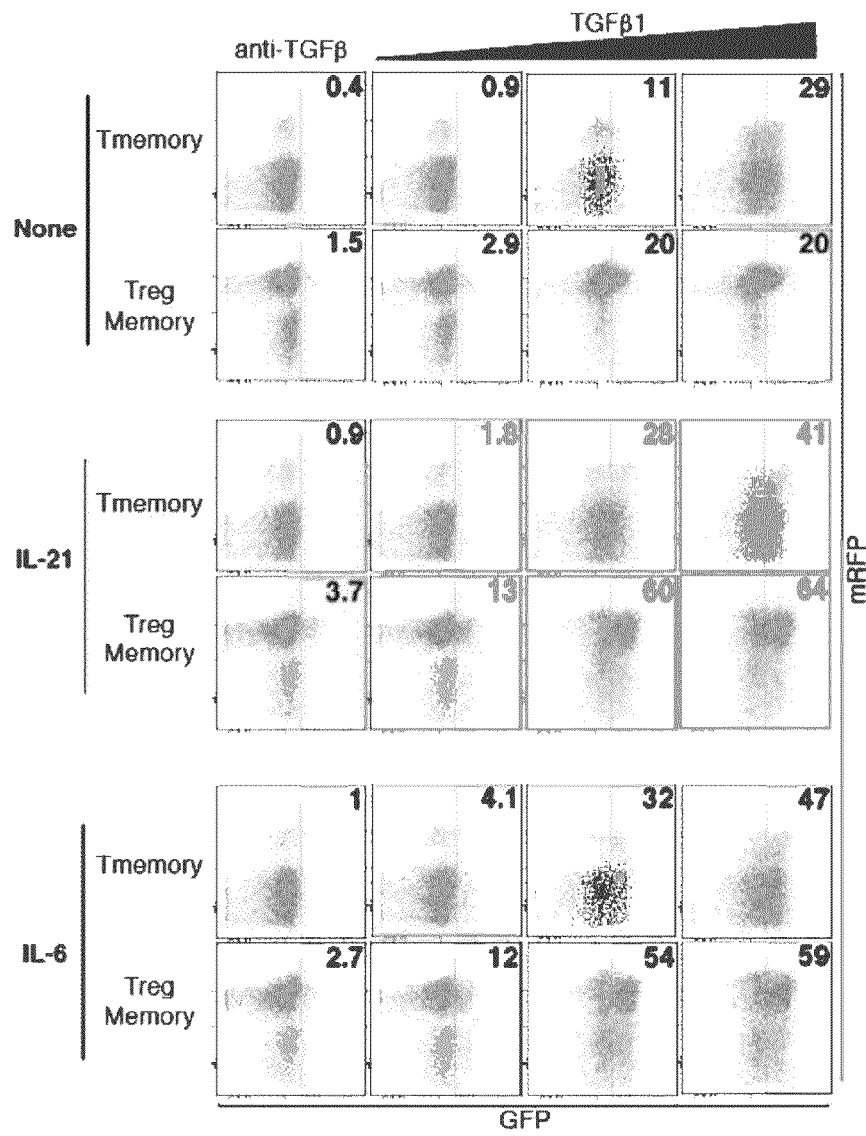

As taught herein, enhanced/increased GPR15 expression in a population of T cells (e.g., CD4+CD3+CD25+CD127−T cells or CD4+ or CD8+ effector T cells) may be determined using a variety of experimental protocols, including, but not limited to, real-time PCR using appropriate primers and/or immunohistochemistry or fluorescence activated sorting (FACS) using antibodies specific for GPR15. Experimental protocols useful for determining expression of GPR15 and other cellular markers (e.g., Treg marker) and relative expression levels thereof are described in detail herein and are understood in the art. As described herein, the in vitro method described herein transforms a population of, for example, CD4+CD3+CD25+CD127-GPR15−T cells into a population wherein at least 50% of the CD4+CD3+CD25+CD127−T cells are GPR15+. The increased frequency of GPR15+ cells in the population of CD4+CD3+CD25+CD127−T cells confers on these cells the ability to home specifically to the large intestine. The ability of the in vitro methods described herein to increase GPR15 expression has also been shown at the level of the individual cell. See, for example, FIG. 11. Increased GPR15 expression in a population of T cells so generated enables the cells to home to the large intestine in a targeted manner, whereupon delivery of the population of T cells provides benefit to a subject in need thereof.

Particulars as to an exemplary protocol for generating Tregs having enhanced GPR15 expression and possessing the ability to home preferentially to the large intestine are set forth as follows:
1. Isolate mononuclear cells from buffy coats on a Ficoll-PAQUE gradient;
2. Use Miltenyi human CD4+ beads and procedure to isolate CD4+T cells;
3. Isolate CD4+CD3+CD25+CD127− cells by cell sorting. The majority of these cells are Treg cells and may thus, be referred to herein as a Treg-enriched population;
4. Count cells and resuspend in fresh serum-free media or RPMI with serum at a concentration of 250,000 to 500,000 cells per mL;
5. Add 100 U/ml of IL-2, 10-20 ng/mL of IL-21, 5-20 ng/ml of TGF-beta, 0.01-1 nM of retinoic acid, and anti-CD3/CD28 activation beads at a ratio of 1 bead per cell in U-bottom 96 well plates; and
6. Culture the cells for 3-7 days Particulars as to an exemplary protocol for generating CD4+ or CD8+ effector T cells having enhanced GPR15 expression and possessing the ability to home preferentially to the large intestine are set forth as follows:
1. Isolate mononuclear cells from buffy coats on a Ficoll-PAQUE gradient;
2. Use Miltenyi human CD4+ beads and procedure to isolate CD4+T cells or Miltenyi human CD8+ beads and procedure to isolate CD8+T cells;
3. Isolate CD4+CD3+CD45RA+CD25-naiveT cells or CD8+ CD3+CD45RA+CD25−naive T cells by cell sorting;
4. Count cells and resuspend in fresh serum-free media or RPMI with serum at a concentration of 250,000 to 500,000 cells per mL;
5. Add 100 U/ml of IL-2, 1-20 ng/mL of IL-21 or IL-6 or IL-27, 0.5-20 ng/ml of TGF-beta, 0.01-10 nM of retinoic acid, and anti-CD3/CD28 activation beads at a ratio of 1 bead per cell in U-bottom 96 well plates; and
6. Culture the cells for 3-7 days With respect to TGF-beta (TGF-β), IL-21, IL-6, IL-27, and IL-2, nucleic and amino acid sequences relating to these components of the culture medium described herein, are presented in SEQ ID NOs: 13 and 14 (for human TGF-beta), SEQ ID NOs: 15-18 (for two different isoforms of human IL-21), SEQ ID NOs: 19 and 20 (for human IL-6), SEQ ID NOs: 21, 22, 23, and 24 (for human IL-27 subunit alpha and beta), and SEQ ID NOs: 25 and 26 (for human IL-2). More particularly, the nucleic and amino acid sequences for human TGF-beta are designated SEQ ID NOs: 13 and 14, respectively, herein. The nucleic and amino acid sequences for a first isoform of human IL-21 are designated SEQ ID NOs: 15 and 16, respectively, herein. The nucleic and amino acid sequences for a second isoform of human IL-21 are designated SEQ ID NOs: 17 and 18, respectively, herein. The nucleic and amino acid sequences for human IL-6 are designated SEQ ID NOs: 19 and 20, respectively, herein. The nucleic and amino acid sequences for human IL-27 subunit alpha are designated SEQ ID NOs: 21 and 22, respectively, herein. The nucleic and amino acid sequences for human IL-27 subunit beta are designated SEQ ID NOs: 23 and 24, respectively, herein. The nucleic and amino acid sequences for human IL-2 are designated SEQ ID NOs: 25 and 26, respectively, herein. The aforementioned sequences are presented in full in the Sequence Listing of the present application.

The structure of retinoic acid is as follows:

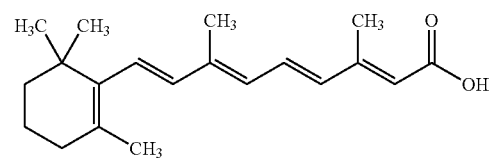 [SMILES: CC1=C(/C=C/C(C)=C/C=C/C(C)=C/C(=O)O)C(C)(C)CCC1]

Retinoic acid is commercially available and may, for example, be purchased from Sigma-Aldrich.

The anti-CD3/CD28 activation beads comprise anti-CD3 antibodies, which serve to activate TCR/CD3; and anti-CD28 antibodies, which serve to activate the TCR costimulator. The anti-CD3 and anti-CD28 antibodies are immobilized on beads provided in a Treg cell:bead ratio of about 1:1.

In an alternate embodiment, functional Treg cells can be generated in vitro in accordance with methods disclosed by Strainic et al. (2013, Nature Immunol 14:162-171; the entire content of which is incorporated herein in its entirety). Briefly, Strainic et al. determined that antagonism of G protein-coupled receptors for complement fragments C3a and C5a (C3aR and C5aR) induces functional human Treg cells. As described therein, naive human CD45RA+, CD25−, CD4+ T cells incubated for 3 days with anti-CD3, IL-2 and dendritic cells, plus pharmaceutical antagonists of C3aR and C5aR (C3aR-A and C5aR-A) or monoclonal antibody to C3a and monoclonal antibody to C5a became Foxp3+ and CD25+ (Treg markers) and exhibited robust suppression. Accordingly, the experimental protocol of Strainic et al. offers an alternative to isolating a population of CD4+CD3+CD25+T cells or CD4+CD3+CD25+CD127−T cells from a mammal as an initial step in the present methods and suggests that a population of CD4+CD3+CD25−T cells or CD4+CD3+CD25-CD127−T cells could be isolated initially and treated with antagonists of C3aR and C5aR or C3a or C5a either in advance of the instant method or in conjunction with the culture medium comprising the cocktail of cytokines and compounds described herein.

It is, moreover, noteworthy that prior to the findings presented herein, the inclusion of retinoic acid in any protocol designed to generate cells targeted to the large intestine was contraindicated based on prevailing thought in the field. As disclosed by Agace (2008, Trends in Immunology 29(11): 514-522; the entire content of which is incorporated herein by reference), for example, experimental results provided evidence that vitamin A signaling and, by extension retinoic acid, was not required for the generation of "colon homing" lymphocyte populations. The prevailing thought in the field was underscored by Mora et al. (2008, Nature 8:685-698; the entire content of which is incorporated herein by reference) who disclosed that although vitamin deficiency decreases the number of T and B cells in the small bowel lamina propria, it does not affect lymphocyte migration to the colon. Mora et al. concluded that retinoic acid is neither necessary nor sufficient to imprint colon-homing lymphocytes. Given the above, the present inventors' appreciation that retinoic acid contributes to induction of large intestine specific lymphocyte homing, but only in conjunction with the aforementioned cocktail of cytokines, is surprising.

Accordingly, methods described herein may be used to generate T cell populations (e.g., Treg and Teff cell populations) having enhanced GPR15 expression and thus, by virtue of this structural feature, possess the ability to home preferentially to the large intestine. T cell populations so generated may also optionally have enhanced integrin $\alpha 4\beta 7$. The combined structural features of enhanced expression of GPR15 and integrin $\alpha 4\beta 7$ in T cell populations so generated confers upon these populations the ability to extravasate from the bloodstream preferentially to the large intestine. Accordingly, such structural/functional features imbue these T cell populations with a targeting potential that can be used to advantage to deliver therapeutic relief preferentially to the primary site of disease manifestation in a subject in need thereof. In the present context, the primary site of disease manifestation in subjects in need thereof is the large intestine.

Administering T Cell Populations Having Enhanced GPR15 Expression and Ability to Preferentially Migrate to the Large Intestine Studies with effector CD4 T cells have found that infusions of $1\times10^9$ to $1\times10^{10}$ cells are required to affect CD4 T cell homeostasis (June et al. 2006, Semin. Immunol. 18:78-88; the entire content of which is incorporated herein by reference). Accordingly, it is envisioned that a similar number of Treg cells may be required for systemic Treg mediated immunosuppression. With regard to the present methods, however, fewer T cells having enhanced GPR15 expression and ability to migrate preferentially to the large intestine, as described herein and generated in accordance with methods set forth herein, may be required to achieve clinical benefit due to the preferential homing of these cells directly to the particular site of disease manifestation, namely the large intestine.

Additional aspects pertaining to methods for expanding Tregs and administration thereof for the purposes of treating diseases or conditions associated with impaired Treg activity in a subject are known in the art. Such conditions include graft versus host disease (GVHD) and autoimmune disorders, diseases, and conditions. The following references are cited as exemplary of the field and the entire content of each of which is incorporated herein by reference: Tang et al. (2012, J Mol Cell Biol 4(1):11-21); Safinia et al. (2010, Curr Opin Organ Transplantation 15:427-434); Riley et al. (2009, Immunity 30(5):656-665); Golovina et al. (2008, J Immunol 181(4): 2855-2868); Basu et al. (2008, J Immunol. 180:5794-5798); Tang et al. (2006, Immunol Rev 212:217-237); Battaglia et al. (2005, Blood 105:4743-4748); Godfrey et al. (2005, Blood 105:750-758); and Godfrey et al. (2004, Blood 104:453-461).

Further to the above, three trials of Treg therapy for GVHD in patients have been reported Trzonkowski et al. (2009, Clin Immmunol 133:22-26); Brunstein et al. (2010, Blood 117: 1061-1070); and Di Ianni et al. (2011, Blood 117:3921-3928), the entire content of each of which is incorporated herein by reference. Trzonkowski et al. (2009) performed the first-in-man trial, which involved two patients. The first patient, who suffered from chronic GVHD two years after transplantation, was treated with $0.1\times10^6$/kg FACs purified ex vivo expanded Tregs isolated from the donor. After treatment, the patient's symptoms subsided and the patient was successfully withdrawn from immuno suppression. The second patient had acute disease that progressed, despite a cumulative dose of $3\times10^6$/kg expanded Tregs. Brunstein et al. (2010) performed a larger scale phase I trial that evaluated the effect of Treg transplant in patients with advanced hematologic malignancy. Tregs were isolated using anti-CD25 immunomagnetic bead selection from third-party cord blood samples that were matched for 4-6 HLA loci with the recipient. Up to $6\times10^6$/kg Tregs, expanded ex vivo using anti-CD3 and anti-CD29 conjugated beads, were infused. The incidence of severe acute GVHD was significantly reduced in patients receiving Treg therapy. No dose-limiting toxicity or increases in adverse events were observed in these patients. In a third trial, Di Ianni et al. (2011) enrolled patients with high-risk hematological malignancies who received anti-CD25 immunomagnetic bead-enriched donor Tregs without ex vivo expansion prior to receiving one haplo-mismatched hematopoietic stem cell and Tconventional (Tconv) cell transplants from the same donors. Most patients received $2\times10^6$/kg Tregs with $1\times10^6$/kg Tconv cells and no adjunct immunosuppression was administered post-transplant. Patients receiving Tregs exhibited accelerated immune reconstitution, reduced viral reactivation, and a lower incidence of tumor relapse and GVHD. See also Tang et al. (2012, J Mol Cell Biol 4(1):11-21), the entire content of which is incorporated herein by reference.

A protocol that calls for evaluation of FACS-based isolation of high-yield CD4+CD25+CD127$^{lo}$ Tregs for ex vivo expansion of highly pure Tregs has recently been approved for a phase I safety trial in type I diabetic patients (NCT01210664). This trial is active and no longer recruiting.

Additional methods for generating Treg cell populations and methods of using same for therapeutic purposes are known in the art and described, for example, in U.S. Pat. Nos. 8,241,621 and 6,281,012; and U.S. Patent Application Nos. 2006/0233751, 2006/0062763, 2006/0115899, 20110300119, and 20110268752 (the entire content of each of which is incorporated herein by reference).

Accordingly, it is envisioned that a population of $0.5\times10^7$ to $1\times10^{10}$ CD4+CD3+CD25+ T cells or CD4+CD3+CD25+CD127− T cells having enhanced GPR15 expression and ability to migrate preferentially to the large intestine (GPR15+ Tregs) would confer clinical benefit to a mammal afflicted with an inflammatory condition of the large intestine. In view of evidence presented herein, such cell populations will act as Tregs to suppress ongoing deleterious immune responses in the large intestine. Exemplary such inflammatory conditions include, without limitation, inflammatory bowel disease, idiopathic colitis, and infectious colitis. Crohn's disease and ulcerative colitis are, moreover, set forth herein and understood in the art to be exemplary types of inflammatory bowel disease.

Further to the above, it is envisioned that a population of $0.5 \times 10^7$ to $1 \times 10^{10}$ CD4+ or CD8+ effector T cells having enhanced GPR15 expression and ability to migrate preferentially to the large intestine (GPR15+ Teff cells) would confer clinical benefit to a mammal afflicted with a cancer or infection of the large intestine. In accordance with results presented herein, such populations of Teff cells would promote immune responses in a localized fashion, namely in the large intestine, wherein such immune responses would be directed to the cancer cells or infectious agents (e.g., bacteria, virus). Cancers of the colon include, without limitation, colon cancer, colorectal cancer, and cancers that have metastasized to the large intestine. Infections of the large intestine treatable using these methods include, without limitation, bacterial and viral infections. Exemplary bacterial infections include those caused by foodborne *E. coli* contamination.

Agents

Also encompassed herein are methods for screening to identify agents that can modulate GPR15 activity. Such agents may alter GPR15 expression and/or function and thus, modulate GPR15 activity. Such modulatory agents may enhance or promote GPR15 expression or function in a population of T cells and accordingly, may be referred to herein as GPR15 activators. Alternatively, such modulatory agents may reduce or inhibit GPR15 expression or function in a population of T cells and thus, may be referred to herein as GPR15 inhibitors. Methods for screening potential candidate agents to identify modulators of GPR15 expression or activity may be performed using a population of T cells isolated from a mammal or generated in culture. Such populations may have enhanced GPR15 expression and ability to migrate preferentially to the large intestine and have been generated using a method described herein.

As used herein, an "agent", "candidate compound", or "test compound" may be used to refer to, for example, nucleic acids (e.g., DNA and RNA), carbohydrates, lipids, proteins, peptides, peptidomimetics, small molecules and other drugs. More particularly an agent may refer to retinoid derivative compounds, short hairpin RNA (shRNA), small interfering RNA (siRNA), neutralizing and/or blocking antibodies, tryptophan derivative compounds, Vitamin D derivatives, or molecules known to inhibit fever, or inflammation.

Exemplary agents include anti-GPR15 antibodies that, for example, block engagement of GPR15 with its ligand or ligands or prevent downstream signaling of either or both of GPR15 and its ligand or ligands following engagement. Small molecule inhibitors and activators of GPR15 signaling are also envisioned herein.

A short hairpin RNA (shRNA) is a sequence of RNA that makes a tight hairpin turn that can be used to silence gene expression via RNA interference. shRNA is generally expressed using a vector introduced into cells, wherein the vector utilizes the U6 promoter to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs that match the siRNA to which it is bound.

Small interfering RNA (siRNA), sometimes known as short interfering RNA or silencing RNA, are a class of 20-25 nucleotide-long double-stranded RNA molecules that play a variety of roles in biology. Most notably, siRNA is involved in the RNA interference (RNAi) pathway whereby the siRNA interferes with the expression of a specific gene.

As described herein, an agent identified using the method of the present invention that is a "modulator of GPR15 activity" is defined as an agent that is capable of modulating (e.g., increasing or decreasing) GPR15 expression or function. Such an agent may be identified by its ability to alter directly GPR15 expression and/or function or to effect a change in the expression/function of a gene downstream of GPR15 signaling. Based on results presented in FIG. 2, for example, G$\alpha$i is downstream of GPR15 as evidenced by the fact that blocking G$\alpha$i gene function prevents GPR15 signaling.

As detailed below, experimental protocols of utility in determining expression of genes/proteins downstream of GPR15 signaling and relative expression levels are described herein and are understood in the art. Such experimental protocols, include, but are not limited to, real-time PCR using appropriate primers.

As taught herein, the change effected by an agent that is a modulator of GPR15 activity in T cells is determined relative to that of a population of T cells incubated in parallel in the absence of the agent or in the presence of a control agent (as described below), either of which is analogous to a negative control condition.

In accordance with the present invention, the method described herein may be used to achieve an increase in the number of T cells in a cell population incubated in, for example, GPR15 expression promoting conditions, as described herein. An increase in the number of GPR15 expressing cells in such a cell population may be expressed as the percent (%) of GPR15+ T cells present in such a cell population relative to the total number of cells. In accordance with the present invention, the method described herein typically achieves 50% GPR15+ T cells in a cell population. It will be appreciated, however, that the present method may be used to achieve a higher relative percent of GPR15+ T cells in a cell population, particularly if the method described herein is performed in the presence of a GPR15 modulatory agent that enhances GPR15 expression (GPR15 activator). Accordingly, the present invention is not in any way limited to achieving 50% GPR15+ T cells in a treated cell population and encompasses T cell populations treated or generated in accordance with methods presented herein that comprise equal to or greater than 10%, 20%, 30%, 40%, 50%, 60%, 70%, 80%, 90%, 95%, 96%, 97%, 98%, or 99% GPR15+ T cells. In still more particular embodiments, T cell populations treated or generated in accordance with methods presented herein are 100% GPR15+ T cell populations.

In light of the above, it will be appreciated that an agent identified using the method of the present invention that is a "modulator of GPR15 expression" may be identified by its ability to effect a change in the percent of GPR15 expressors in a population of T cells incubated, for example, in GPR15 expression promoting conditions. As indicated herein above, a change in the percent of GPR15+ T cells in a population of T cells incubated in the presence of an agent is determined relative to the percent of GPR15+ T cells in a population of T cells incubated in the absence of the agent or in the presence of a control agent (negative control condition).

The term "control substance", "control agent", or "control compound" as used herein refers a molecule that is inert or has no activity relating to an ability to modulate a biological activity. With respect to the present invention, such control substances are inert with respect to an ability to modulate GPR15 expresssion. Exemplary controls include, but are not limited to, solutions comprising physiological salt concentrations.

In accordance with the present invention, incubation in the presence of an agent that results in a decrease in GPR15 expression or a gene/protein that positively regulates GPR15 signaling, such as IL-21, IL-6, IL-27, or TGF-β, indicates that the agent is an inhibitor of GPR15 activity. An inhibitor of GPR15 activity is an agent that effects at least a 2-fold or at least a 3-fold decrease in the expression of GPR15 or a gene/protein that positively regulates GPR15 signaling, such as IL-21, IL-6, IL-27, or TGF-β. The above fold decreases may be determined relative to expression levels induced by incubation in GPR15 promoting conditions in the absence of the agent.

In accordance with the present invention, incubation in the presence of an agent that results in an increase in GPR15 expression or a gene/protein that positively regulates GPR15 signaling, such as IL-21, IL-6, IL-27, or TGF-β, indicates that the agent is an activator/promoter of GPR15 activity. An activator of GPR15 activity is an agent that effects at least a 2-fold or at least a 3-fold increase in the expression of GPR15 or a gene/protein that positively regulates by GPR15 signaling, such as IL-21, IL-6, IL-27, or TGF-β. The above fold increases may be determined relative to expression levels induced by incubation in GPR15 promoting conditions in the absence of the agent.

It is to be understood that agents capable of modulating GPR15 expression, as determined using in vitro methods described herein, are likely to exhibit similar modulatory capacity in applications in vivo.

Modulatory agents identified using the screening methods of the present invention and compositions thereof can thus be administered for therapeutic treatments. In therapeutic applications, modulatory agents that promote GPR15 expression levels on Treg cells, for example, and compositions thereof are administered to a patient suffering from an inflammatory or autoimmune disorder of the large intestine in an amount sufficient to at least partially arrest a symptom or symptoms of the disease and its complications. An amount adequate to accomplish this is defined as a "therapeutically effective amount or dose." Amounts effective for this use will depend on the severity of the disease and the weight and general state of the patient.

Examples of inflammatory or autoimmune disorders that may be treated using activators/promoters of GPR15 expression on Treg cells include, without limitation, inflammatory bowel disease (e.g., Crohn's disease, and ulcerative colitis).

In alternative therapeutic applications, modulatory agents that promote GPR15 expression levels on CD4+ or CD8+ Teff cells, for example, and compositions thereof are administered to a patient suffering from a cancer or infection of the large intestine in an amount sufficient to at least partially arrest a symptom or symptoms of the disease and its complications. An amount adequate to accomplish this is defined as a "therapeutically effective amount or dose." Amounts effective for this use will depend on the severity of the disease and the weight and general state of the patient.

Examples of cancers that may be treated using activators/promoters of GPR15 expression on Teff cells include, without limitation, colon cancer and cancers that have metastasized to the large intestine (e.g., ovarian cancer). Examples of infections of the large intestine that may be treated using activators/promoters of GPR15 expression on Teff cells include, without limitation, foodborne bacterial and viral infections, such as, for example, certain strains of E. coli.

Methods for Determining Expression Levels of GPR15 and Other T Cell Subset Markers Based on the guidance presented herein and knowledge in the relevant scientific fields, the expression level of cellular markers, such as, for example, GPR15, integrin α4β7, or CCR9, can be determined using a variety of techniques. Exemplary markers of human Treg cells include, but are not limited to, CD25, Glycoprotein A repetitions predominant (GARP), or Latency-associated peptide (LAP), CD3, CD4, and FoxP3. Of these, CD25, GARP, and LAP are Treg specific markers. Expression of CD127, on the other hand, is negatively correlated with human Treg cells. Exemplary markers of human Teff cells include, but are not limited to, CD3, CD4 or CD8. Expression of GARP, and LAP, on the other hand, is negatively correlated with human Teff cells.

Expression levels of such markers (either a positive or a negative marker) may be assessed with respect to expressed nucleic acid corresponding to a cell marker (e.g., mRNA, total RNA) or with respect to polypeptides encoded by same. A variety of standard protocols may be used to determine, for example, RNA level, including, but not limited to: polymerase chain amplification and detection of amplified products therefrom, ribonuclease protection (RNase protection) assay, and Northern blot analysis. The principles and general procedures of each of these methods are described in, for example, Dvorak et al. (Biomed Papers 147:131, 2003), which is incorporated herein in its entirety. The principles and general procedures of each of these methods are, moreover, known in the art. In a particular embodiment of the invention, real-time PCR is used to detect gene expression of cellular markers of interest.

A variety of protocols are available for measuring and/or detecting expression levels of polypeptides. Protocols for detecting polypeptide expression, such as, for example, immunohistochemistry and immunoblotting, are known in the art. These protocols are generally applicable to detecting polypeptides, such as the cellular markers listed herein above. Particular methods for detecting these polypeptides are described in the Examples presented herein, as are reagents for performing such methods.

In general, immunoassays for polypeptides typically comprise contacting a sample, such as a population of cells (e.g., incubated in GPR15 expression promoting conditions or lysates thereof) in the presence of an antibody that specifically or selectively binds to a polypeptide in question, e.g., a detectably labeled antibody capable of identifying, the particular polypeptide (e.g., GPR15 or integrin α4β7), and detecting the bound antibody by any of a number of techniques well-known in the art (e.g., Western blot, ELISA, FACS).

The biological sample may be brought in contact with and immobilized onto a solid phase support or carrier such as nitrocellulose, or other solid support that is capable of immobilizing cells, cell particles or soluble proteins. The support may then be washed with suitable buffers followed by treatment with the detectably labeled antibody that selectively or specifically binds to the particular polypeptide (e.g., GPR15 or integrin α4β7). The solid phase support may then be washed with the buffer a second time to remove unbound antibody. The amount of bound label on a solid support may then be detected by conventional means.

More particularly, GPR15 or integrin α4β7 protein levels can be assessed by cell surface staining, ELISA, intracellular staining for proteins regulated or modified as a result of GPR15 or integrin α4β7 downstream signaling, and Western Blot.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Particular supports include polystyrene beads. Those skilled in the art will know many other suitable carriers for binding antibody or antigen, or will be able to ascertain the same by use of routine experimentation.

An antibody can be detectably labeled by linking same to an enzyme and using the labeled antibody in an enzyme immunoassay (EIA) (Voller, A., "The Enzyme Linked Immunosorbent Assay (ELISA)", 1978, *Diagnostic Horizons* 2:1, Microbiological Associates Quarterly Publication, Walkersville, Md.); Voller, A. et al., 1978, *J. Clin. Pathol.* 31: 507-520; Butler, J. E., 1981, *Meth. Enzymol.* 73:482; Maggio, E. (ed.), 1980, *Enzyme Immunoassay*, CRC Press, Boca Raton, Fla.; Ishikawa, E. et al., (eds.), 1981, *Enzyme Immunoassay*, Kgaku Shoin, Tokyo). The enzyme that is bound to the antibody reacts with an appropriate substrate, particularly a chromogenic substrate, in such a manner as to produce a chemical moiety detectable, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods that employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect a polypeptide through the use of a radioimmunoassay (RIA). The radioactive isotope can be detected by such means as the use of a gamma counter or a scintillation counter or by autoradiography.

An antibody may also be labeled with a fluorescent compound. When the fluorescently labeled antibody is exposed to light of the proper wavelength, its presence can be detected due to fluorescence emission. Among the most commonly used fluorescent labeling compounds are fluorescein isothiocyanate, rhodamine, phycoerythrin, phycocyanin, allophycocyanin, o-phthaldehyde and fluorescamine.

An antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

An antibody can also be detectably labeled by coupling it to a chemiluminescent compound. The presence of the chemiluminescent-tagged antibody is determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label an antibody. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The basic molecular biology techniques used to practice the methods of the invention are well known in the art, and are described for example in Sambrook et al., 1989, *Molecular Cloning: A Laboratory Manual*, Cold Spring Harbor Laboratory, New York; Ausubel et al., 1988, *Current Protocols in Molecular Biology*, John Wiley & Sons, New York; and Ausubel et al., 2002, *Short Protocols in Molecular Biology*, John Wiley & Sons, New York).

Agents Identified by the Screening Methods of the Invention

The invention provides methods for identifying agents (e.g., candidate compounds or test compounds) that modulate (inhibit or promote) GPR15 expression either on the level of an individual cell or with reference to a population of T cells. Agents that are capable of promoting GPR15 expression on Tregs, for example, as identified by a screening method of the invention, are useful as candidate anti-inflammatory or anti-autoimmune disorder therapeutics for disorders of the large intestine.

A list of inflammatory or anti-autoimmune disorders that may be treated using an agent identified using a method of the invention includes, without limitation: inflammatory bowel disease, idiopathic colitis, and infectious colitis. Inflammatory bowel diseases of the large intestine treatable using agents identified by the present methods include Crohn's disease and ulcerative colitis.

Agents that are capable of promoting GPR15 expression on Teff cells, for example, as identified by a screening method of the invention, are useful as candidate anti-cancer or anti-infection therapeutics for disorders of the large intestine.

A list of cancers or infectious diseases that may be treated using an agent identified using a method of the invention includes, without limitation: colon cancer, colorectal cancer, and other cancers that metastasize to the large intestine and bacterial or viral infections of the large intestine.

Examples of agents, candidate compounds or test compounds include, but are not limited to, nucleic acids (e.g., DNA and RNA), carbohydrates, lipids, proteins, peptides, peptidomimetics, small molecules and other drugs. Agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des. 12:145; U.S. Pat. No. 5,738,996; and U.S. Pat. No. 5,807,683, each of which is incorporated herein in its entirety by reference).

Examples of methods for the synthesis of molecular libraries can be found in the art, for example in: DeWitt et al. (1993) Proc. Natl. Acad. Sci. USA 90:6909; Erb et al. (1994) Proc. Natl. Acad. Sci. USA 91:11422; Zuckermann et al. (1994) J.

Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233, each of which is incorporated herein in its entirety by reference.

Libraries of compounds may be presented, e.g., presented in solution (e.g., Houghten (1992) Bio/Techniques 13:412-421), or on beads (Lam (1991) Nature 354:82-84), chips (Fodor (1993) Nature 364:555-556), bacteria (U.S. Pat. No. 5,223,409), spores (U.S. Pat. Nos. 5,571,698; 5,403,484; and 5,223,409), plasmids (Cull et al. (1992) Proc. Natl. Acad. Sci. USA 89:1865-1869) or phage (Scott and Smith (19900 Science 249:386-390; Devlin (1990) Science 249:404-406; Cwirla et al. (1990) Proc. Natl. Acad. Sci. USA 87:6378-6382; and Felici (1991) J. Mol. Biol. 222:301-310), each of which is incorporated herein in its entirety by reference.

Therapeutic Uses of Agents Identified

The invention provides for treatment of inflammatory and/or autoimmune disorders by administration of a therapeutic agent identified using the above-described methods designed to screen for agents that enhance GPR15 expression in Treg cells. Administration of a therapeutic agent identified using methods designed to screen for agents that enhance GPR15 expression in Teff cells may also be used advantageously for the treatment of a cancer or infection of the large intestine. Such agents include, but are not limited to proteins, peptides, protein or peptide derivatives or analogs, antibodies, nucleic acids, and small molecules.

Accordingly, the invention provides methods for treating patients afflicted with an inflammatory and/or autoimmune disorder of the large intestine comprising administering to a subject an effective amount of a compound that promotes expression of GPR15 on Treg cells, as identified by the method of the invention. Alternatively, methods are provided for treating patients afflicted with a cancer or infection of the large intestine comprising administering to a subject an effective amount of a compound that promotes expression of GPR15 on Teff cells, as identified by the method of the invention. In a particular aspect, the compound is substantially purified (e.g., substantially free from substances that limit its effect or produce undesired side-effects).

The subject is particularly an animal, including but not limited to animals such as cows, pigs, horses, chickens, cats, dogs, etc., and is more particularly a mammal, and most particularly a human. In a specific embodiment, a non-human mammal is the subject.

Formulations and methods of administration that can be employed when the compound comprises a nucleic acid are described above; additional appropriate formulations and routes of administration are described below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu (1987) J. Biol. Chem. 262:4429-4432), and construction of a nucleic acid as part of a retroviral or other vector. Methods of introduction can be enteral or parenteral and include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In a particular embodiment, the compounds may be introduced directly into the large intestine using tools routinely used for colonoscopy and the like. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally, e.g., by local infusion during surgery, topical application, e.g., by injection, by means of a catheter, or by means of an implant, said implant being of a porous, non-porous, or gelatinous material, including membranes, such as sialastic membranes, or fibers.

In another embodiment, the compound can be delivered in a vesicle, in particular a liposome (see Langer (1990) Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound can be delivered in a controlled release system. In one embodiment, a pump may be used (see Langer, supra; Sefton (1987) CRC Crit. Ref. Biomed. Eng. 14:201; Buchwald et al. (1980) Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., 1983, Macromol. Sci. Rev. Macromol. Chem. 23:61; see also Levy et al. (1985) Science 228:190; During et al. (1989) Ann. Neurol. 25:351; Howard et al. (1989) J. Neurosurg. 71:105). In yet another embodiment, a controlled release system can be placed in proximity of the therapeutic target, e.g., an inflammatory site, thus requiring only a fraction of the systemic dose (see, e.g., Goodson, in Medical Applications of Controlled Release, supra, vol. 2, pp. 115-138 (1984)). Other controlled release systems are discussed in the review by Langer (1990, Science 249:1527-1533).

Pharmaceutical Compositions

The present invention also provides pharmaceutical compositions. Such compositions comprise a therapeutically effective amount of an agent or a population of cells as decribed herein and a pharmaceutically acceptable carrier. In a particular embodiment, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin, incorporated in its entirety by reference herein. Such compositions will contain a therapeutically effective amount of the compound, preferably in purified form, together with a suitable amount of carrier so as to provide the form for proper administration to the subject. The formulation should suit the mode of administration.

In a particular embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment of an inflammatory or autoimmune disorder (e.g., Crohn's disease) can be determined by standard clinical techniques based on the present description. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Suppositories generally contain active ingredient in the range of 0.5% to 10% by weight; oral formulations preferably contain 10% to 95% active ingredient. Effective doses may be extrapolated from dose-response curves derived from in vitro or animal model test systems.

Nucleic Acids

The invention provides methods for identifying agents capable of modulating GPR15 expression. Accordingly, the invention encompasses administration of a nucleic acid encoding a peptide or protein capable of modulating GPR15 expression, as well as antisense sequences or catalytic RNAs capable of interfering with GPR15 expression.

The invention further encompasses transfection/transduction of nucleic acid sequences encoding GPR15 into T cell populations ex vivo to confer enhanced GPR15 expression thereto. In a particular embodiment, T cell populations are also transfected/transduced with nucleic acid sequences encoding α4 integrin and β7 integrin to confer enhanced α4β7 integrin expression. In a particular embodiment, the T cell population isolated from a donor subject and transfected/transduced ex vivo is positively selected for enhanced GPR15 expression (and potentially enhanced α4β7 integrin expression) prior to administration to a recipient. In a further aspect, nucleic acid sequences that confer selection (via, e.g, drug resistance), in vitro and/or in vivo visualization/detection (e.g., fluorescence), or inducible cell death (via, e.g., triggering apoptosis) of transfected/transduced cells are cotransfected/cotransduced with nucleic acid sequences encoding GPR15 and, optionally, α4 and β7 integrins.

With respect to triggering death of transplanted cells in a subject following transplantation, Di Stasi et al. (2011, N Engl J Med 365(18):1673-1683; the entire content of which is incorporated herein by reference) have, for example, developed an inducible T cell "safety switch" based on the fusion of human caspase 9 to a modified form of human FK-binding protein, inclusion of which facilitates conditional dimerization. When exposed to a synthetic dimerizing drug, the inducible caspase 9 (iCasp9) is activated by dimerization of the FK-binding component of the fusion protein and iCasp9 activation leads to rapid cell death of cells expressing the fusion protein construct. The T cell safety switch has been tested by introducing the gene encoding the fusion protein into donor T cells administered to enhance immune reconstitution in recipients of haploidentical stem-cell transplants. Di Stasi et al. demonstrated that administration of AP1903, an otherwise bioinert small-molecule dimerizing drug, to patients wherein GVHD developed led to rapid eliminaton of greater than 90% of the transplanted genetically modified T cells.

Any suitable methods for administering a nucleic acid sequence available in the art can be used according to the present invention.

Methods for administering and expressing a nucleic acid sequence are generally known in the area of gene therapy. For general reviews of the methods of gene therapy, see Goldspiel et al. (1993) Clinical Pharmacy 12:488-505; Wu and Wu (1991) Biotherapy 3:87-95; Tolstoshev (1993) Ann. Rev. Pharmacol. Toxicol. 32:573-596; Mulligan (1993) Science 260:926-932; and Morgan and Anderson (1993) Ann. Rev. Biochem. 62:191-217; May (1993) TIBTECH 11(5): 155-215. Methods commonly known in the art of recombinant DNA technology which can be used in the present invention are described in Ausubel et al. (eds.), 1993, Current Protocols in Molecular Biology, John Wiley & Sons, NY; and Kriegler (1990) Gene Transfer and Expression, A Laboratory Manual, Stockton Press, NY.

In a particular aspect, the compound comprises a nucleic acid encoding a peptide or protein capable of modulating GPR15 expression, such nucleic acid being part of an expression vector that expresses the peptide or protein in a suitable host. In particular, such a nucleic acid has a promoter operably linked to the coding region, said promoter being inducible or constitutive (and, optionally, tissue-specific). In another particular embodiment, a nucleic acid molecule is used in which the coding sequences and any other desired sequences are flanked by regions that promote homologous recombination at a desired site in the genome, thus providing for intrachromosomal expression of the nucleic acid (Koller and Smithies (1989) Proc. Natl. Acad. Sci. USA 86:8932-8935; Zijlstra et al. (1989) Nature 342:435-438).

Delivery of the nucleic acid into a subject may be direct, in which case the subject is directly exposed to the nucleic acid or nucleic acid-carrying vector; this approach is known as in vivo gene therapy. Alternatively, delivery of the nucleic acid into the subject may be indirect, in which case cells are first transformed with the nucleic acid in vitro and then transplanted into the subject, known as "ex vivo gene therapy".

In another embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286); by direct injection of naked DNA; by use of microparticle bombardment (e.g., a gene gun; Biolistic, Dupont); by coating with lipids, cell-surface receptors or transfecting agents; by encapsulation in liposomes, microparticles or microcapsules; by administering it in linkage to a peptide which is known to enter the nucleus; or by administering it in linkage to a ligand subject to receptor-mediated endocytosis (see, e.g., Wu and Wu, 1987, J. Biol. Chem. 262:4429-4432), which can be used to target cell types specifically expressing the receptors.

In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932-8935; Zijlstra et al. (1989) Nature 342:435-438).

In a further embodiment, a retroviral vector can be used (see Miller et al. (1993) Meth. Enzymol. 217:581-599). These retroviral vectors have been modified to delete retroviral sequences that are not necessary for packaging of the viral genome and integration into host cell DNA. The nucleic acid encoding a desired polypeptide to be used in gene therapy is cloned into the vector, which facilitates delivery of the gene into a subject. More detail about retroviral vectors can be found in Boesen et al. (1994) Biotherapy 6:291-302, which describes the use of a retroviral vector to deliver the mdrl gene to hematopoietic stem cells in order to make the stem cells more resistant to chemotherapy. Other references illustrating the use of retroviral vectors in gene therapy are: Clowes et al. (1994) J. Clin. Invest. 93:644-651; Kiem et al. (1994) Blood 83:1467-1473; Salmons and Gunzberg (1993) Human Gene Therapy 4:129-141; and Grossman and Wilson (1993) Curr. Opin. in Genetics and Devel. 3:110-114.

Adenoviruses may also be used effectively in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson (1993) Current Opinion in Genetics and Development 3:499-503 present a review of adenovirus-based gene therapy. Bout et al. (1994) Human Gene Therapy 5:3-10 demonstrated the use of adenovirus vectors to transfer genes to the respiratory epithelia of rhesus monkeys. Other instances of the use of adenoviruses in gene therapy can be found in Rosenfeld et al. (1991) Science 252:431-434; Rosenfeld et al. (1992) Cell 68:143-155; Mastrangeli et al. (1993) J. Clin. Invest. 91:225-234; PCT Publication WO94/12649; and Wang, et al. (1995) Gene Therapy 2:775-783. Adeno-associated virus (AAV) has also been proposed for use in gene therapy (Walsh et al. (1993) Proc. Soc. Exp. Biol. Med. 204:289-300; U.S. Pat. No. 5,436,146).

Another suitable approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr (1993) Meth. Enzymol. 217:599-618; Cohen et al. (1993) Meth. Enzymol. 217:618-644; Cline (1985) Pharmac. Ther. 29:69-92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a subject by various methods known in the art. In a particular embodiment, epithelial cells are injected, e.g., subcutaneously. In another embodiment, recombinant skin cells may be applied as a skin graft onto the subject; recombinant blood cells (e.g., hematopoietic stem or progenitor cells) are preferably administered intravenously. The amount of cells envisioned for use depends on the desired effect, the condition of the subject, etc., and can be determined by one skilled in the art.

Cells into which a nucleic acid can be introduced for purposes of gene therapy encompass any desired, available cell type, and include but are not limited to neuronal cells, glial cells (e.g., oligodendrocytes or astrocytes), epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood or fetal liver. In a particular embodiment, the cell used for gene therapy is autologous to the subject that is treated.

In another embodiment, the nucleic acid to be introduced for purposes of gene therapy may comprise an inducible promoter operably linked to the coding region, such that expression of the nucleic acid is controllable by adjusting the concentration of an appropriate inducer of transcription.

Direct injection of a DNA coding for a peptide or protein capable of modulating GPR15 expression may also be performed according to, for example, the techniques described in U.S. Pat. No. 5,589,466. These techniques involve the injection of "naked DNA", i.e., isolated DNA molecules in the absence of liposomes, cells, or any other material besides a suitable carrier. The injection of DNA encoding a protein and operably linked to a suitable promoter results in the production of the protein in cells near the site of injection.

GPR15+Enriched Populations of Human Treg and Teff Cells

The novel methods of the present invention facilitate the generation of a GPR15+ enriched population of human Treg cells comprising about or at least $10^6$ to $10^9$ human Treg cells, wherein the population of human Treg cells expresses CD4, CD3, CD25, GPR15, and optionally integrin α4β7. Such populations may comprise equal to or greater than 10%, 20%, 30%, 40%, 50%, 60%, 70%, 80%, 90%, 95%, 96%, 97%, 98%, or 99% GPR15+ human Treg cells. Such populations may comprise 100% GPR15+ human Treg cells. Such populations may also express Glycoprotein A repetitions predominant (GARP), and Latency-associated peptide (LAP). In particular embodiments, GPR15+ human T reg cells do not express CCR9, the absence of which may be achieved by a further selection step to remove CCP+ cells from the population of cells. Also encompassed herein are compositions comprising such populations of GPR15+ enriched Treg cells, as well as methods of using same for therapeutic purposes, GPR15+ enriched Treg cells and compositions thereof for use in treating an inflammatory condition of the large intestine, and use of GPR15+ enriched Treg cells and compositions thereof in the preparation of a medicament administrable to a subject afflicted with an inflammatory condition of the large intestine.

The novel methods of the present invention also facilitate the generation of a GPR15+ enriched population of human Teff cells comprising about or at least $10^6$ to $10^9$ human Teff cells, wherein the population of human Teff cells is either CD4+CD3+GPR15+ or CD8+CD3+GPR15+. Such populations also optionally express integrin α4β7. Such populations may comprise equal to or greater than 10%, 20%, 30%, 40%, 50%, 60%, 70%, 80%, 90%, 95%, 96%, 97%, 98%, or 99% GPR15+ human Teff cells. Such populations may comprise 100% GPR15+ human Teff cells. Such populations may also be selected for absence of expression of Glycoprotein A repetitions predominant (GARP−), Latency-associated peptide (LAP−), and/or CCR9 (CCR9−). Also encompassed herein are compositions comprising such populations of GPR15+ enriched Teff cells, as well as methods of using same for therapeutic purposes, GPR15+ enriched Teff cells and compositions thereof for use in treating a cancer or infection (e.g., a bacterial or viral infection) of the large intestine, and use of GPR15+ enriched Teff cells and compositions thereof in the preparation of a medicament administrable to a subject afflicted with a cancer or infection (e.g., a bacterial or viral infection) of the large intestine.

To further define GPR15$^+$ cells with respect to functionality, the present inventors analyzed the transcriptomes of GFP$^-$ and GFP$^+$CD4$^+$ T cells from the LILP by microarray (Table S1). It is noteworthy that many of the genes highly expressed in GFP$^+$ cells, as compared to those of GFP$^-$ cells, were characteristic of FOXP3$^+$ Treg cells, including Foxp3 (23), Eos (24), Il-10 (25), Cd25 (26)).

TABLE S1

Affymetrix gene chip analysis between GFP$^+$ and GFP$^-$ CD4$^+$ T cells from LILP of Gpr15$^{gfp/+}$ mice.

| Systematic | Gene Title | Gene Symbol | Fold change | Ttest p | Genbank |
|---|---|---|---|---|---|
| 1418365_at | cathepsin H | Ctsh | 15.23 | 0.04 | NM_007801 |
| 1437250_at | melanoregulin | Mreg | 12.31 | 0.03 | AV298358 |
| 1421957_a_at | phosphate cytidylyltransferase 1, choline, alpha isoform | Pcyt1a | 9.38 | 0.04 | NM_009981 |
| 1428034_a_at | tumor necrosis factor receptor superfamily, member 9 | Tnfrsf9 | 7.85 | 0.05 | BC028507 |
| 1433933_s_at | solute carrier organic anion transporter family, member 2b1 | Slco2b1 | 7.65 | 0.05 | BB553107 |
| 1425546_a_at | transferrin | Trf | 6.53 | 0.04 | AF440692 |
| 1451318_a_at | Yamaguchi sarcoma viral (v-yes-1) oncogene homolog///similar to Yam | Lyn///LOC676654 | 6.24 | 0.02 | M57697 |
| 1447541_s_at | integrin, alpha E, epithelial-associated | Itgae | 6.17 | 0.01 | AV210813 |
| 1420765_a_at | forkhead box P3 | Foxp3 | 5.98 | 0.00 | NM_054039 |
| 1451776_s_at | homeobox only domain | Hod | 5.65 | 0.05 | BC024546 |
| 1431296_at | G protein-coupled receptor 15 | Gpr15 | 5.54 | 0.05 | AA555873 |
| 1449216_at | integrin, alpha E, epithelial-associated | Itgae | 4.97 | 0.03 | NM_008399 |
| 1438365_x_at | lysosomal-associated protein transmembrane 4B | Laptm4b | 4.55 | 0.01 | BB560429 |
| 1426750_at | filamin, beta | Flnb | 4.34 | 0.02 | AW538200 |
| 1432669_at | RIKEN cDNA 9030420N05 gene | 9030420N05Rik | 4.05 | 0.04 | AK018521 |
| 1434225_at | SWA-70 protein | Swap70 | 4.03 | 0.00 | AV024531 |
| 1446957_s_at | cDNA sequence BC004022 | BC004022 | 3.36 | 0.03 | C81621 |
| 1428662_a_at | homeobox only domain | Hod | 3.33 | 0.01 | AK009007 |
| 1438011_at | phosphate cytidylyltransferase 1, choline, alpha isoform | Pcyt1a | 3.31 | 0.01 | BB280291 |
| 1449984_at | chemokine (C-X-C motif) ligand 2 | Cxcl2 | 3.19 | 0.04 | NM_009140 |
| 1428484_at | oxysterol binding protein-like 3 | Osbpl3 | 3.18 | 0.01 | AK004768 |
| 1437868_at | cDNA sequence BC023892 | BC023892 | 3.06 | 0.02 | BE687858 |
| 1455805_x_at | coiled-coil domain containing 22 | Ccdc22 | 2.92 | 0.03 | BB165451 |
| 1442402_at | SH3 domain containing ring finger 1 | Sh3rf1 | 2.89 | 0.01 | BB110728 |
| 1434881_s_at | potassium channel tetramerisation domain containing 12 | Kctd12 | 2.87 | 0.01 | BM220945 |
| 1456609_at | calcium/calmodulin-dependent protein kinase II inhibitor 1 | Camk2n1 | 2.84 | 0.00 | BE994488 |
| 1417654_at | syndecan 4 | Sdc4 | 2.74 | 0.03 | BC005679 |
| 1438274_at | IKAROS family zinc finger 4 | Ikzf4 | 2.72 | 0.03 | BG071647 |
| 1418829_a_at | enolase 2, gamma neuronal | Eno2 | 2.49 | 0.04 | NM_013509 |
| 1424316_at | solute carrier family 25 (mitochondrial deoxynucleotide carrier), member | Slc25a19 | 2.41 | 0.00 | BC018167 |
| 1450330_at | interleukin 10 | Il10 | 2.39 | 0.02 | NM_010548 |
| 1439189_at | RIKEN cDNA D630023B12 gene | D630023B12Rik | 2.32 | 0.03 | BB498793 |
| 1432678_at | integrin alpha V | Itgav | 2.30 | 0.00 | AK011583 |
| 1455320_at | — | — | 2.30 | 0.03 | BQ176847 |
| 1446950_at | Thymocyte selection-associated HMG box gene | Tox | 2.22 | 0.02 | BM124834 |
| 1445612_at | — | — | 2.21 | 0.05 | AI114898 |
| 1425145_at | interleukin 1 receptor-like 1 | Il1rl1 | 2.10 | 0.03 | D13695 |

TABLE S1-continued

Affymetrix gene chip analysis between GFP+ and GFP− CD4+ T cells from LILP of Gpr15$^{gfp/+}$ mice.

| Systematic | Gene Title | Gene Symbol | Fold change | Ttest p | Genbank |
|---|---|---|---|---|---|
| 1419339_at | neuraminidase 3 | Neu3 | 2.08 | 0.04 | NM_016720 |
| 1435645_at | monocyte to macrophage differentiation-associated///similar to monocy | Mmd///LOC676546 | 2.08 | 0.05 | AA472735 |
| 1425871_a_at | Single chain antibody ScFv | — | 2.03 | 0.03 | AB007986 |
| 1420692_at | interleukin 2 receptor, alpha chain | Il2ra | 1.99 | 0.04 | AF054581 |
| 1429413_at | carboxypeptidase M | Cpm | 1.98 | 0.03 | AK017670 |
| 1459219_at | Rap guanine nucleotide exchange factor (GEF) 2 | Rapgef2 | 1.97 | 0.03 | BM120546 |
| 1438295_at | Glucocorticoid induced transcript 1 | Glcci1 | 1.91 | 0.05 | BM247146 |
| 1420351_at | tumor necrosis factor receptor superfamily, member 4 | Tnfrsf4 | 1.89 | 0.01 | NM_011659 |
| 1442107_at | filamin, beta | Flnb | 1.89 | 0.00 | BM218614 |
| 1418154_at | cDNA sequence BC004022 | BC004022 | 1.84 | 0.02 | NM_030563 |
| 1457670_s_at | lamin A | Lmna | 1.84 | 0.02 | AV238225 |
| 1444706_at | RIKEN cDNA E430014L09 gene | E430014L09Rik | 1.83 | 0.03 | BB527432 |
| 1416871_at | a disintegrin and metallopeptidase domain 8 | Adam8 | 1.78 | 0.03 | NM_007403 |
| 1435251_at | sorting nexin 13 | Snx13 | 1.77 | 0.03 | AV377013 |
| 1422567_at | niban protein | Niban | 1.75 | 0.03 | NM_022018 |
| 1435981_at | 10 days neonate cerebellum cDNA, RIKEN full-length enriched library, c | — | 1.72 | 0.03 | BM118398 |
| 1428509_at | myosin IE | Myo1e | 1.70 | 0.01 | AK018649 |
| 1420697_at | solute carrier family 15, member 3 | Slc15a3 | 1.63 | 0.00 | NM_023044 |
| 1428074_at | transmembrane protein 158 | Tmem158 | 1.62 | 0.01 | BE981853 |
| 1435787_at | protein phosphatase 1 (formerly 2C)-like | Ppm1l | 1.61 | 0.02 | BB035578 |
| 1448670_at | ubiquitin-conjugating enzyme E2E 3, UBC4/5 homolog (yeast) | Ube2e3 | 1.60 | 0.04 | AW120830 |
| 1441033_at | transmembrane and tetratricopeptide repeat containing 2 | Tmtc2 | 1.60 | 0.01 | BB667269 |
| 1457644_s_at | chemokine (C-X-C motif) ligand 1 | Cxcl1 | 1.58 | 0.02 | BB554288 |
| 1434910_at | RIKEN cDNA A830080D01 gene | A830080D01Rik | 1.57 | 0.00 | BE136476 |
| 1425472_a_at | lamin A | Lmna | 1.56 | 0.05 | BC015302 |
| 1444426_at | RIKEN cDNA F730031O20 gene | F730031O20Rik | 1.56 | 0.05 | BB327547 |
| 1457548_at | A disintegrin-like and metallopeptidase (reprolysin type) with thrombosp | Adamts6 | 1.56 | 0.02 | BB227648 |
| 1419209_at | chemokine (C-X-C motif) ligand 1 | Cxcl1 | 1.55 | 0.02 | NM_008176 |
| 1456956_at | IKAROS family zinc finger 2 | Ikzf2 | 1.55 | 0.00 | BB291816 |
| 1425492_at | bone morphogenetic protein receptor, type 1A | Bmpr1a | 1.54 | 0.00 | BM939768 |
| 1416216_at | RalBP1 associated Eps domain containing protein | Reps1 | 1.52 | 0.05 | NM_009048 |
| 1425493_at | bone morphogenetic protein receptor, type 1A | Bmpr1a | 1.51 | 0.04 | BM939768 |
| 1418500_at | nucleosome assembly protein 1-like 3 | Nap1l3 | 1.46 | 0.04 | NM_138742 |
| 1423626_at | dystonin | Dst | 1.45 | 0.02 | BB150886 |
| 1415961_at | integral membrane protein 2C | Itm2c | 1.43 | 0.02 | NM_022417 |
| 1460469_at | tumor necrosis factor receptor superfamily, member 9 | Tnfrsf9 | 1.42 | 0.04 | BM250782 |
| 1421375_a_at | S100 calcium binding protein A6 (calcyclin) | S100a6 | 1.41 | 0.03 | NM_011313 |
| 1455665_at | LON peptidase N-terminal domain and ring finger 1///similar to CG3236 | Lonrf1///LOC631639 | 1.38 | 0.01 | BB705689 |
| 1454702_at | RIKEN cDNA 4930503L19 gene | 4930503L19Rik | 1.34 | 0.03 | AI450962 |
| 1416418_at | gamma-aminobutyric acid (GABA(A)) receptor-associated protein-like 1 | Gabarapl1 | 1.31 | 0.01 | AF180518 |
| 1418133_at | B-cell leukemia/lymphoma 3 | Bcl3 | 1.31 | 0.03 | NM_033601 |
| 1451584_at | hepatitis A virus cellular receptor 2 | Havcr2 | 1.30 | 0.02 | AF450241 |
| 1429400_at | chloride channel 5 | Clcn5 | 1.30 | 0.01 | BB794830 |
| 1419942_at | Sulfiredoxin 1 homolog (S. cerevisiae) | Srxn1 | 1.28 | 0.00 | AW488194 |
| 1460700_at | signal transducer and activator of transcription 3 | Stat3 | 1.27 | 0.01 | AK004083 |
| 1423488_at | monocyte to macrophage differentiation-associated | Mmd | 1.23 | 0.01 | BC021604 |
| 1440959_s_at | myoneurin | Mynn | 1.19 | 0.00 | BB759556 |
| 1417162_at | transmembrane BAX inhibitor motif containing 1 | Tmbim1 | 1.18 | 0.05 | BC004752 |
| 1435885_s_at | intersectin 1 (SH3 domain protein 1A) | Itsn1 | 1.18 | 0.00 | BM248471 |
| 1447211_at | nuclear receptor interacting protein 1 | Nrip1 | 1.17 | 0.04 | BE956701 |
| 1434302_at | Ras association (RalGDS/AF-6) and pleckstrin homology domains 1 | Raph1 | 1.13 | 0.03 | AV307311 |
| 1437467_at | activated leukocyte cell adhesion molecule | Alcam | 1.12 | 0.05 | AV315205 |
| 1420895_at | transforming growth factor, beta receptor 1 | Tgfbr1 | 1.11 | 0.05 | BM248342 |
| 1426875_s_at | sulfiredoxin 1 homolog (S. cerevisiae) | Srxn1 | 1.06 | 0.00 | BM210600 |
| 1454701_at | RIKEN cDNA 4930503L19 gene | 4930503L19Rik | 1.05 | 0.02 | AI450962 |
| 1434310_at | bone morphogenic protein receptor, type II (serine/threonine kinase) | Bmpr2 | 1.05 | 0.05 | AW546137 |
| 1449835_at | programmed cell death 1 | Pdcd1 | 1.03 | 0.05 | NM_008798 |
| 1437404_at | microtubule associated serine/threonine kinase family member 4 | Mast4 | 1.03 | 0.05 | AI642422 |
| 1444273_at | expressed sequence AW555355 | AW555355 | 1.01 | 0.02 | AW555355 |
| 1426965_at | RAS related protein 2a | Rap2a | 0.99 | 0.02 | BC025198 |
| 1455030_at | protein tyrosine phosphatase, receptor type, J | Ptprj | 0.99 | 0.01 | AI116234 |
| 1444299_at | RIKEN cDNAA430093F15 gene | A430093F15Rik | 0.99 | 0.05 | BB209605 |
| 1431293_a_at | claudin domain containing 1 | Cldnd1 | 0.96 | 0.05 | AK012260 |
| 1416419_s_at | gamma-aminobutyric acid (GABA(A)) receptor-associated protein-like 1 | Gabarapl1 | 0.94 | 0.05 | AF180518 |
| 1446389_at | Nuclear receptor interacting protein 1 | Nrip1 | 0.94 | 0.03 | AW553331 |
| 1456810_at | vacuolar protein sorting 54 (yeast) | Vps54 | 0.93 | 0.04 | BB468447 |
| 1454777_at | solute carrier organic anion transporter family, member 2b1 | Slco2b1 | 0.92 | 0.04 | BB553107 |
| 1435703_at | Transcribed locus | — | 0.91 | 0.03 | AW045947 |
| 1426063_a_at | GTP binding protein (gene overexpressed in skeletal muscle) | Gem | 0.90 | 0.01 | U10551 |
| 1445641_at | ELOVL family member 6, elongation of long chain fatty acids (yeast) | Elovl6 | 0.89 | 0.01 | BB727879 |
| 1438701_at | bicaudal D homolog 1 (Drosophila) | Bicd1 | 0.88 | 0.01 | BB130665 |
| 1453375_at | RIKEN cDNA 4930422N03 gene | 4930422N03Rik | 0.88 | 0.04 | BB071620 |
| 1437399_at | claudin domain containing 1 | Cldnd1 | 0.88 | 0.01 | BE627927 |
| 1456174_x_at | N-myc downstream regulated gene 1 | Ndrg1 | 0.84 | 0.00 | AV309418 |
| 1427892_at | myosin IG | Myo1g | 0.84 | 0.00 | BB235320 |
| 1455009_at | carboxypeptidase D | Cpd | 0.83 | 0.02 | AW550842 |

TABLE S1-continued

Affymetrix gene chip analysis between GFP+ and GFP− CD4+ T cells from LILP of Gpr15gfp/+ mice.

| Systematic | Gene Title | Gene Symbol | Fold change | Ttest p | Genbank |
| --- | --- | --- | --- | --- | --- |
| 1435580_at | RIKEN cDNA C230081A13 gene | C230081A13Rik | 0.83 | 0.02 | AW553275 |
| 1424317_at | solute carrier family 25 (mitochondrial deoxynucleotide carrier), member | Slc25a19 | 0.80 | 0.01 | BC018167 |
| 1425264_s_at | myelin basic protein | Mbp | −0.80 | 0.05 | BB181247 |
| 1450241_a_at | ecotropic viral integration site 2a | Evi2a | −0.81 | 0.04 | NM_010161 |
| 1424241_at | solute carrier family 30 (zinc transporter), member 6 | Slc30a6 | −0.81 | 0.00 | AF233346 |
| 1441347_at | HIV-1 Rev binding protein-like | Hrbl | −0.81 | 0.01 | BB153954 |
| 1437641_at | RIKEN cDNA 4930535B03 gene | 4930535B03Rik | −0.81 | 0.01 | BE981473 |
| 1438981_at | Protein kinase C, beta 1 | Prkcb1 | −0.82 | 0.02 | BB160675 |
| 1436235_x_at | RIKEN cDNA 4732471D19 gene | 4732471D19Rik | −0.83 | 0.04 | BB750674 |
| 1427156_s_at | activating signal cointegrator 1 complex subunit 2 | Ascc2 | −0.83 | 0.05 | BB756983 |
| 1433777_at | l(3)mbt-like 2 (Drosophila) | L3mbtl2 | −0.84 | 0.05 | BB152370 |
| 1422439_a_at | cyclin-dependent kinase 4///similar to Cell division protein kinase 4 (Cy | Cdk4///LOC640611 | −0.85 | 0.01 | NM_009870 |
| 1440326_at | Src family associated phosphoprotein 1 | Skap1 | −0.85 | 0.01 | AV312674 |
| 1423317_at | RIKEN cDNA 3110001D03 gene | 3110001D03Rik | −0.85 | 0.05 | BE915283 |
| 1442494_at | expressed sequence C79242 | C79242 | −0.85 | 0.05 | BG066459 |
| 1443894_at | Neurofibromatosis 1 | Nf1 | −0.86 | 0.04 | BB236216 |
| 1436424_at | RIKEN cDNA 1600020E01 gene | 1600020E01Rik | −0.86 | 0.05 | BG070208 |
| 1430982_at | splicing factor, arginine/serine-rich 1 (ASF/SF2) | Sfrs1 | −0.87 | 0.04 | BF682801 |
| 1428113_at | transmembrane and tetratricopeptide repeat containing 4 | Tmtc4 | −0.88 | 0.01 | BB278364 |
| 1441145_at | RIKEN cDNA D030065N23 gene | D030065N23Rik | −0.88 | 0.01 | BB448266 |
| 1455370_at | RIKEN cDNA A630023P12 gene | A630023P12Rik | −0.89 | 0.05 | AI451630 |
| 1423924_s_at | tetraspanin 14 | Tspan14 | −0.89 | 0.01 | BC025568 |
| 1460002_at | tousled-like kinase 1 | Tlk1 | −0.89 | 0.04 | BM244995 |
| 1424474_a_at | calcium/calmodulin-dependent protein kinase kinase 2, beta | Camkk2 | −0.90 | 0.04 | BI157430 |
| 1418893_at | pre B-cell leukemia transcription factor 2 | Pbx2 | −0.90 | 0.01 | NM_017463 |
| 1415916_a_at | methylenetetrahydrofolate dehydrogenase (NADP+dependent), methen | Mthfd1 | −0.91 | 0.03 | NM_138745 |
| 1426710_at | calmodulin 3 | Calm3 | −0.91 | 0.03 | BB396904 |
| 1420401_a_at | receptor (calcitonin) activity modifying protein 3 | Ramp3 | −0.92 | 0.04 | NM_019511 |
| 1436508_at | RIKEN cDNA 2410014A08 gene | 2410014A08Rik | −0.92 | 0.00 | BB000110 |
| 1438172_x_at | exonuclease domain containing 1 | Exod1 | −0.92 | 0.01 | BB091183 |
| 1435822_at | RIKEN cDNA D830012I24 gene | D830012I24Rik | −0.93 | 0.04 | BB318743 |
| 1428302_at | mitochondrial ribosomal protein L48 | Mrpl48 | −0.94 | 0.05 | BG064141 |
| 1435695_a_at | RIKEN cDNAA030007L17 gene | A030007L17Rik | −0.94 | 0.01 | AA673177 |
| 1442185_at | — | — | −0.94 | 0.05 | AV382148 |
| 1458684_at | synovial sarcoma translocation, Chromosome 18 | Ss18 | −0.95 | 0.01 | BG065620 |
| 1425014_at | nuclear receptor subfamily 2, group C, member 2 | Nr2c2 | −0.95 | 0.02 | AU066920 |
| 1448686_at | interleukin 16 | Il16 | −0.96 | 0.05 | BC026894 |
| 1455353_at | transmembrane and coiled coil domains 1 | Tmcc1 | −0.96 | 0.00 | AV221889 |
| 1451567_a_at | interferon activated gene 203 | Ifi203 | −0.97 | 0.03 | BC008167 |
| 1438391_x_at | hydroxysteroid (17-beta) dehydrogenase 10 | Hsd17b10 | −0.97 | 0.05 | AV078914 |
| 1460555_at | RIKEN cDNA 6330500D04 gene | 6330500D04Rik | −0.98 | 0.03 | BM242294 |
| 1428390_at | WD repeat domain 43 | Wdr43 | −0.98 | 0.05 | AK012043 |
| 1442254_at | Transcribed locus | — | −0.98 | 0.03 | BB366659 |
| 1456432_at | GRB2-related adaptor protein 2 | Grap2 | −0.98 | 0.04 | BB168280 |
| 1417315_at | GRIP1 associated protein 1 | Gripap1 | −0.98 | 0.00 | BG864756 |
| 1419033_at | — | — | −0.99 | 0.01 | AW556821 |
| 1435331_at | expressed sequence AI447904 | AI447904 | −0.99 | 0.01 | BM241008 |
| 1416522_a_at | gene rich cluster, C10 gene | Grcc10 | −1.00 | 0.03 | NM_013535 |
| 1439571_at | RIKEN cDNA E230008J23 gene | E230008J23Rik | −1.00 | 0.00 | BB820889 |
| 1425270_at | kinesin family member 1B | Kif1b | −1.00 | 0.05 | BE199508 |
| 1426342_at | STT3, subunit of the oligosaccharyltransferase complex, homolog B (S. | Stt3b | −1.00 | 0.04 | AK018758 |
| 1426813_at | LTV1 homolog (S. cerevisiae) | Ltv1 | −1.01 | 0.00 | U01139 |
| 1449303_at | sestrin 3 | Sesn3 | −1.01 | 0.01 | NM_030261 |
| 1450966_at | carnitine O-octanoyltransferase | Crot | −1.01 | 0.01 | BB283187 |
| 1416170_at | TNF receptor-associated protein 1 | Trap1 | −1.01 | 0.02 | NM_026508 |
| 1436212_at | transmembrane protein 71 | Tmem71 | −1.03 | 0.02 | AV173260 |
| 1420950_at | zinc and ring finger 1 | Znrf1 | −1.03 | 0.02 | BB026596 |
| 1460419_a_at | protein kinase C, beta 1 | Prkcb1 | −1.04 | 0.02 | X59274 |
| 1428392_at | Ras association (RalGDS/AF-6) domain family 2 | Rassf2 | −1.04 | 0.05 | AK018504 |
| 1427342_at | FAST kinase domains 1 | Fastkd1 | −1.04 | 0.03 | BC023501 |
| 1418968_at | RB1-inducible coiled-coil 1 | Rb1cc1 | −1.04 | 0.02 | BE570980 |
| 1449855_s_at | ubiquitin carboxyl-terminal esterase L3 (ubiquitin thiolesterase)///ubiqui | Uchl3///Uchl4 | −1.05 | 0.02 | AB033370 |
| 1428233_at | cleavage and polyadenylation specific factor 6 | Cpsf6 | −1.05 | 0.04 | BB425379 |
| 1428322_a_at | NADH dehydrogenase (ubiquinone) 1 beta subcomplex, 10 | Ndufb10 | −1.05 | 0.04 | BI905689 |
| 1424181_at | septin 6 | 5-Sep | −1.05 | 0.03 | BC010489 |
| 1452470_at | centrosomal protein 350 | Cep350 | −1.06 | 0.01 | BC019716 |
| 1418495_at | zinc finger CCCH type containing 8 | Zc3h8 | −1.06 | 0.00 | NM_020594 |
| 1431054_at | LSM6 homolog, U6 small nuclear RNA associated (S. cerevisiae) | Lsm6 | −1.07 | 0.05 | AK019126 |
| 1435655_at | small nucleolar RNA, H/ACA box 65 | Snora65 | −1.08 | 0.02 | BG807990 |
| 1420876_a_at | septin 6 | 5-Sep | −1.08 | 0.03 | NM_019942 |
| 1431981_at | hypoxia inducible factor 1, alpha subunit | Hif1a | −1.09 | 0.03 | AK017853 |
| 1421819_a_at | SET translocation///similar to SET protein (Phosphatase 2A inhibitor I2 | Set///LOC671392 | −1.10 | 0.02 | BF134272 |
| 1448864_at | SNF related kinase | Snrk | −1.11 | 0.01 | NM_133741 |
| 1416906_at | anaphase-promoting complex subunit 5 | Anapc5 | −1.11 | 0.03 | NM_021505 |
| 1435329_at | F-box and leucine-rich repeat protein 11 | Fbxl11 | −1.12 | 0.02 | BE690994 |
| 1435925_at | G protein-coupled receptor kinase-interactor 2 | Git2 | −1.13 | 0.01 | BB377392 |

TABLE S1-continued

Affymetrix gene chip analysis between GFP+ and GFP− CD4+ T cells from LILP of Gpr15gfp/+ mice.

| Systematic | Gene Title | Gene Symbol | Fold change | Ttest p | Genbank |
|---|---|---|---|---|---|
| 1423775_s_at | protein regulator of cytokinesis 1 | Prc1 | −1.13 | 0.03 | BC005475 |
| 1458038_at | — | — | −1.14 | 0.01 | BG063073 |
| 1433596_at | DnaJ (Hsp40) homolog, subfamily C, member 6 | Dnajc6 | −1.14 | 0.04 | BQ175337 |
| 1423241_a_at | transcription factor Dp 1///similar to Transcription factor Dp-1 (E2F dime | Tfdp1///LO0664889 | −1.15 | 0.04 | BG075396 |
| 1434301_at | RIKEN cDNA D330050l23 gene | 0330050l23Rik | −1.16 | 0.03 | BE303700 |
| 1430127_a_at | cyclin D2 | Ccnd2 | −1.19 | 0.01 | AK007904 |
| 1454920_at | ubiquitin-like, containing PHD and RING finger domains 2 | Uhrf2 | −1.19 | 0.05 | BQ266387 |
| 1445895_at | T-cell receptor beta, variable 8.2 | Tcrb-V8.2 | −1.20 | 0.05 | AI450773 |
| 1456678_at | Src family associated phosphoprotein 1 | Skap1 | −1.20 | 0.04 | AV314270 |
| 1432850_at | RIKEN cDNA 5430434G16 gene | 5430434G16Rik | −1.21 | 0.02 | AK017390 |
| 1444203_at | Transcribed locus | — | −1.21 | 0.05 | AI661342 |
| 1420381_a_at | ribosomal protein L31 | Rpl31 | −1.21 | 0.01 | NM_053257 |
| 1419119_at | hematopoietic cell signal transducer | Hcst | −1.22 | 0.01 | AF172930 |
| 1443279_at | Nemo like kinase | Nlk | −1.22 | 0.04 | BB204492 |
| 1418181_at | protein tyrosine phosphatase 4a3 | pPtp4a3 | −1.23 | 0.00 | AK014601 |
| 1417384_at | ectonucleoside triphosphate diphosphohydrolase 5 | Entpd5 | −1.23 | 0.03 | NM_007647 |
| 1454899_at | LIM domain containing preferred translocation partner in lipoma | Lpp | −1.26 | 0.02 | BB089138 |
| 1437709_x_at | tetratricopeptide repeat domain 13 | Ttc13 | −1.26 | 0.04 | BB492914 |
| 1433582_at | RIKEN cDNA 1190002N15 gene | 1190002N15Rik | −1.27 | 0.03 | AV309085 |
| 1442332_at | Transforming growth factor, beta receptor III | Tgfbr3 | −1.28 | 0.05 | BG794571 |
| 1420634_a_at | MAD homolog 2 (Drosophila) | Smad2 | −1.28 | 0.01 | NM_010754 |
| 1458031_at | Solute carrier family 25, member 40 | Slc25a40 | −1.28 | 0.05 | BG075632 |
| 1423928_at | phosphoglycerate dehydrogenase like 1 | Phgdhl1 | −1.30 | 0.00 | BC024467 |
| 1441164_at | Phosphatidylinositol-4-phosphate 5-kinase, type II, beta | Pip5k2b | −1.31 | 0.02 | BG071985 |
| 1427135_at | splicing factor, arginine/serine-rich 12 | Sfrs12 | −1.31 | 0.01 | AV012790 |
| 1454654_at | disrupted in renal carcinoma 2 (human) | Dirc2 | −1.32 | 0.04 | BG069395 |
| 1423608_at | integral membrane protein 2A | Itm2a | −1.33 | 0.04 | BI966443 |
| 1434544_at | bolA-like 2 (E. coli) | Bola2 | −1.33 | 0.01 | BE992311 |
| 1426002_a_at | cell division cycle 7 (S. cerevisiae) | Cdc7 | −1.38 | 0.01 | AB018574 |
| 1434105_at | EPM2A (laforin) interacting protein 1 | Epm2aip1 | −1.38 | 0.04 | AV340515 |
| 1418641_at | lymphocyte cytosolic protein 2 | Lcp2 | −1.39 | 0.02 | BC006948 |
| 1434532_at | cDNA sequence BC035295 | BC035295 | −1.40 | 0.00 | BB796273 |
| 1456655_at | Exostoses (multiple) 1 | Ext1 | −1.40 | 0.05 | BM231698 |
| 1439449_at | special AT-rich sequence binding protein 1 | Satb1 | −1.41 | 0.01 | BB724383 |
| 1418826_at | membrane-spanning 4-domains, subfamily A, member 6B | Ms4a6b | −1.42 | 0.01 | NM_027209 |
| 1448274_at | complement component 1, q subcomponent binding protein | C1qbp | −1.42 | 0.01 | NM_007573 |
| 1423478_at | protein kinase C, beta 1 | Prkcb1 | −1.42 | 0.05 | BF660388 |
| 1452676_a_at | polyribonucleotide nucleotidyltransferase 1 | Pnpt1 | −1.43 | 0.03 | BB777815 |
| 1455711_at | deltex 4 homolog (Drosophila) | Dtx4 | −1.44 | 0.04 | AW122183 |
| 1443263_at | BTB and CNC homology 2 | Bach2 | −1.46 | 0.02 | AV365508 |
| 1458406_at | Expressed sequence AI429294 | AI429294 | −1.47 | 0.00 | BG144063 |
| 1456433_at | regulator of chromosome condensation (RCC1) and BTB (POZ) domain | Rcbtb1 | −1.47 | 0.01 | BB000798 |
| 1450095_a_at | acylphosphatase 1, erythrocyte (common) type | Acyp1 | −1.48 | 0.04 | NM_025421 |
| 1438476_a_at | chromodomain helicase DNA binding protein 4 | Chd4 | −1.49 | 0.04 | BB201828 |
| 1427184_at | T-cell receptor beta, variable 13 | Tcrb-V13 | −1.51 | 0.05 | BF318536 |
| 1417136_s_at | serine/arginine-rich protein specific kinase 2 | Srpk2 | −1.51 | 0.03 | NM_009274 |
| 1417509_at | ring finger protein (C3HC4 type) 19 | Rnf19 | −1.52 | 0.01 | AF120206 |
| 1452151_at | cDNA sequence BC021523 | BC021523 | −1.55 | 0.04 | BC021523 |
| 1454745_at | Rho GTPase activating protein 29 | Arhgap29 | −1.58 | 0.04 | BG074320 |
| 1417164_at | dual specificity phosphatase 10 | Dusp10 | −1.58 | 0.03 | NM_022019 |
| 1423756_s_at | insulin-like growth factor binding protein 4 | Igfbp4 | −1.64 | 0.02 | BC019836 |
| 1455132_at | RIKEN cDNA A430107D22 gene | A430107D22Rik | −1.64 | 0.03 | AV312663 |
| 1421305_x_at | rabaptin, RAB GTPase binding effector protein 1 | Rabep1 | −1.65 | 0.01 | NM_019400 |
| 1416697_at | dipeptidylpeptidase 4 | Dpp4 | −1.66 | 0.01 | NM_010074 |
| 1434036_at | metastasis suppressor 1 | Mtss1 | −1.68 | 0.04 | AV024771 |
| 1424464_s_at | RIKEN cDNA 2210010L05 gene | 2210010L05Rik | −1.68 | 0.04 | BF225441 |
| 1447092_at | Platelet/endothelial cell adhesion molecule 1 | Pecam1 | −1.69 | 0.03 | BG063222 |
| 1419163_s_at | DnaJ (Hsp40) homolog, subfamily C, member 3 | Dnajc3 | −1.70 | 0.04 | BE624323 |
| 1424826_s_at | metastasis suppressor 1 | Mtss1 | −1.71 | 0.02 | BC024131 |
| 1417236_at | EH-domain containing 3 | Ehd3 | −1.74 | 0.03 | BM234719 |
| 1426505_at | ecotropic viral integration site 2b | Evi2b | −1.74 | 0.01 | AI122415 |
| 1426850_a_at | mitogen activated protein kinase kinase 6 | Map2k6 | −1.75 | 0.05 | BB261602 |
| 1441705_at | expressed sequence AU015680 | AU015680 | −1.76 | 0.00 | BG145559 |
| 1426892_at | utrophin | Utrn | −1.76 | 0.04 | AI788797 |
| 1418222_at | RIKEN cDNA 2610024G14 gene | 2610024G14Rik | −1.76 | 0.01 | NM_019836 |
| 1456121_at | leucine-rich repeats and IQ motif containing 2 | Lrriq2 | −1.76 | 0.05 | BM224149 |
| 1456358_at | Ets variant gene 3 | Etv3 | −1.79 | 0.05 | BM932547 |
| 1430191_at | RIKEN cDNA 9130004J05 gene | 9130004J05Rik | −1.80 | 0.02 | BB748887 |
| 1426343_at | STT3, subunit of the oligosaccharyltransferase complex, homolog B (S. | Stt3b | −1.81 | 0.00 | AK018758 |
| 1454578_at | RIKEN cDNA 6030458A19 gene | 6030458A19Rik | −1.84 | 0.01 | AK020073 |
| 1443090_at | Choline/ethanolaminephosphotransferase 1 | Cept1 | −1.86 | 0.01 | BB361936 |
| 1441068_at | RIKEN cDNAA130001G05 gene | A130001G05Rik | −1.86 | 0.01 | BB631473 |
| 1449619_s_at | Rho GTPase activating protein 9 | Arhgap9 | −1.91 | 0.03 | AU043488 |
| 1424505_at | required for meiotic nuclear division 1 homolog (S. cerevisiae) | Rmnd1 | −1.93 | 0.01 | BC027299 |
| 1428800_a_at | pseudouridylate synthase 7 homolog (S. cerevisiae)-like | Pus7l | −1.93 | 0.02 | AK019372 |
| 1453571_at | DEP domain containing 6 | Depdc6 | −1.96 | 0.04 | BB324973 |

TABLE S1-continued

Affymetrix gene chip analysis between GFP$^+$ and GFP$^-$ CD4$^+$ T cells from LILP of Gpr15$^{gfp/+}$ mice.

| Systematic | Gene Title | Gene Symbol | Fold change | Ttest p | Genbank |
|---|---|---|---|---|---|
| 1436097_x_at | Rho GTPase activating protein 9 | Arhgap9 | −2.10 | 0.04 | BB327418 |
| 1417663_a_at | N-myc downstream regulated gene 3 | Ndrg3 | −2.13 | 0.00 | BE631549 |
| 1448208_at | MAD homolog 1 (Drosophila) | Smad1 | −2.18 | 0.01 | NM_008539 |
| 1445028_at | Protein kinase C, alpha | Prkca | −2.20 | 0.04 | BE993069 |
| 1419361_at | synovial sarcoma translocation, Chromosome 18 | Ss18 | −2.21 | 0.04 | AI528781 |
| 1417235_at | EH-domain containing 3 | Ehd3 | −2.23 | 0.05 | BM234719 |
| 1437584_at | Cyclin D3 | Ccnd3 | −2.31 | 0.00 | BE685667 |
| 1450639_at | solute carrier family 28 (sodium-coupled nucleoside transporter), membe | Slc28a2///LOC38141 | −2.37 | 0.01 | NM_021520 |
| 1423313_at | phosphodiesterase 7A | Pde7a | −2.39 | 0.02 | BG070255 |
| 1457687_at | B-cell leukemia/lymphoma 2 | Bcl2 | −2.42 | 0.00 | BI664467 |
| 1438125_at | RIKEN cDNA C230085N15 gene | C230085N15Rik | −2.43 | 0.03 | BB393897 |
| 1433944_at | HECT domain containing 2 | Hectd2 | −2.45 | 0.05 | AV256030 |
| 1426044_a_at | protein kinase C, theta | Prkcq | −2.55 | 0.03 | AB062122 |
| 1416318_at | serine (or cysteine) peptidase inhibitor, clade B, member 1a | Serpinb1a | −2.70 | 0.00 | AF426024 |
| 1433169_at | RIKEN cDNA 5830456J23 gene | 5830456J23Rik | −2.70 | 0.03 | AK018017 |
| 1427683_at | early growth response 2 | Egr2 | −2.84 | 0.02 | X06746 |
| 1427417_at | sex comb on midleg-like 4 (Drosophila) | Scml4 | −2.84 | 0.04 | BB212066 |
| 1425628_a_at | similar to General transcription factor II-I (GTFII-I) (TFII-I) (Bruton tyrosin | LOC669007 | −2.86 | 0.02 | AF043220 |
| 1430129_a_at | COMM domain containing 8 | Commd8 | −3.28 | 0.05 | AK017777 |
| 1440842_at | RIKEN cDNA C230085N15 gene | C230085N15Rik | −3.31 | 0.04 | AI449439 |
| 1433795_at | transforming growth factor, beta receptor III | Tgfbr3 | −3.33 | 0.01 | BM122301 |
| 1430622_at | RIKEN cDNA 4833423F13 gene | 4833423F13Rik | −3.35 | 0.02 | AW764291 |
| 1437699_at | RIKEN cDNA E430014B02 gene | E430014B02Rik | −3.65 | 0.03 | BB031353 |
| 1458218_s_at | phosphodiesterase 7A | Pde7a | −3.70 | 0.00 | AU015378 |
| 1452416_at | interleukin 6 receptor, alpha | Il6ra | −3.83 | 0.03 | X53802 |
| 1449235_at | Fas ligand (TNF superfamily, member 6) | Fasl | −3.83 | 0.02 | NM_010177 |
| 1427819_at | — | — | −5.55 | 0.03 | BC027249 |
| 1443579_s_at | DEP domain containing 6 | Depdc6 | −5.76 | 0.03 | AI957118 |
| 1452792_at | DAZ interacting protein 1 | Dzip1 | −6.14 | 0.01 | AI509011 |
| 1430448_at | RIKEN cDNA 6720418B01 gene | 6720418B01Rik | −6.62 | 0.01 | BB392953 |
| 1433939_at | hypothetical protein A730046J16 | A730046J16 | −6.96 | 0.02 | BQ177036 |
| 1441172_at | AF4/FMR2 family, member 3 | Aff3 | −7.40 | 0.01 | BM239026 |
| 1433977_at | heparan sulfate (glucosamine) 3-O-sulfotransferase 3B1 | Hs3st3b1 | −12.09 | 0.01 | BG918344 |
| 1451363_a_at | DENN/MADD domain containing 2D | Dennd2d | −13.02 | 0.03 | BC008266 |

Unless defined otherwise, all technical and scientific terms used herein have the same meaning as commonly understood by one of ordinary skill in the art to which this invention belongs.

It is to be understood that this invention is not limited to particular assay methods, or test agents and experimental conditions described, as such methods and agents may vary. It is also to be understood that the terminology used herein is for the purpose of describing particular embodiments only, and is not intended to be limiting, since the scope of the present invention will be limited only the appended claims.

Example I

Materials and Methods

Animals

Gpr15$^{gfp/gfp}$ mice were generated by transfer of embryonic stem cells (E14 cells, 129SvEv) that were manipulated by homologous recombination. All the mice were kept in a specific pathogen free (SPF) facility. Gpr15$^{gfp/gfp}$ mice used for the experiments were backcrossed to C57BL/6 at least 9 times unless specified. All comparisons were done between littermates or pups of littermates and mice were co-housed after weaning before the experiments. Mice used for Citrobacter infection were SFB (Segmented Filamentous Bacteria)-free. R. A. Flavell kindly provided us with Foxp3$^{ires-mrfp}$ mice (35). Bone marrow of Foxp3$^{sf}$, Ptprc$^a$ (Scurfy, Ly5.1) mice (36) was kindly provided by A. Y. Rudensky. All animal studies were performed according to the protocol approved by the Institutional Animal Care and Usage Committee (IACUC) of New York University.

Cell Preparation from Intestines

A modified version of a previously described protocol was used (37). For the large intestine, cecum and colon were dissected from mice. We used Intramedic Polyethylene tubes (Becton Dickinson) to turn the tissues inside out exposing the epithelial layer during the process. Tissues were washed with ice-cold PBS once and treated sequentially with 1 mM DTT/PBS for 10 min and with 30 mM EDTA/PBS for 10 min twice while shaking. After these treatments, samples were washed once with PBS and the polyethylene tube was removed. Cecal or colonic patches were cut out and the rest of the tissues were digested with collagenase 8 (Sigma), Dispase (Worthington), and DNase I in RPMI-10 (RPMI media supplemented with 10% Fetal Bovine Serum (FBS), Penicillin/Streptomycin, 2 mM L-glutamine, 1 mM Sodium Pyruvate, 10 mM Hepes, 100 µM non-essential amino acids, and 55 µM β-mercaptaethanol) for 1.5-2 h at 37° C. until digestion was complete. Digested tissues were filtered through a 100 µm filter and cells were recovered at the interface between 40% and 80% percoll (GE healthcare) after spinning for 20 min at 850 g. Later, samples were filtered twice with 40 µm Nylon mesh (Fisher Scientific) and either stained for cellular markers or stimulated before intracellular staining. Cell numbers were counted by Vi-Cell XR (Beckman Coulter) or by AccuCount Fluorescent particles (Spherotech, Inc) during flow cytometry analysis.

For the small intestine preparation, the whole small intestine was isolated from mice and Peyer's patches were removed. The rest of the tissues were cut longitudinally and eventually cut into 8 pieces. Subsequently, samples were washed with ice-cold PBS once and treated with 5 mM EDTA/PBS for 10 min while shaking. Then, they were washed in PBS twice. Tissues were digested in Collagenase D (Roche), Dispase (Worthington), and DNase I in RPMI-10 for 1.5-2 h at 37° C. Digested tissues were processed as described above.

Gene Chip Analysis

RNA was prepared from sorted GFP$^+$CD4$^+$ T cells and GFP$^-$CD4$^+$ T cells in LILP of Gpr15$^{gfp/+}$ mice. For microarray analysis, GeneChip Mouse Genome 430 2.0 arrays (Affymetrix) were used according to the manufacturer's protocols by staff at the Genome Technology Center (GTC) in the NYU Medical Center. Data were analyzed with GeneSpring GX11.5 software. Genes with p-values no more than 0.05 and with more than 1.6-fold change were selected. Fold change shown in the table was based on expression in GFP$^+$CD4$^+$T cells compared to that in GFP$^-$CD4$^+$T cells.

Intracellular Cytokine Staining and FOXP3 Staining of Lymphocytes from the Gut

For intracellular cytokine staining, single cell suspensions prepared from the small or large intestines were stimulated in the presence of Monensin (BD GolgiStop) with PMA (50 ng/ml, Sigma) and Ionomycin (500 ng/ml, Sigma) in RPMI-10 for 4 h. Subsequently, cells were stained for cellular markers and additionally stained by fixable dye for dead cells (Invitrogen). Cells were fixed and permeabilized with BD Cytofix/Cytoperm plus (BD Biosciences) according to the manufacturer's protocol.

For FOXP3 and HELIOS staining, single cell suspensions prepared from intestines were stained for cellular markers and later fixed and permeabilized using the FOXP3/Transcription factor buffer set (eBiosciences) according to the manufacturer's protocol.

Short-Term Competitive Homing Assay

The coding region of mouse GPR15 was cloned into the MSCV-IRES-Thy1.1 retroviral construct (38). Retroviruses were generated by transient transfection of Phoenix cells. CD4$^+$ CD62L$^{high}$CD44$^{low}$CD25$^-$ T$_{naive}$ cells were sorted by FACS Aria IIu (BD Biosciences) and stimulated with 0.25 µg/ml αCD3ε (145-2c11, ATCC) and 1 µg/ml of αCD28 (37.51, eBiosciences) antibodies cross-linked by plate-bound α-hamster IgG (MP Biochemical) in RPMI-10. At day 1 and day 2 after stimulation, cells were transduced with retrovirus (spinning at 850 g for 2 h with 4 µg/ml of polybrene). CD4$^+$ T$_{naive}$ cells from B6. SJL-Ptprc$^a$Pep3$^b$/BoyJ (The Jackson Laboratory) were used for transduction of Gpr15 and CD4$^+$ T$_{naive}$ cells from C57BL/6 were used for transduction of empty vector. At day 3, cells were washed and plated again only with 100 U/ml of IL-2. At day 5, live cells were harvested by lymphocyte-M (Cedarlane). The congenic cells were mixed at a 1:1 ratio and 20-30 million mixed cells in total were transferred intravenously into the recipient mice (C57BL/6). Migration of donor cells into each organ was determined at 10 h after transfer (unless specified) by flow cytometry analysis. All donor cells expressed THY1.1 and GPR15-expressing cells and control cells expressed CD45.1 and CD45.2, respectively.

For blocking integrin function, 100 µg of Rat IgG2a,k isotype control antibody (Biolegend), anti-integrin β7 antibody (Biolegend, FIB504), anti-integrin α4 antibody (Millipore, PS/2), or 100 µg each of FIB504 and PS/2 were injected into recipient mice 12 hrs before transfer.

For examining the activity of GPR15 ligand, competitive homing assays were performed with Germ-free mice or antibiotics-treated (with mixture of ampillicin, vancomycin, metronidazole, and neomycin for 2 weeks) mice as recipients.

For Het and KO competitive homing assays, CD4$^+$ T$_{naive}$ cells (CD62L$^{hi}$CD44$^{lo}$CD25$^-$ mRFP$^-$ GFP$^-$) were sorted from Gpr15$^{gfp/+}$ Foxp3$^{ires-mrfp}$ or Gpr15$^{gfp/gfp}$ Foxp3$^{ires-mrfp}$ mice which have different congenic markers. Sorted cells were stimulated with 0.25 µg/ml αCD3ε (145-2c11, ATCC) and 1 µg/ml of αCD28 antibodies (37.51, eBiosciences) cross-linked by plate-bound α-hamster IgG in the presence of human IL-2 (100 U/ml), IL-21 (25 ng/ml, R&D systems), human TGF-β1 (5 ng/ml, Peprotech), and retinoic acid (100 pM) for 3 days. At day 3, cells were washed and plated again only with human IL-2 (100 U/ml), IL-21 (25 ng/ml), human TGF-β1 (5 ng/ml), and retinoic acid (100 pM). At day 5, the congenic cells were mixed at a 1:1 ratio and ~80 million mixed cells in total were transferred intravenously to the congenic recipient mice.

Antibiotics Treatment

For antibiotics treatment, a mixture of ampillicin (1 g/L), vancomycin (0.5 g/L), metronidazole (1 g/L), and neomycin (1 g/L) was provided in the drinking water to breeding pairs, and newborn pups were continuously supplied with this mixture after weaning until the analysis.

OVA feeding 1.5% of chicken ovalbumin (Sigma) was added to drinking water for OT-II transgenic, Rag2$^{-/-}$ mice with Gpr15$^{gfp/+}$ or Gpr15$^{gfp/gfp}$ genotypes. OVA-containing drinking water was replaced every other day. 10 days later, cells from different organs were prepared and examined for GFP expression and cell numbers.

In Vitro Stimulation of T Cells to Examine GFP Induction

All T cell cultures were done in RPMI-10. CD4$^+$ T$_{naive}$ (CD62L$^{hi}$CD44$^{lo}$CD25$^-$mRFP$^-$ GFP$^-$), Tregs with naive phenotype (CD62L$^{hi}$CD44$^{lo}$CD25$^+$mRFP$^+$ GFP$^-$), T$_{memory}$ (CD62L$^{lo}$CD44$^{hi}$CD25$^-$mRFP$^-$ GFP$^-$), and Tregs with memory phenotype (CD62L$^{lo}$CD44$^{hi}$CD25$^+$mRFP$^+$ GFP$^-$) were sorted from Gpr15$^{gfp/+}$ Foxp3$^{ires-mrfp}$ mice. Sorted cells were stimulated with 0.25 µg/ml αCD3ε (145-2c11, ATCC) and 1 µg/ml of αCD28 antibodies (37.51, eBiosciences) cross-linked by plate-bound α-hamster IgG in the presence of human IL-2 (100 U/ml) alone, or additionally with IL-21 (10 ng/ml, R&D systems) or IL-6 (20 ng/ml, Peprotech), or IL-27 (20 ng/ml, eBioscience) in the presence of varying concentrations of human TGF-β1 (αTGFβ blocking antibody [R&D systems], or 0, 0.5 ng/ml, or 5 ng/ml TGF-β1 [Peprotech]) for 3 days. The same conditions were used for retinoic acid (Sigma-Aldrich) treatment with IL-2 only.

In Vitro Treg-Mediated Suppression Assay

We used a slightly modified condition from that described previously (39). Tregs (CD4$^+$CD25$^+$mRFP$^+$) were sorted from Gpr15$^{+/+}$ Foxp3$^{ires-mrfp}$ or Gpr15$^{gfp/gfp}$ Foxp3$^{ires-mrfp}$ mice. CD4$^+$ T$_{naive}$ cells (CD4$^+$CD62L$^{hi}$CD44$^{lo}$CD25$^-$) were sorted from B6. SJL-Ptprc$^a$Pep3$^b$/BoyJ mice (The Jackson Laboratory) and labeled with 1.25 µM of CFSE (Invitrogen) for 15 min at 37° C., by making 2.5 µM of CFSE in RPMI/1% FBS and adding the same volume of cells in RPMI/1% FBS during vortexing. Labeling was stopped by adding 5 volumes of ice-cold FBS. In addition, splenocytes obtained from C57BL/6 mice were treated with 50 µg/ml of Mitomycin C (Sigma) for 40 min at 37° C. 8×10$^4$ splenocytes (Mitomycin C-treated) were mixed with 3×10$^4$ T$_{naive}$, varying numbers of Tregs, and 1 µg/ml of αCD3ε (145-2c11) in RPMI-10 in each well of 96 well round bottom plates. At day 3, proliferation of CD45.1$^+$ T$_{naive}$ was examined by flow cytometry analysis.

Mixed Bone-Marrow Chimera Generation

Male Gpr15$^{gfp/gfp}$ mice were irradiated twice with 600 rad and i.v. transferred with a 1:1 mixture of Thy1-depleted bone marrow cells from Gpr15$^{+/+}$ and Foxp3$^{sf}$ mice or from Gpr15$^{gfp/gfp}$ and Foxp3$^{sf}$ mice (2×10$^6$ cells total). Chimeric mice were infected with *Citrobacter rodentium* 7 weeks later.

Citrobacter-Induced Colitis

*Citrobacter rodentium* strain DBS100 (ATCC 51459; American Type Culture Collection) was recovered by inoculation in 5 ml LB broth and shaking at 37° C. overnight. The next day, the bacteria was inoculated in fresh medium (500 ml) and grown until the culture reached the exponential phase ($OD_{600}$=0.4-0.6). Mice were infected by oral gavage with $8\times10^9$ of *C. rodentium* in a total volume of 400 µl per mouse ($O.D._{600}$=2.5×10$^8$ bacteria). The concentration of bacteria was confirmed by plating serially diluted cultures on MacConkey agar plates. Colonic tissues were analyzed at day 9 or day 10 after the infection by H&E staining, RT-PCR, and colony forming assay. Paraffin embedding and H&E staining were performed by staff of the Histopathology core at the NYU Medical Center.

αCD40 Antibody-Induced Inflammation/Colitis and Rescue by Treg Transfer

Injection of agonist αCD40 (FGK 45) antibody induces acute systemic and local inflammatory diseases, including wasting, splenomegaly, hepatopathology, and colitis in Rag 1 or 2 deficient mice which do not have adaptive immunity (30). To evaluate the inflammatory reactions upon αCD40 antibody injection in mice with adaptive immunity, $Gpr15^{gfp/+}$ and $Gpr15^{gfp/gfp}$ mice were administered 200-300 µg of αCD40 antibody intra-peritoneally and inflammatory cytokine expression was examined by RT-PCR in different tissues at day 3. For induction of acute colitis, $Rag2^{-/-}$ mice were injected with αCD40 antibody (200 µg i.p.). 7 days later when the pathology reaches its peak, colonic tissues were examined. It has been shown that transfer of Tregs can rescue colitis induced in $Rag2^{-/-}$ mice (31, 32). For the rescue, $Rag2^{-/-}$ mice were transferred intravenously with $5\times10^5$ $CD4^+CD25^+mRFP^+$ Tregs either from $Gpr15^{+/+}$ $Foxp3^{ires-mrfp}$ mice or $Gpr15^{gfp/gfp}$ $Foxp3^{ires-mrfp}$ mice. 3 weeks later, mice were injected with αCD40 antibody (200 µg i.p.) and colonic tissues were examined at day 7 after antibody injection. Tissues were processed for H&E staining as described above.

Colitis induction by $T_{naive}$ transfer $Rag2^{-/-}$ mice were infected by *Helicobacter hepaticus* as previously described (31) and transferred intravenously with $3\times10^5$ $CD4^+$ $T_{naive}$ cells either from $Gpr15^{+/+}$ $Foxp3^{ires-mrfp}$ mice or $Gpr15^{gfp/gfp}$ $Foxp3^{ires-mrfp}$ mice. Colonic tissues were examined at six weeks after the transfer. Tissues were processed for H&E staining as described above.

Histology Scoring of H&E Stained Slides

The H&E slides from each sample were examined double-blindly by a team of a gastrointestinal pathologist and an investigator. The histology scoring is based upon evaluation of 8 different criteria. For each case, 3 foci of the most severely affected microscopic fields were chosen for analysis and the score for each criterion was an average from three foci. The final score is a combination of those from each criterion. Scoring was performed under high power view (40×) as follows: Neutrophil infiltration (0: None, 1: 1-50 cells, 2: 50-100 cells, 3: 100+ cells); Edema (0: None, 1: Mild, 2: Moderate, 3: Severe); Goblet cell depletion (0: 50+/HPF, 1: 25-50/HPF, 2: 10-25/HPF, 3: <10/HPF); Crypt damage (0: Intact, 1: Basal 1/3, 2: Basal 2/3, 3: Entire loss); Atrophy & Crypt loss (0: Normal crypt, 1: Mild, 2: Moderate, 3: Severe); Epithelial regeneration (0: Complete, 1: Slight injury, 2: Surface not intact, 3: No tissue repair); Epithelial hyperplasia (0: None, 1: 1-50%, 2: 51-100%, 3: >100%); Erosion & Ulceration (0: None, 1: Focal, lamina propria, 2: Muscularispropria, 3: Full thickness). Acute inflammation index was a combined score of neutrophil infiltration and Edema.

Reverse Transcription and Real-Time PCR

Cells were resuspended in Trizol (Invitrogen) and processed according to the manufacturer's protocol to prepare RNA. Subsequently, RNA samples were treated with RNase-free DNase (Roche) and reverse-transcribed by Superscript III (Invitrogen) or by First-Strand cDNA Synthesis Kit (Affymetrix) with poly-T primer. For detection of mRNA, we used Taqman Gene Expression Assays (Applied Biosystems), platinum Taq polymerase (Invitrogen), and LightCycler 48011 (Roche). Relative expression level was normalized to Beta-actin. Assay IDs for Taqman probe/primer set are as follows. Gpr15: Mm01346276_g1; Beta-actin: Mm02619580_g1; Tnfalpha: Mm00443258_m1; Il-1beta: Mm01336189_m1; Cxcl2: Mm00436450_m1; BETA-ACTIN: Hs99999903_m1; GPR15: Hs00922903_s1.

Human Samples

Blood lymphocytes were prepared from IRB-approved buffy coats from the New York Blood Center. Buffy coat was first spun with Ficoll for 30 min at 850 g. Subsequently, $CD4^+$ cells were enriched with AutoMACS purification (Miltenyi Biotec) and later sorted. Anonymized, grossly normal samples of colon or ileum were obtained from colon cancer resection specimens. Samples of normal duodenum were obtained following the Whipple procedure for pancreatic cancer resection. All human gut tissues were acquired by the NYULMC Biorepository Core. Muscularis and fat layer were removed first and washed with ice-cold PBS once. Later, samples were treated sequentially with 1 mM DTT/PBS for 10 min and with 30 mM EDTA/PBS for 10 min twice. After these treatments, samples were washed once with PBS and extra fat tissue was removed again. The lamina propria layer was digested with collagenase 8 (Sigma) and Dnase I in RPMI-10 for 1.5-2 hrs at 37° C. until digestion was complete. Digested tissues were filtered through a 100 µm filter and cells were recovered at the interface between 40% and 80% percoll (GE healthcare) after spinning for 20 min at 850 g. $CD127^{lo}CD25^{hi}$ cells and $CD127^{hi}CD25^{lo}$ cells were sorted for enrichment of Tregs and non-Tregs, respectively, and their enrichment was confirmed by RT-PCR (FOXP3: Hs03987537_m1, Applied Biosystems).

Results

Figure 5A:
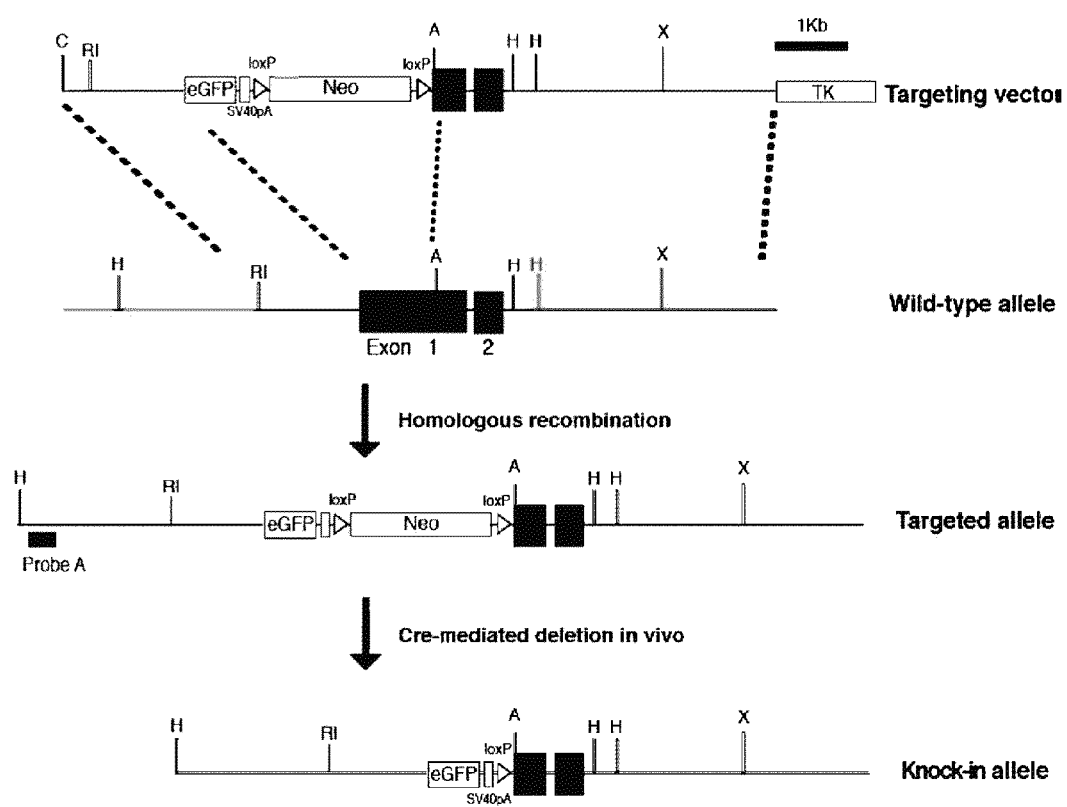
FIG. 5A-5C. Generation of Gpr15 GFP knock-in mice. (5A) Homologous recombination strategy for generating the mutant allele. Deletion of the Neo gene was achieved by Cre-mediated germline deletion in vivo (A: ApaI; C: ClaI; RI: EcoRI; H: HindIII; X: XbaI). (5B) Southern blot of wild-type and targeted allele to confirm homologous recombination (Probe A with HindIII digestion) (5C) Taqman RT-PCR of Gpr15 mRNA in TCRβ$^+$ cells, normalized to Beta-actin.
Figure 5B:
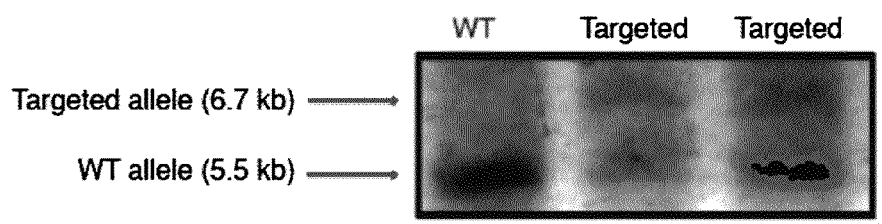
Figure 5C:
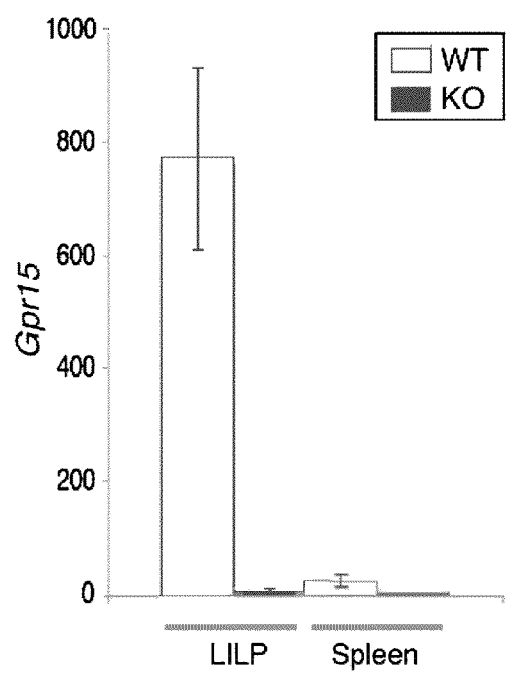
Figure 6A:
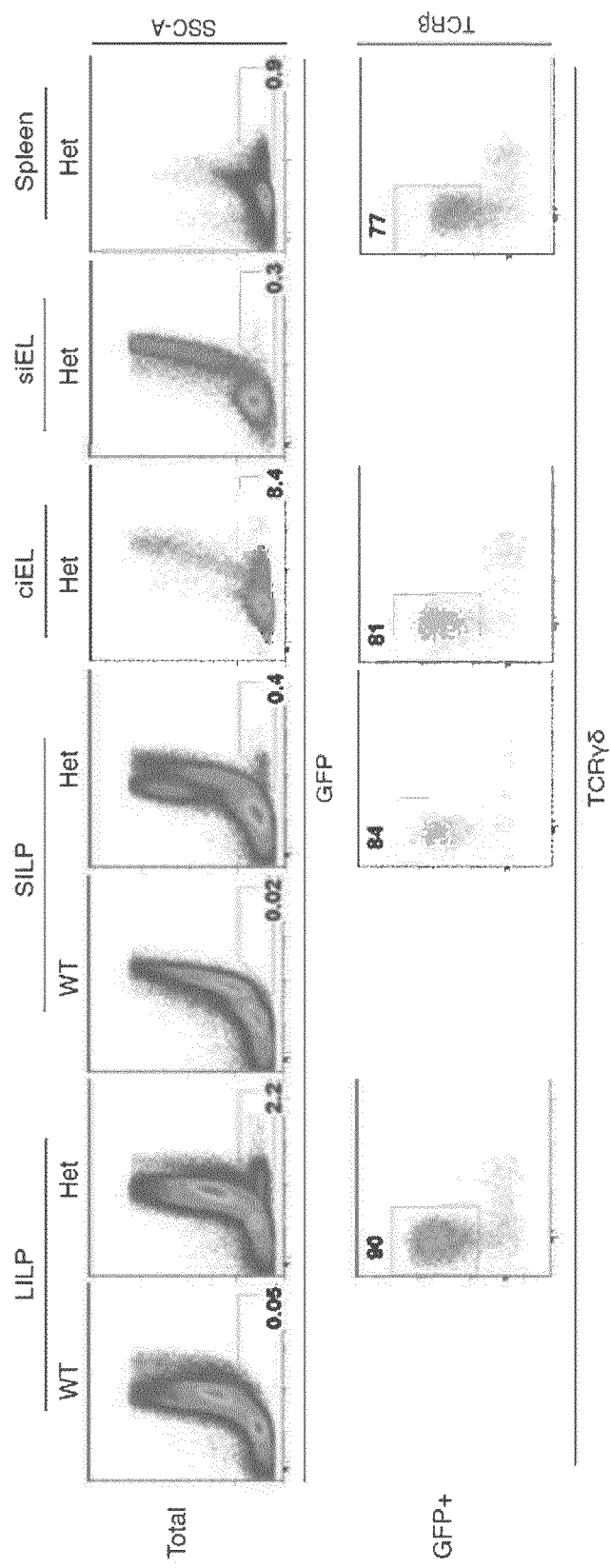
Figure 6C:
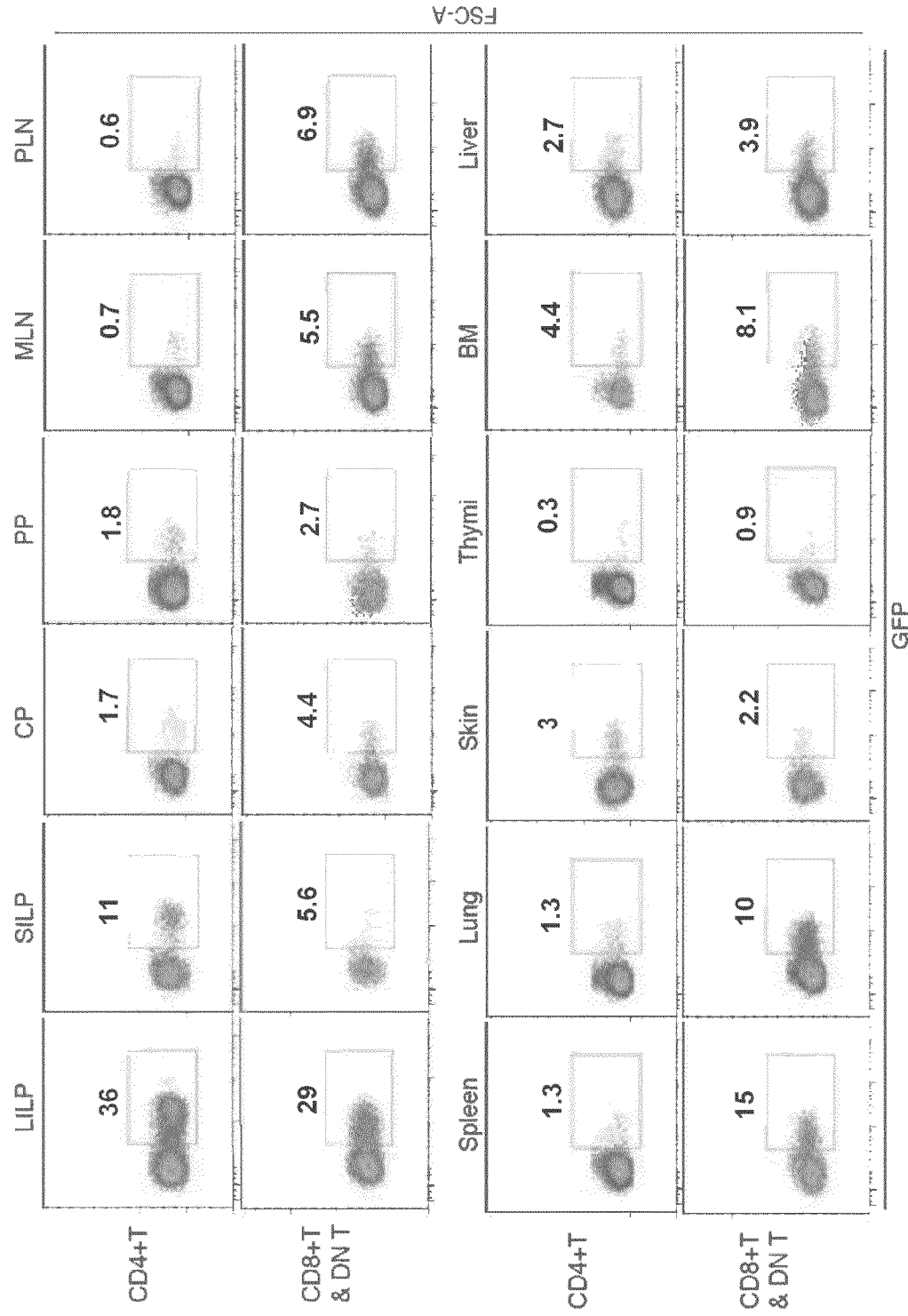
Figure 6D:
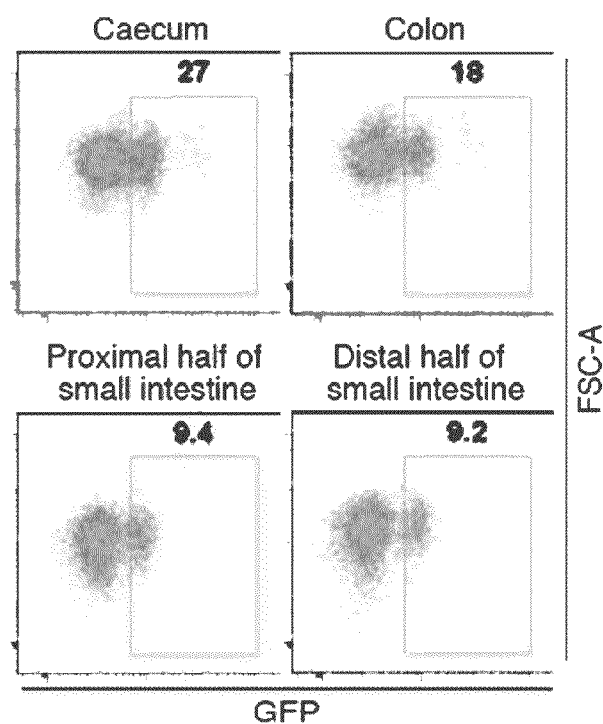
Figure 6E:
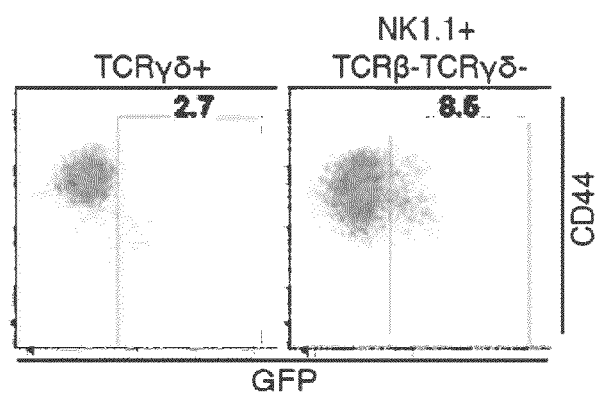
Figure 6F:
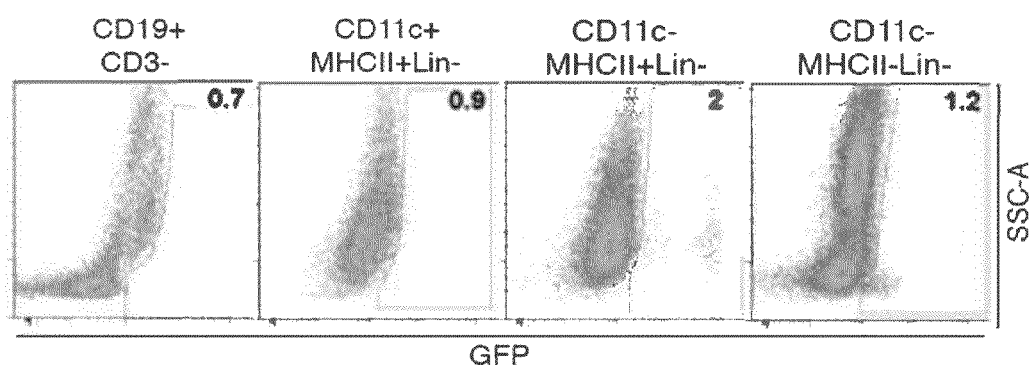
Figure 6G:
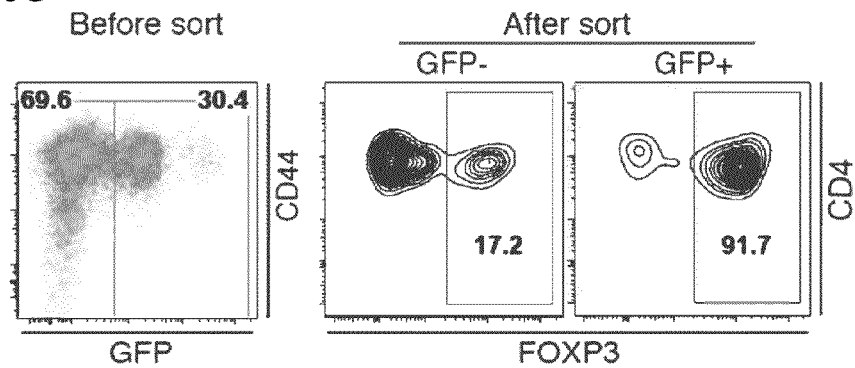
Figure 6H:
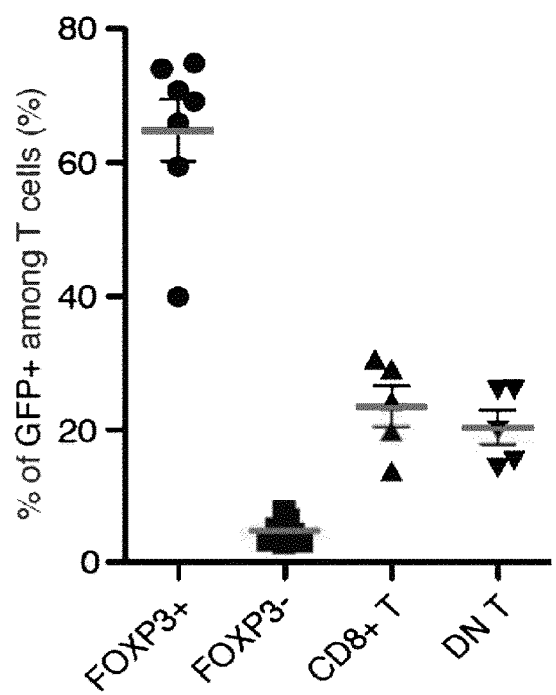

Human GPR15 (also known as BOB) was originally cloned as a co-receptor for HIV/SIV (21, 22). To study the physiological function of its murine ortholog, we made knock-in mice in which endogenous Gpr15 was replaced with the coding sequence for GFP (FIG. 5). With this strategy, GPR15 expression could be tracked in GPR15-sufficient heterozygous (Het) mice and its function could be examined using loss-of-function homozygous (KO) mice. In humans, GPR15 mRNA is highly expressed in the colon, peripheral blood lymphocytes (PBL), and spleen (21). Similarly, in mice, GFP expression was detected in gut tissues and lymphoid organs, where it was largely restricted to TCRβ+ cells (FIG. 6A, 6B). Further analysis revealed that T cells in the large intestine lamina propria (LILP) exhibited the highest percentage of GFP+ cells (FIG. 6C, 6D). GPR15 expression was minimal in most other immune cells in the LILP, including TCRγδ+ T cells, B cells, NK cells, and DCs (FIG. 6E, 6F). To determine the functional characteristics of GPR15+ cells, we analyzed the transcriptomes of GFP– and GFP+CD4+T cells from the LILP by microarray (Table S1). Intriguingly, many of the genes highly expressed in GFP+ cells compared to GFP– cells were characteristic of FOXP3+ Treg cells (Foxp3 (23), Eos (24), Il-10 (25), Cd25 (26)) (Table S1). We confirmed the preferential expression of GPR15 in Tregs by analyzing Foxp3reporter expression in Gpr15gfp/+ Foxp3ires-mrfp mice (FIG. 1A) and also staining for FOXP3 protein (FIG. 6G, 6H). Approximately 60-70% of LILP CD4+FOXP3+ cells expressed Gpr15, compared to only 7-20% of CD4+FOXP3− cells, in mice of two different genetic backgrounds (FIG. 1A, FIG. 6H).

Figure 7C:
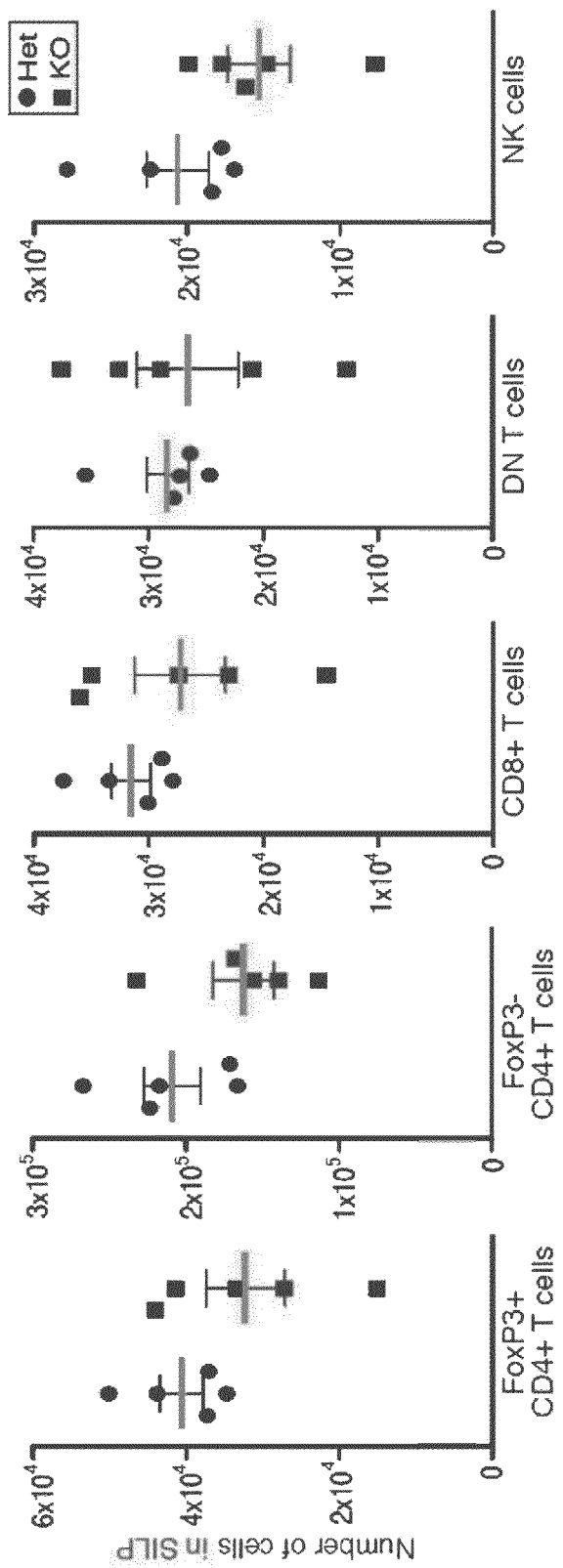

To determine if disproportionate expression of GPR15 in Tregs could affect their presence in the gut, we analyzed T cell populations in Gpr15gfp/gfp and wild-type (WT) mice. We observed a reduction in the Treg percentage specifically in the LILP, but not in the small intestine lamina propria (SILP) or spleen of Gpr15 KO mice (FIG. 1B). This reduced Treg percentage did not affect the proportion of cells expressing HELIOS (FIG. 7A), a marker selectively expressed in thymus-derived (or natural) Treg cells (27), suggesting that natural and inducible Tregs were equally affected. When we analyzed cell numbers, only Tregs, CD8+ T cells, and double-negative (DN) T cells, all of which showed significant GPR15-GFP expression, were markedly reduced in the LILP of Gpr15 KO mice (FIG. 7B), and these populations were unaffected in the SILP (FIG. 7C). There was a significant, but much smaller, reduction in FOXP3− CD4+ T cells (FIG. 7B), such that there was an overall decrease in Treg percentage among total CD4+ T cells in the LILP (FIG. 1B).

Figure 1C:
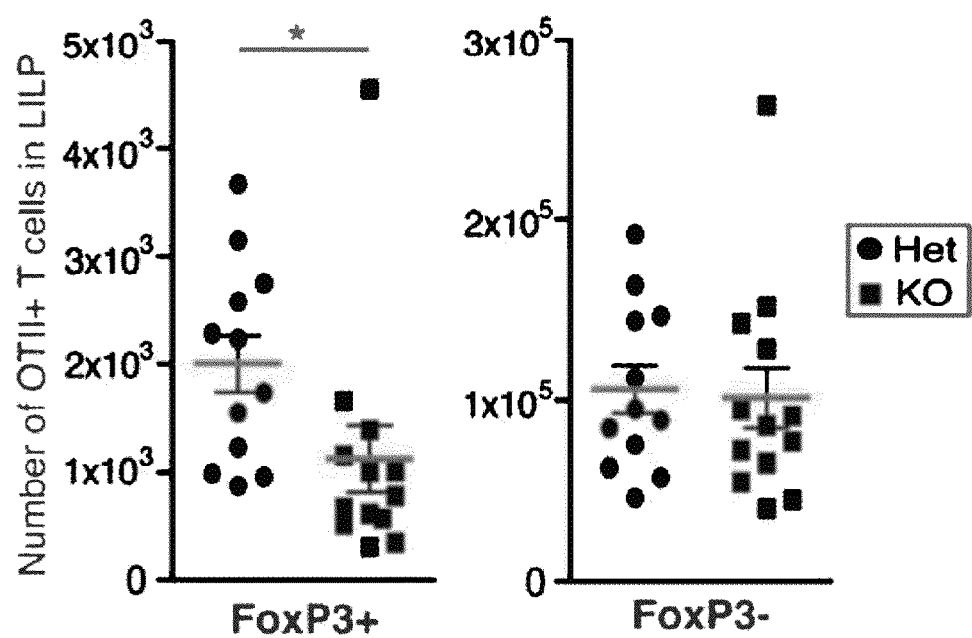

We next examined Treg frequency in the large intestine during an antigen-specific T cell response. Rag2−/−, OT-II TCR transgenic mice that were heterozygous or homozygous for the Gpr15gfp allele were fed with chicken ovalbumin (OVA). Without antigen exposure, all T cells maintained a naive phenotype (CD44lo) and no Treg or GFP+ T cells were observed (FIG. 8A). After OVA exposure of heterozygous mice, there was a small influx in the LILP of GFP+ T cells (2-5%) (FIG. 8A) that was enriched for FOXP3 expression (FIG. 8B). There was a significant reduction in the number of Tregs in the LILP of KO mice, while the number of FOXP3− CD4+ T cells was similar between Het and KO mice (FIG. 1C). Thus, GPR15 preferentially contributes to Treg frequency in the LILP not only at steady state, but also during an antigen-specific T cell response. Furthermore, while the percentage of Tregs was reduced in the LILP of KO mice, it was increased in the spleen of these mice (FIG. 8C), consistent with the possibility that there was defective migration of Tregs into the LILP.

Figure 2A:
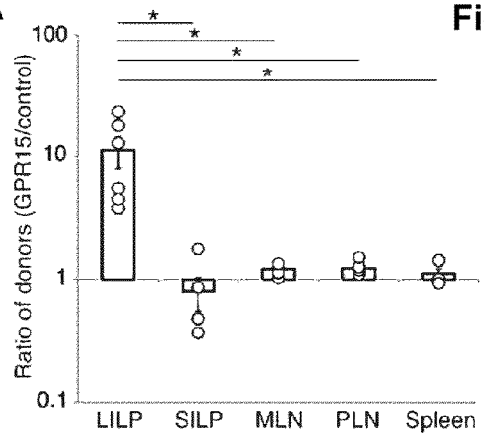
FIG. 2A-2D. GPR15 mediates T cell homing to the LILP. (2A) Ratio of Gpr15-transduced and control-transduced donor cells in different tissues (MLN: Mesenteric lymph nodes; PLN: Inguinal, Brachial, and Axillary lymph nodes) at 10 h after transfer of an equal number of cells (n=6, combined from three independent experiments). (2B) Ratio of Gpr15-transduced cells treated with Pertussis toxin (PTX) and untreated control-transduced cells after co-transfer (n=5). (2C) Ratio of cells transduced with control vector and the R131A mutant Gpr15 fused with gfp (GPR15mut-GFP) (n=7, combined from three independent experiments). (2D) Ratio in different tissues of CD4$^+$ T cells from Gpr15$^{gfp/+}$ (Het) and Gpr15$^{gfp/gfp}$ (KO) mice after in vitro culture in GPR15-inducing conditions and transfer of equal numbers of cells into recipients (n=5, combined from two independent experiments). *p<0.05 (t-test).
Figure 2B:
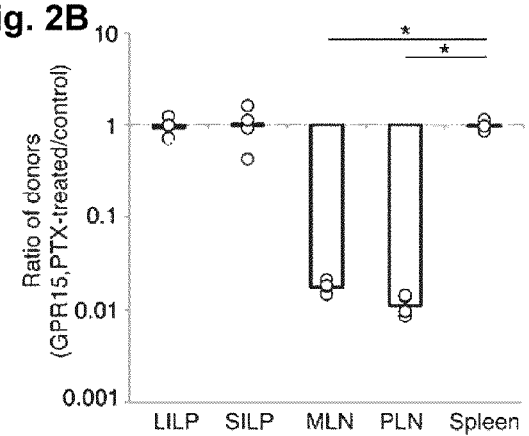
Figure 2C:
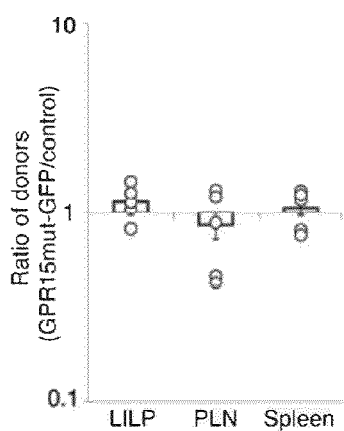
Figure 9A:
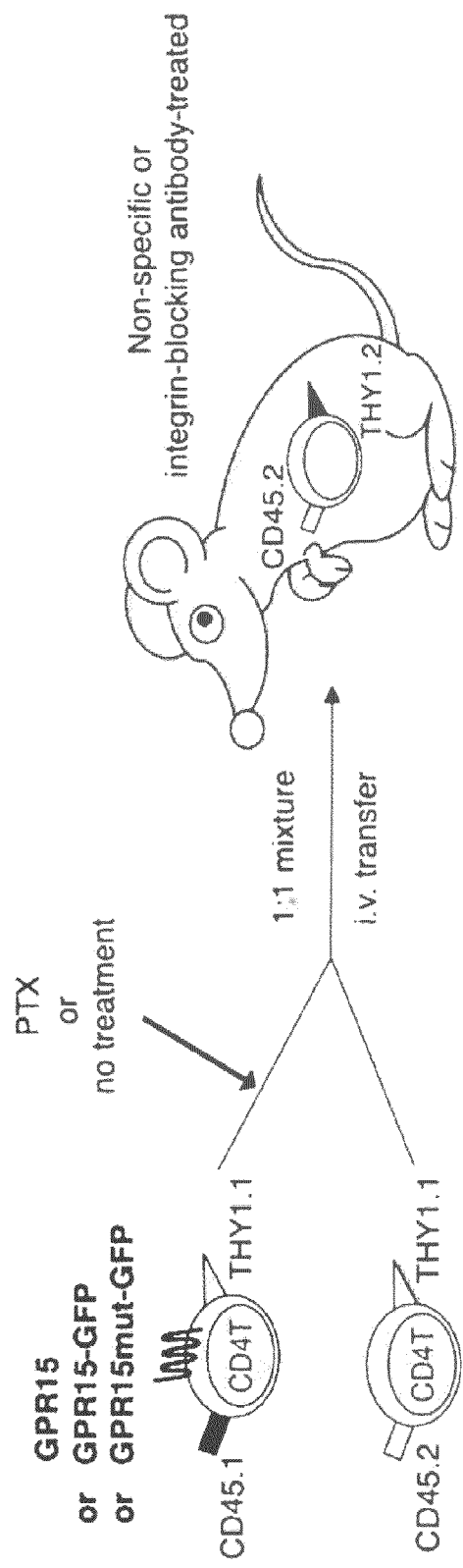
Figure 9C:
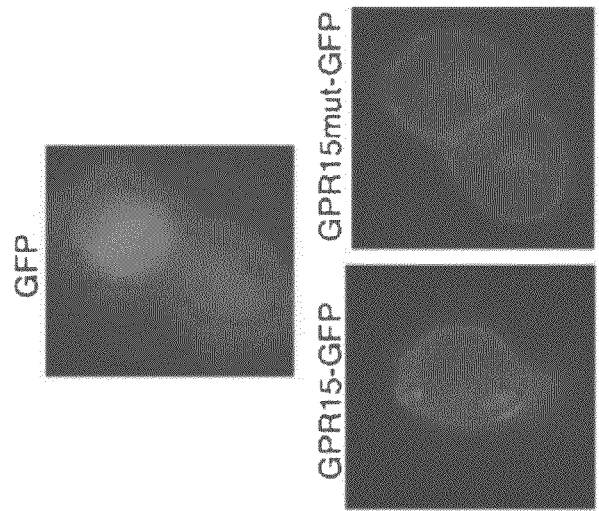
Figure 9B:
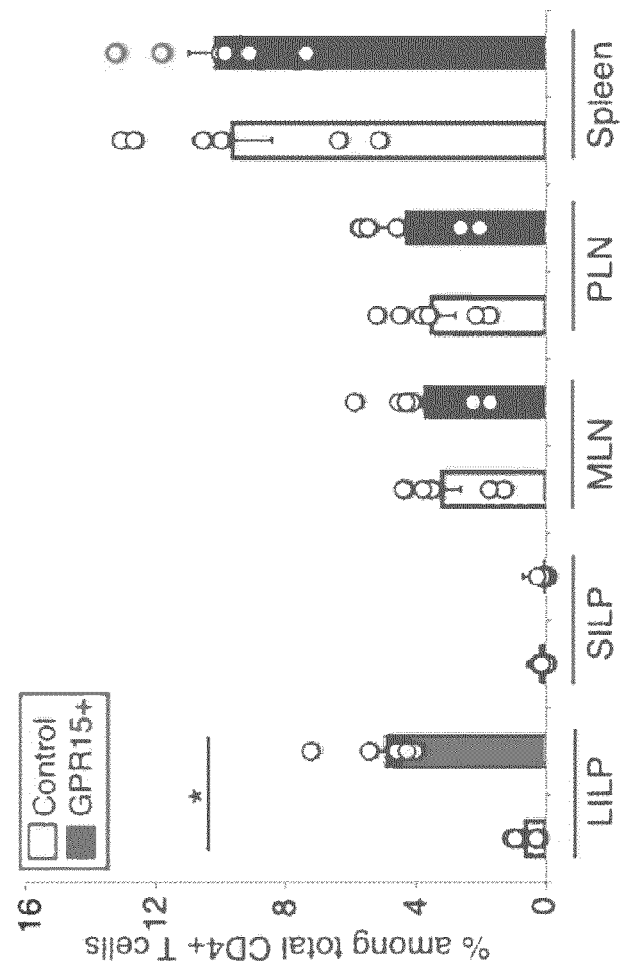

To determine whether GPR15 functions as a homing receptor for the LILP, we performed a short-term competitive homing assay by co-injecting T cells transduced with a control or a GPR15-encoding retrovirus into congenic hosts (FIG. 9A). When GPR15+ cells and control cells were mixed at a 1:1 ratio and transferred into C57BL/6 mice, all tissues examined exhibited a 1:1 ratio of the donor-derived cells, except for the LILP, where there was a ~10-fold enrichment for GPR15+ cells (FIG. 2A, FIG. 9B). There was minimal homing of transferred cells to the small intestine (FIG. 9B), indicating that GPR15 controls homing to the LILP selectively. When GPR15+ cells were treated with the Gαi inhibitor pertussis toxin before transfer, they were no longer enriched in the LILP (FIG. 2B), indicating that GPR15 likely signals through Gαi like other lymphocyte homing receptors. Many GPCRs have in their second intracellular loop a conserved DRY motif that is important for downstream signaling through its interactions with heterotrimeric G proteins (28). To ensure that active signaling through GPR15 is required for homing, we mutated the GPR15 DRY motif to DAY. While both wild-type and R131A mutant proteins fused to GFP were similarly expressed at the cell surface (FIG. 9C), only cells expressing the wild-type fusion protein preferentially migrated to the LILP (FIG. 2C, FIG. 9D), indicating that signaling through GPR15 is required for the LILP homing advantage.

Figure 2D:
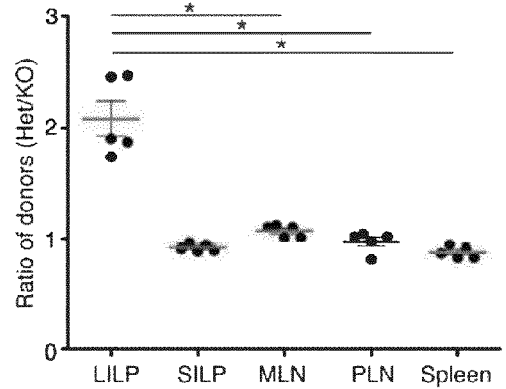
Figure 10:
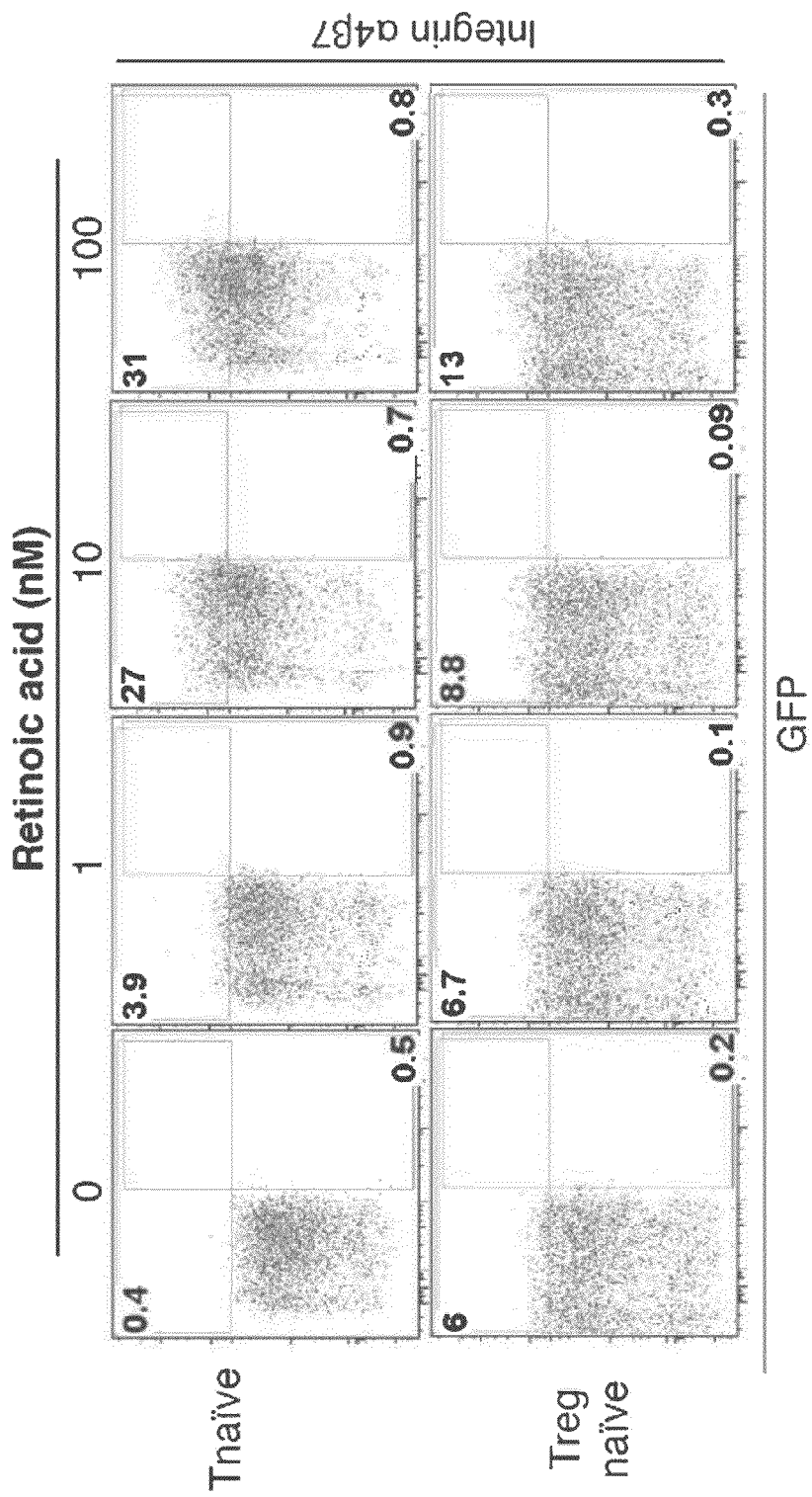
FIG. 10. Retinoic acid does not induce GPR15 expression in vitro. CD4+ GFP− $T_{naive}$ and Tregs with naive phenotype (CD62L$^{hi}$, CD44$^{lo}$) were sorted from Gpr15$^{gfp/+}$ Foxp3$^{ires-mrfp}$ mice and stimulated in the presence of various concentration of retinoic acid for 3 days.
Figure 12A:
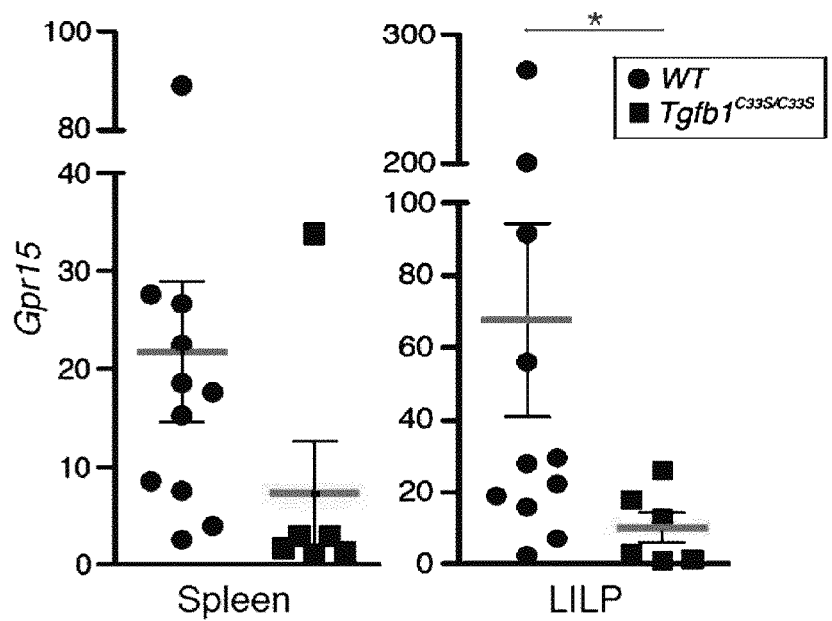
FIG. 12A-12C. GPR15 expression is dependent on TGF-β1 but not on IL-21 or IL-6 in vivo. (12A) Taqman RT-PCR for Gpr15 mRNA in T cells from spleen and LILP of Tgf-beta1$^{C33S/C33S}$ mutant (KI) and wild-type littermate mice (WT), normalized to Beta-actin (n=11(WT), 6(KI), combined results of three independent experiments). (12B) FOXP3+ Treg frequency was examined in spleen and LILP of Tgf-beta1$^{C33S/C33S}$ mutant and wild-type littermate mice (WT). GPR15 expression was reduced in spleen even with a similar frequency of Tregs in KI compared to WT mice. (12C) Gpr15$^{gfp/+}$ mice were crossed to Il6$^{−/−}$Il21r$^{−/−}$ mice to determine the in vivo role of IL-21 and IL-6 on Gpr15 expression. Il6$^{−/−}$Il21r$^{−/−}$ mice had a similar amount of GFP expression as control mice. *p<0.05 (t-test).
Figure 12B:
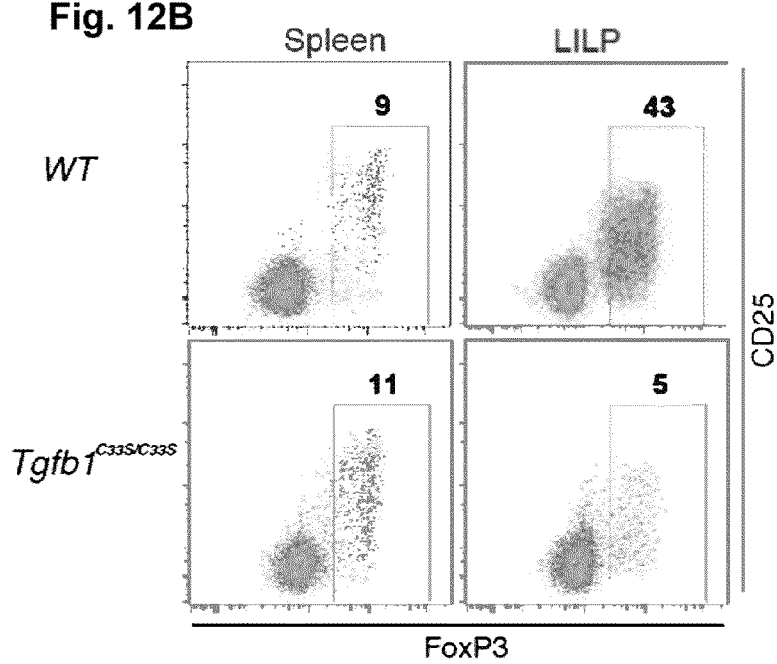
Figure 12C:
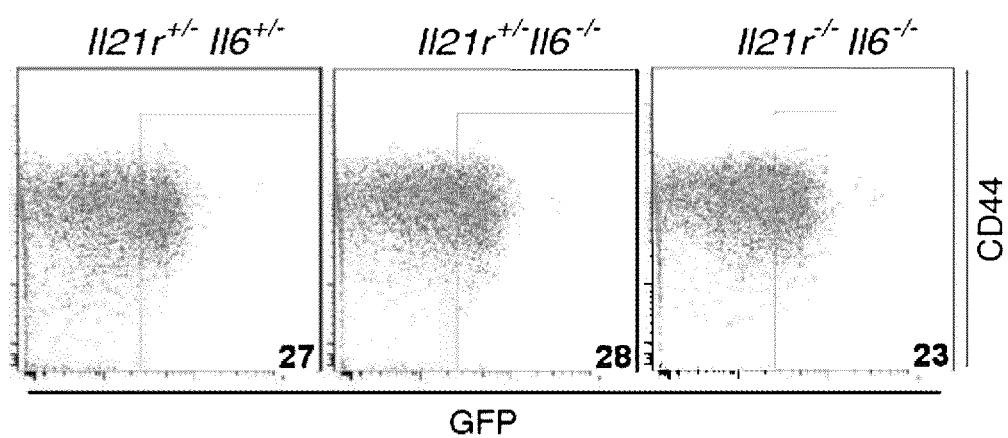

Preferential homing of GPR15+ cells to the LILP was observed as early as 2 h after cell transfer, suggesting that activation of this GPCR may promote integrin-dependent interaction of T cells with the endothelium in the target organ (FIG. 9E). Indeed, blocking antibodies against either subunit of α4β7 inhibited GPR15-mediated homing to the LILP (FIG. 9F). Unlike α4β7 and CCR9, GPR15 was not induced by RA (FIG. 10). However, GPR15 was induced in T cells treated with a combination of TGF-β1 and any one of IL-6 or IL-21 or IL-27 (FIG. 11), and there was a marked decrease in Gpr15 mRNA in T cells of Tgfbeta1C33S/C33S mice that have reduced TGF-β1 in vivo (29) (FIG. 12A, 12B). In contrast, Il21r−/−Il6−/− mice crossed to Gpr15gfp/+ mice had a similar level of GFP expression as control mice (FIG. 12C), suggesting that TGF-β1, but not IL-6 and IL-21, has an important role in GPR15 expression in vivo. Cells from Gpr15 Het and KO mice were treated with these cytokines to induce GPR15 expression in vitro and were used in the short-term competitive homing assay (FIG. 2D). The results confirmed the importance of endogenously-expressed GPR15 in the homing of T cells to the LILP.

Figure 13A:
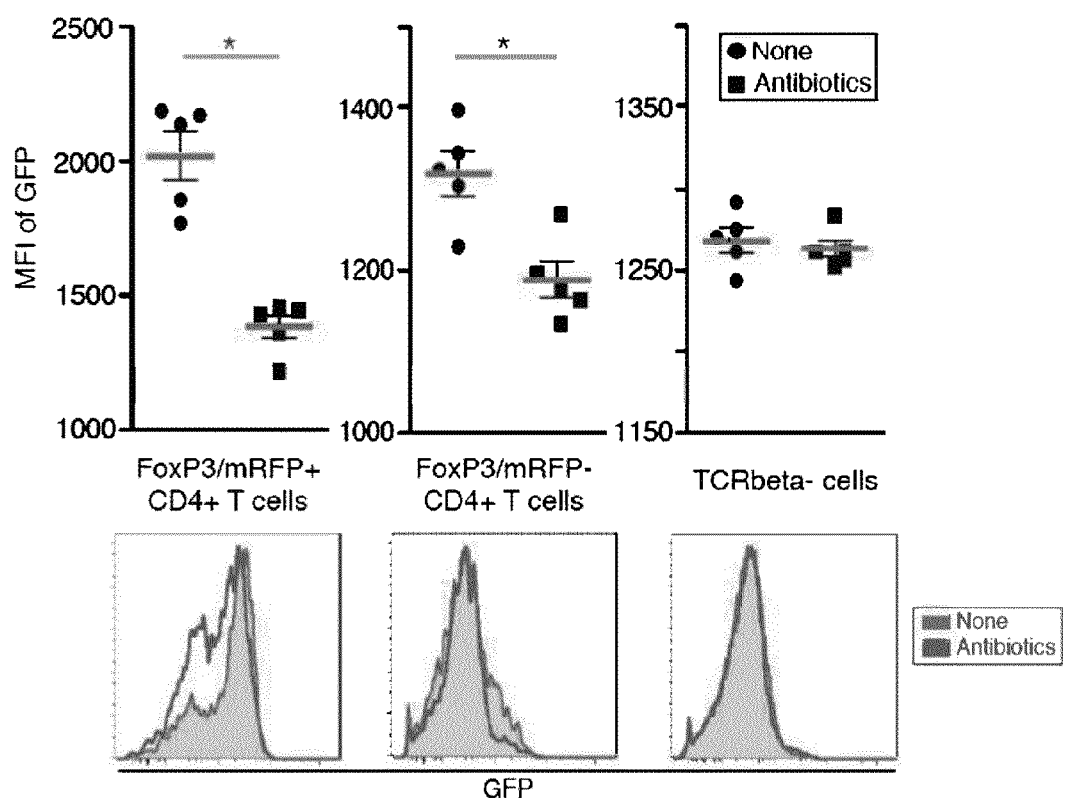
FIG. 13A-13C. Gut microbiota promotes GPR15 expression, but is not required for production of chemoattractant. (13A) Gpr15$^{gfp/+}$, Foxp3$^{ires-mrfp}$ mice were treated with a combination of antibiotics in the drinking water from birth. Mean fluorescence intensity (MFI) of GFP was examined in each cell type from the LILP (n=5, representative of three independent experiments). Representative histograms for each cell type are shown below. (13B, 13C) Competitive homing assays were performed as described in FIG. 9A. (13B) Specific pathogen-free (SPF) or germ-free (GF) mice were used as recipients. (13C) Specific pathogen-free mice (None) or mice treated with a combination of antibiotics were used as recipients. GPR15+ cells preferentially homed to the LILP in GF and antibiotics-treated mice, indicating that GPR15 ligand production is not dependent on gut microbiota.
Figure 13B:
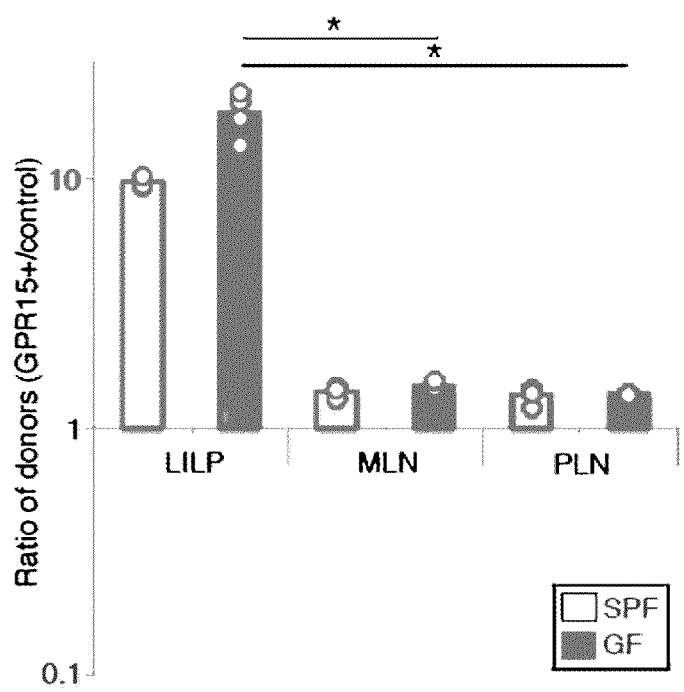
Figure 13C:
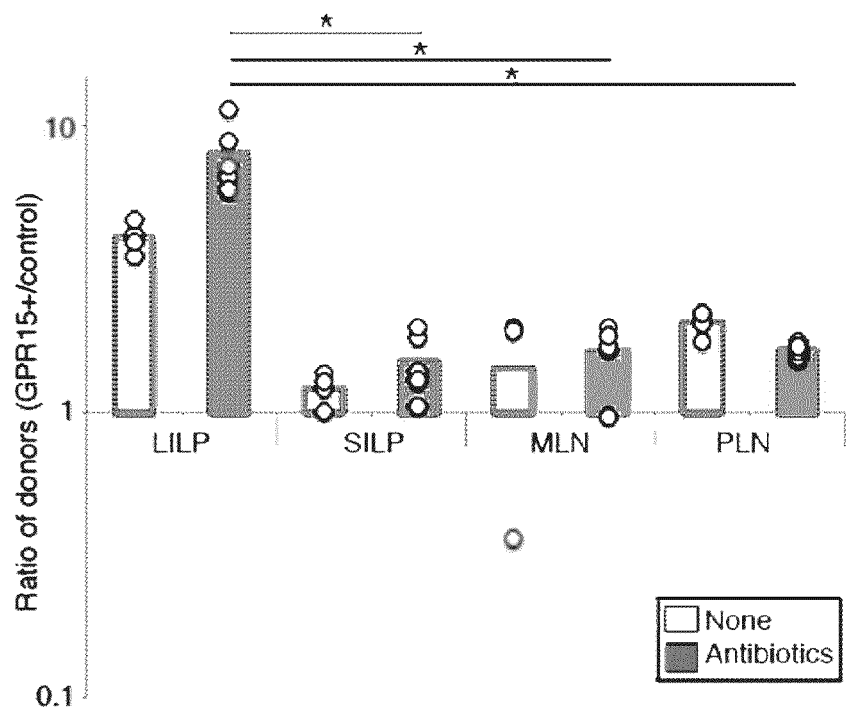

We also tested the effect of gut microbiota on GPR15-mediated homing of T cells to the LILP. Treatment of Gpr15gfp/+ mice with a combination of broad-spectrum antibiotics led to a marked decrease in GPR15 expression (FIG. 13A). In contrast, GPR15-overexpressing T cells preferentially migrated to the LILP even in germfree or antibiotics-treated recipients (FIG. 13B, 13C). Therefore, microbiota can affect GPR15 expression, possibly through regulation of specific cytokines such as TGF-β1(7), but production of a ligand(s) for GPR15 appears to be independent of the microbiota.

Figure 3A:
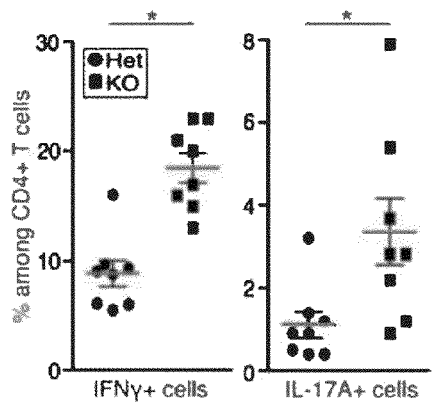
FIG. 3A-3H. Mice deficient for GPR15 are prone to inflammation of the large intestine due to a defect in Tregs. (3A) Percentage of IFNγ$^+$ or IL-17$^+$ CD4$^+$ T cells in the LILP at steady state in Gpr15 heterozygous or KO mice (9-11 wks old in B6/129SvEv mixed background; n=8, combined from three independent experiments). (3B) Taqman RT-PCR of inflammatory cytokines/chemokine in the LILP of het and KO mice at day 3 after injection of αCD40 antibody (n=5). (3C-H) Results after infection of mice with C. rodentium. (3C) Kaplan-Meier survival curve of wild-type (WT) and KO mice (WT: n=9; KO: n=22, combined from three independent experiments). (3D) Weight change (n=6-8, representative of three independent experiments) (3E, 3F) H&E staining of colon sections (Bar=70 μm) of C. rodentium-infected Het and KO mice (3E) or of chimeric mice reconstituted with bone marrow progenitors for GPR15-sufficient (WT) or -deficient (KO) Tregs (3F). (3G, 3H) Histology score and inflammation index of colons of Het and KO mice (3G) or of mixed bone marrow chimeras (3H) (n=5-6 per group). *p<0.05 (t-test), **p<0.05 (Log-rank test).
Figure 3B:
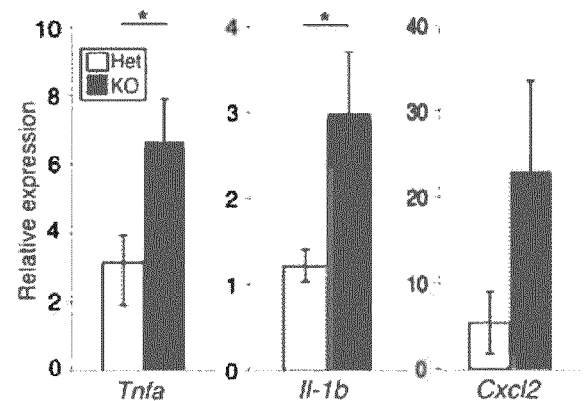
Figure 14A:
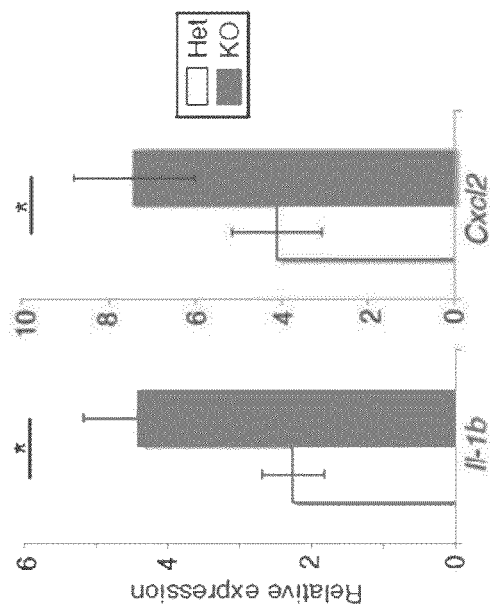
FIG. 14A-14E. Influence of GPR15 on cytokine production during inflammation and on Treg cell function. (14A) Taqman RT-PCR of inflammatory cytokines/chemokine (Tn-falpha, Il-1beta, Cxcl2) in spleen at day 3 after injection of αCD40 (FGK 45) antibody (200-300 µg) into Gpr15$^{gfp/+}$ (Het) and Gpr15$^{gfp/gfp}$ (KO) mice. Relative expression level was normalized to Beta-actin (n=4-5). (14B-14D) Results of infection of mice with 8×10$^9$ C. rodentium by gavage. (14B) Taqman RT-PCR of inflammatory cytokine/chemokine (Il-1 beta, Cxcl2) in colon at day 10, normalized to Beta-actin (n=11). (14C) FOXP3+ regulatory T cell numbers in LILP at day 10 after Citrobacter infection (n=5-8). (14D) Bacterial colony forming units/g weight of colon and spleen at day 9 (n=11-15). (14E) FOXP3/mRFP+ regulatory T cells in spleen and lymph nodes or LILP from Foxp3$^{ires-mrfp}$ and Foxp3$^{ires-mrfp}$ Gpr15$^{gfp/gfp}$ mice were sorted and tested for their suppressive activity in vitro. *p<0.05 (t-test).

Since GPR15 deficiency affected Treg homing to the LILP, we next investigated its role in immune homeostasis in the large intestine. We first examined cytokine production by CD4+ T cells in the large intestines of Gpr15 Het and KO mice. At steady state there was an increased proportion of IFN-γ- and IL-17A-producing cells among total CD4+ T cells in the LILP of Gpr15 KO mice on a 129/B6 mixed background (FIG. 3A). In C57BL/6-backcrossed mice, this spontaneous, steady state phenotype was not evident. However, when C57BL/6-backcrossed mice were injected with anti-CD40 antibody (which induces acute colitis in Rag2−/− mice (30)), inflammatory cytokine expression in the large intestine (but not spleen) was higher in Gpr15 KO mice than in littermate controls (FIG. 3B, FIG. 14A). Thus, regardless of the genetic background, Gpr15 knockout mice are prone to express more inflammatory cytokines in the large intestine.

Figure 3C:
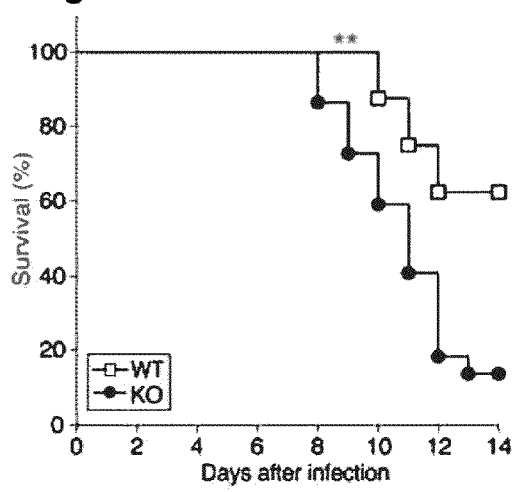
Figure 3D:
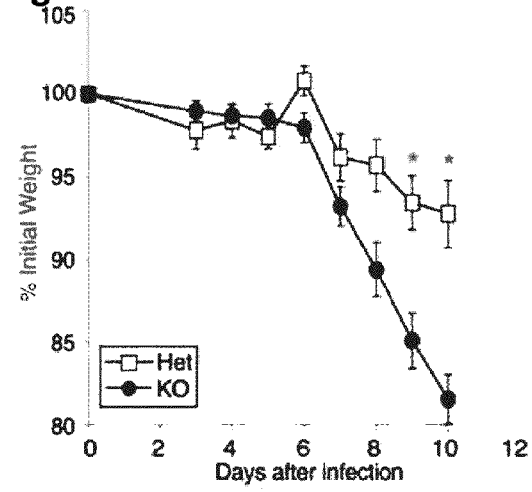
Figure 3E:
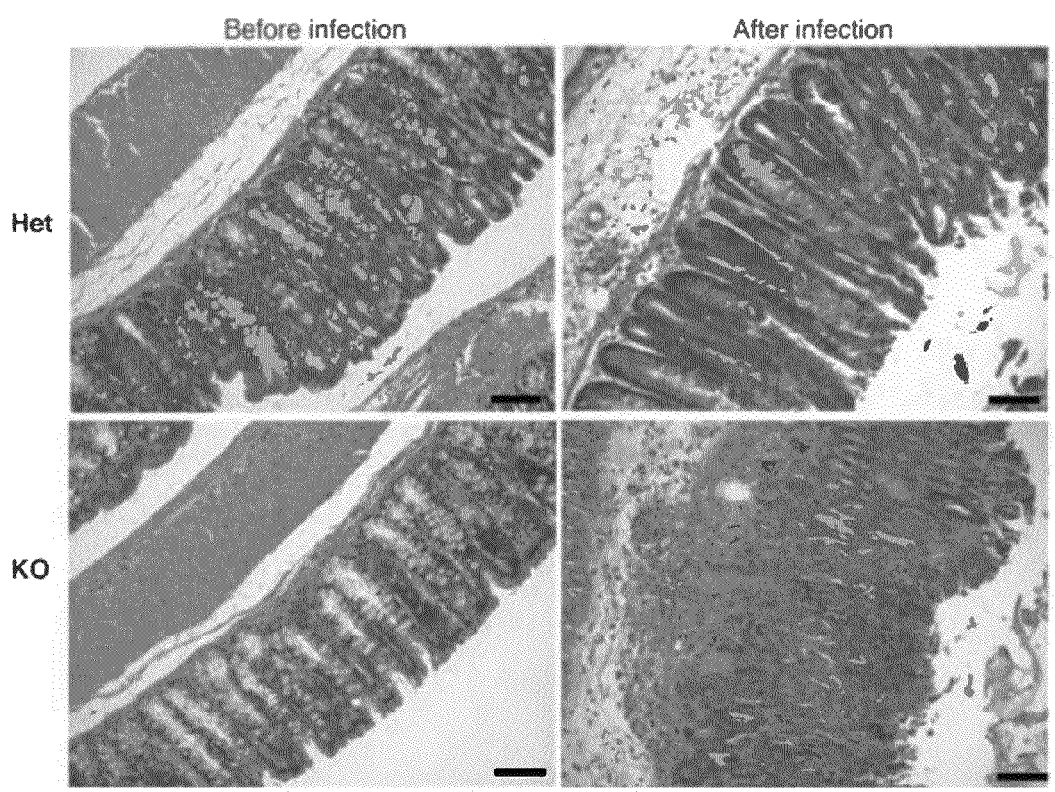
Figure 3F:
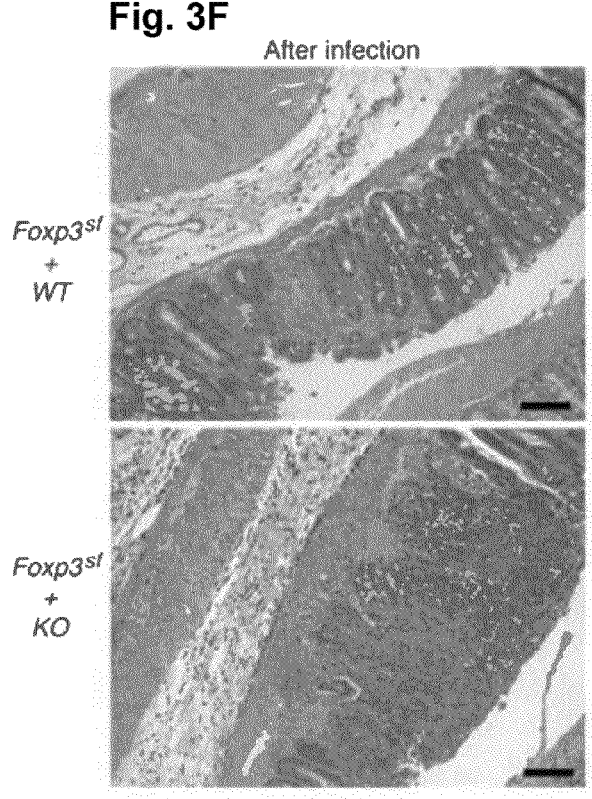
Figure 3G:
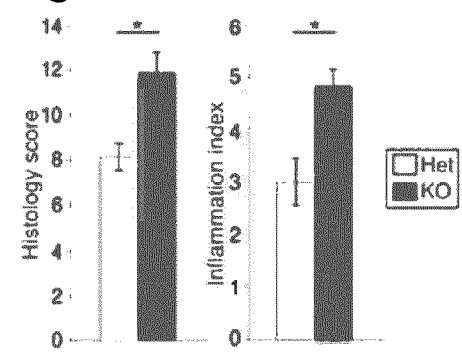
Figure 14B:
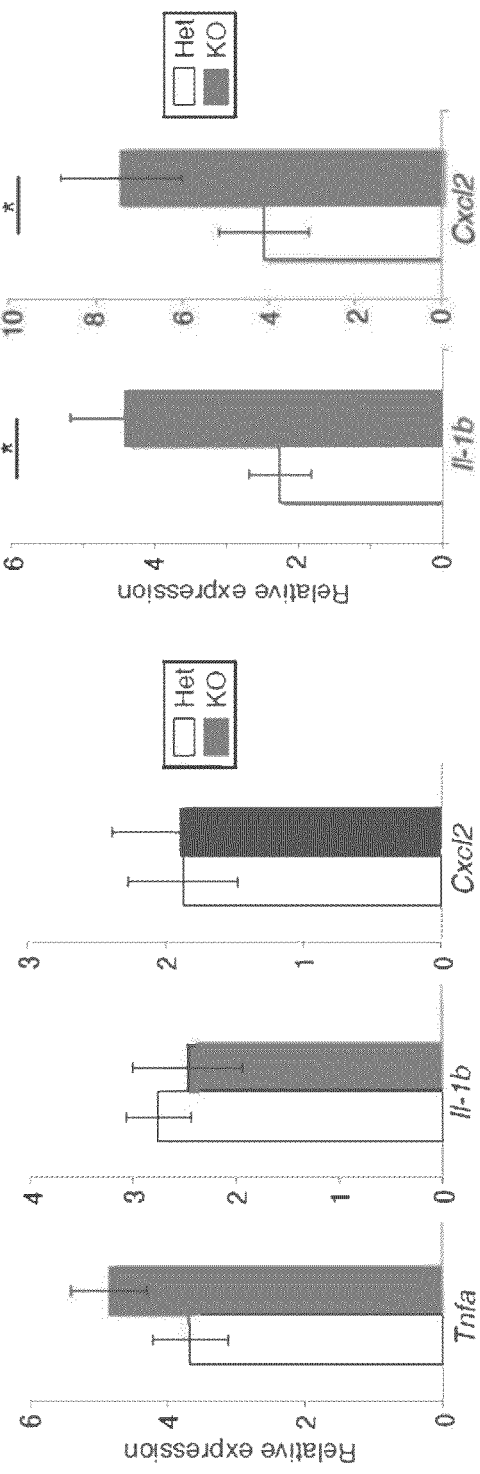
Figure 14C:
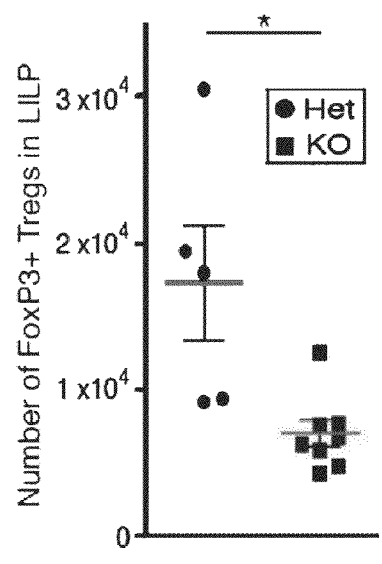
Figure 14D:
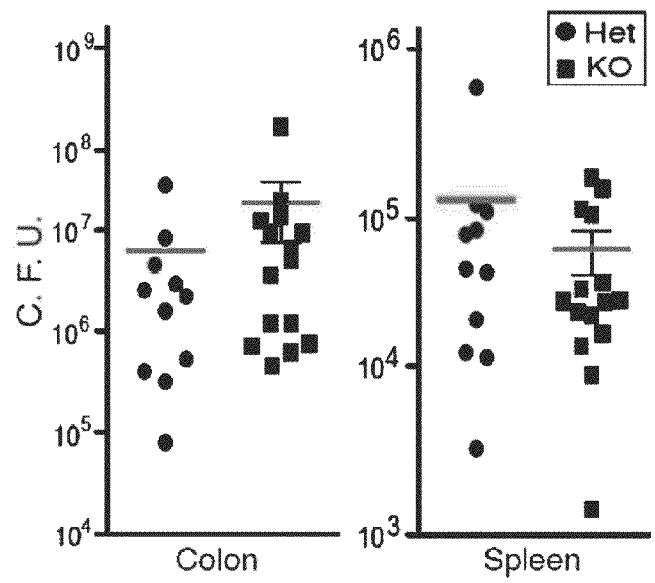

We next tested the physiological consequences of this inflammatory phenotype in an infection induced colitis model. When mice were infected with *Citrobacter rodentium*, the majority of wild-type mice resolved inflammation and survived. In contrast, most Gpr15 knockout mice suffered severe weight loss and died rapidly (FIG. 3C, 3D). KO mice also exhibited increased inflammation, tissue damage and inflammatory cytokine expression, all of which are indicative of severe colitis (FIG. 3E, 3G, FIG. 14B), and Treg numbers were reduced compared to Het mice (FIG. 14C). Importantly, there was no difference in *Citrobacter* number recovered from the large intestine and spleen of Het and KO mice (FIG. 14D), indicating that GPR15 is not required for controlling the infection, but rather for dampening the immune response in the large intestine.

Figure 3H:
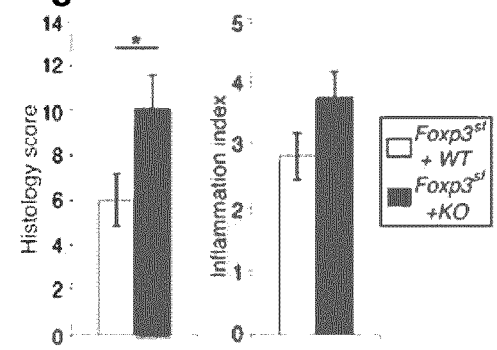
Figure 14E:
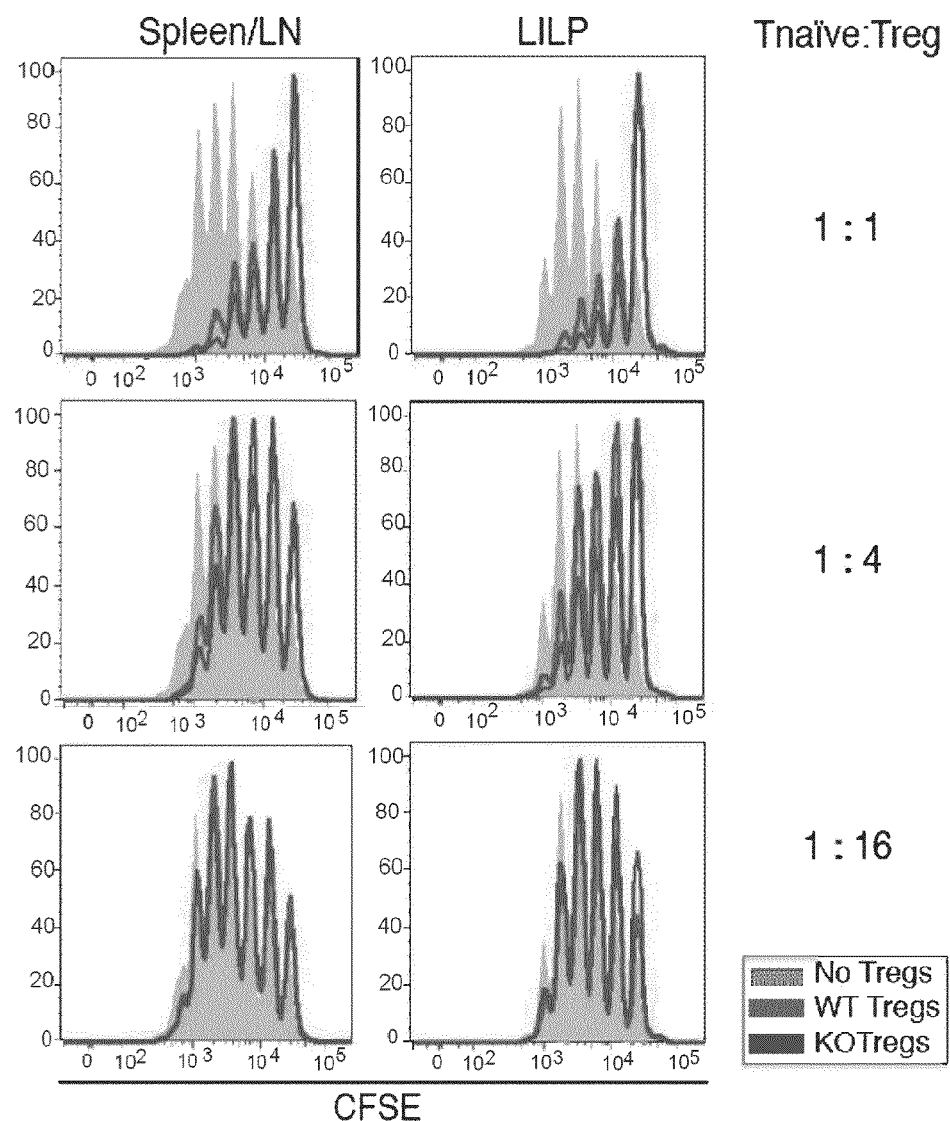

To confirm that sensitivity to *Citrobacter* infection was due to a role of GPR15 in Tregs rather than other T cells, we infected mice that received mixed bone marrow from Foxp3sf and from either wild-type or Gpr15 KO mice. In Foxp3sfx Gpr15 KO mixed chimeras, Tregs will develop only from Gpr15 KO bone marrow and will thus lack GPR15 expression, while other T cells can develop from GPR15-sufficient Foxp3sf bone marrow. Indeed, mixed chimeric mice reconstituted withTregs from Gpr15 KO bone marrow exhibited more severe inflammation and tissue damage than did chimeras generated with WT bone marrow (FIG. 3F, 3H), indicating that GPR15 expression in Tregs is required to prevent severe colitis following *Citrobacter* infection. This phenotype was not due to a role of GPR15 in regulating Treg function, since WT Tregs and KO Tregs isolated from spleen/lymph nodes and LILP suppressed naive T cell proliferation equally well (FIG. 14E). These results indicate that GPR15 is critical for Treg homing to the LILP and for preventing pathological inflammation in the large intestine during colitis.

Figure 4A:
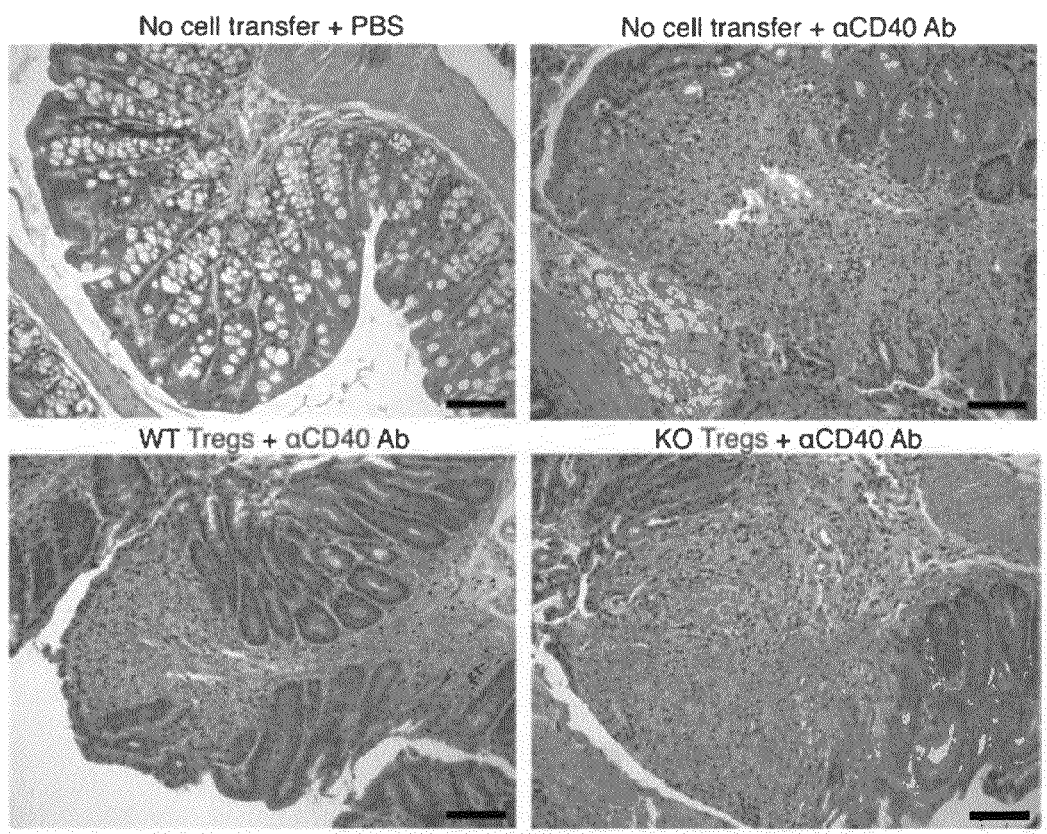
FIG. 4A-4D. Regulatory T cells from GPR15-deficient mice cannot rescue colitis. (4A, 4B) Rag2$^{-/-}$ mice received 5×10$^5$ mRFP$^+$ Tregs transferred from either Foxp3$^{ires-mrfp}$ or Gpr15$^{gfp/gfp}$ Foxp3$^{ires-mrfp}$ mice and were subsequently injected with αCD40 antibody. (4A) H&E staining of proximal and mid colon section of mice without any treatment, with colitis induction alone, or with colitis induction and rescue by wild-type or KO Tregs (Bar=70 μm) (4B) Histology scores (n=7-12, combined from two independent experiments). (4C, 4D) H. hepaticus-infected Rag2$^{-/-}$ mice received 3×10$^5$ CD4$^+$ T$_{naïve}$ cells transferred either from Foxp3$^{ires-mrfp}$ mice or Gpr15$^{gfp/gfp}$ Foxp3$^{ires-mrfp}$ mice. (4C) Histology scores. (4D) H&E staining of distal colon section of either Rag2$^{-/-}$ without any treatment (None), with wild-type T$_{naïve}$ transfer, or with KO T$_{naïve}$ transfer (Bar=70 μm). *p<0.05 (t-test).
Figure 4B:
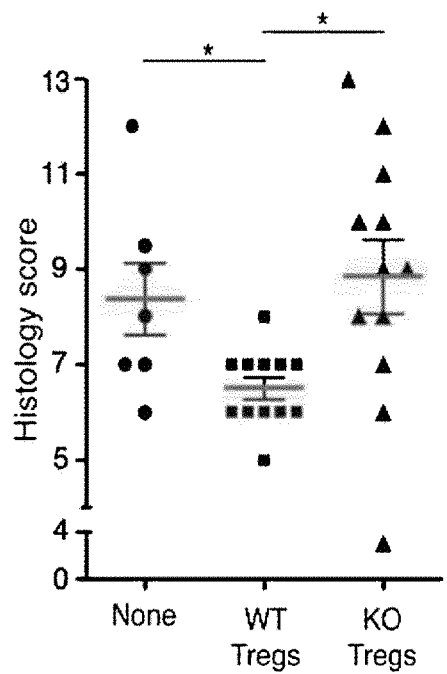
Figure 4C:
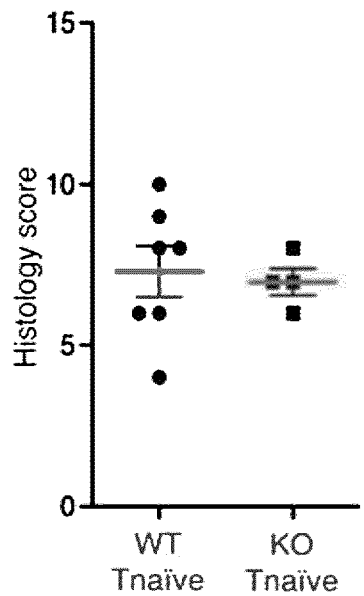
Figure 4D:
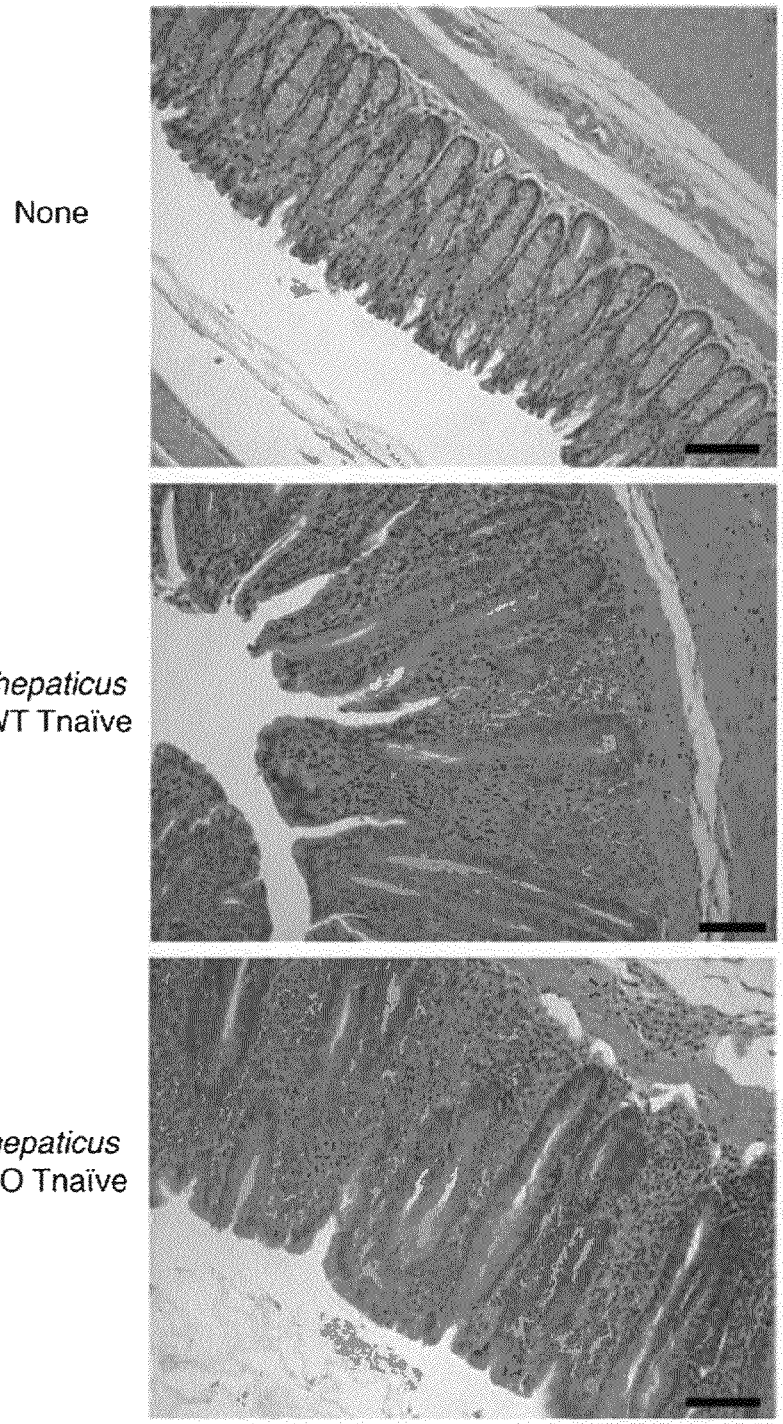

We additionally used a non-infectious model of colitis to determine the role of GPR15 in suppressing local inflammation in vivo. CD40 stimulation in the absence of adaptive immunity induces innate immune cell-mediated colitis (30) that can be rescued by introduction of Tregs (31, 32). We therefore transferred Tregs from Gpr15 WT or KO mice into Rag2−/− mice (30) that were subsequently treated with anti-CD40 antibody (FGK45), and we monitored the extent of the colitis. The transfer of WT Treg, but not KO Tregs, reduced colitis severity and tissue damage (FIG. 4A, 4B), indicating that GPR15 is required for Treg-mediated control of local inflammation in the large intestine. We also determined the ability of naive T cells from Gpr15 WT and KO mice to induce colitis after *Helicobacter hepaticus* infection (31). In this T cell transfer colitis model, which is dependent on the absence of Tregs, KO T naive cells induced colitis as well as their WT counterpart (FIG. 4C, D), consistent with a preferential role for GPR15 in regulating the homing of Tregs.

To determine whether the function of GPR15 as a homing receptor for the large intestine is conserved between human and mouse, we examined GPR15 mRNA expression in different cell types from various human tissues. While GPR15 expression was minimal in lymphocytes from the blood and the small intestine, it was expressed at high levels in lymphocytes from the large intestine (FIG. 15), suggesting that a role of GPR15 as a selective homing receptor for the large intestine is conserved between mouse and human. However, we did not detect elevated GPR15 mRNA expression in the Treg-enriched CD25+CD4+ T cell population relative to other LILP T cell populations. Rather, there was more GPR15 mRNA in CD25-CD4+ T cells than in CD25+CD4+ T cells. One caveat of this study is that all colon samples were from colorectal carcinoma patients. Studies are ongoing to examine GPR15 expression in colonic lymphocytes from normal subjects or IBD patients and to examine a role of GPR15 in HIV-mediated enteropathy (33, 34).

Figure 16A:
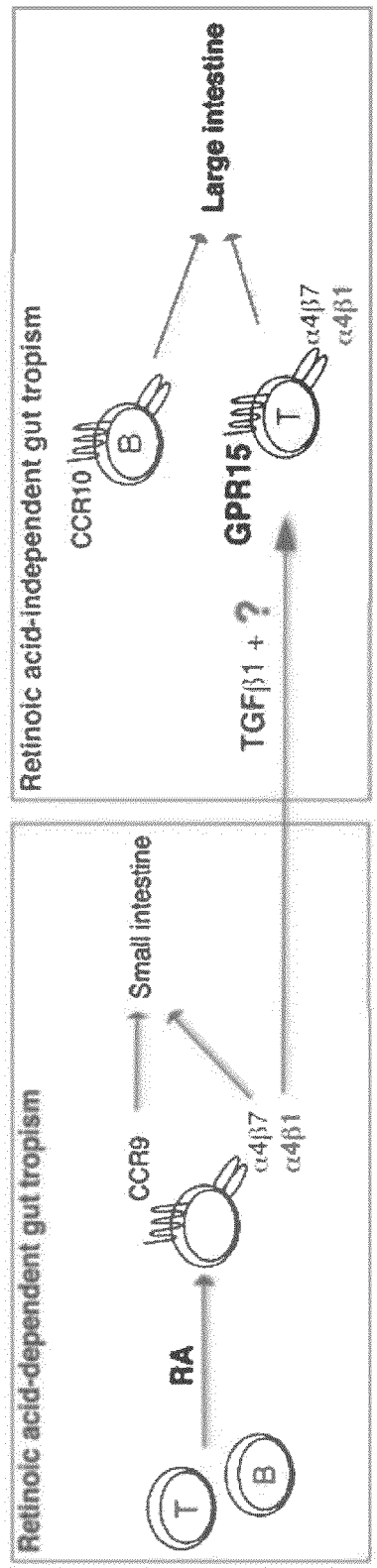

Our results provide the first example of a homing receptor specific for T cell migration to the large intestine. The receptor, GPR15, was found to be crucial for immune homeostasis in the large intestine mucosa. We also showed that the small and large intestine utilize different homing cues and different homing receptors for adaptive immune cells (FIG. 16A), and thereby compartmentalize immune tolerance mediated by Tregs (FIG. 16B). Our results provide a better understanding of immune homeostasis in the intestinal mucosa and could potentially lead to new therapeutic strategies to treat inflammatory diseases by combining in vitro expansion of Tregs and GPR15 induction for re-introduction into patients.

While certain of the particular embodiments of the present invention have been described and specifically exemplified above, it is not intended that the invention be limited to such embodiments. Various modifications may be made thereto without departing from the scope and spirit of the present invention, as set forth in the following claims.

REFERENCES AND NOTES

1. S. K. Mazmanian, C. H. Liu, A. O. Tzianabos, D. L. Kasper, An immunomodulatory molecule of symbiotic bacteria directs maturation of the host immune system, *Cell* 122, 107-118 (2005).
2. N. Kamada et al., Regulated virulence controls the ability of a pathogen to compete with the gut microbiota, *Science* 336, 1325-1329 (2012).
3. R. E. Ley, C. A. Lozupone, M. Hamady, R. Knight, J. I. Gordon, Worlds within worlds: evolution of the vertebrate gut microbiota, *Nat Rev Microbiol* 6, 776-788 (2008).
4. L. V. Hooper, D. R. Littman, A. J. Macpherson, Interactions between the microbiota and the immune system, *Science* 336, 1268-1273 (2012).
5. B. A. Duerkop, S. Vaishnava, L. V. Hooper, Immune responses to the microbiota at the intestinal mucosal surface, *Immunity* 31, 368-376 (2009).
6. M. A. McGuckin, S. K. Linden, P. Sutton, T. H. Florin, Mucin dynamics and enteric pathogens, *Nat Rev Microbiol* 9, 265-278 (2011).
7. K. Atarashi et al., Induction of colonic regulatory T cells by indigenous *Clostridium* species, *Science* 331, 337-341 (2011).
8. S. K. Lathrop et al., Peripheral education of the immune system by colonic commensal microbiota, *Nature* 478, 250-254 (2011).
9. M. B. Geuking et al., Intestinal bacterial colonization induces mutualistic regulatory T cell responses, *Immunity* 34, 794-806 (2011).
10. K. J. Maloy, F. Powrie, Intestinal homeostasis and its breakdown in inflammatory bowel disease, *Nature* 474, 298-306 (2011).
11. W. W. Agace, T-cell recruitment to the intestinal mucosa, *Trends in Immunology* 29, 514-522 (2008).
12. J. R. Mora, M. Iwata, U. H. von Andrian, Vitamin effects on the immune system: vitamins A and D take centre stage, *Nat Rev Immunol* 8, 685-698 (2008).
13. H. Sigmundsdottir, E. C. Butcher, Environmental cues, dendritic cells and the programming of tissue-selective lymphocyte trafficking, *Nat Immunol* 9, 981-987 (2008).
14. M. Iwata et al., Retinoic acid imprints gut-homing specificity on T cells, *Immunity* 21, 527-538 (2004).
15. J. R. Mora et al., Generation of gut-homing IgA-secreting B cells by intestinal dendritic cells, *Science* 314, 1157-1160 (2006).
16. D. Mucida et al., Reciprocal TH17 and regulatory T cell differentiation mediated by retinoic acid, *Science* 317, 256-260 (2007).
17. M. J. Benson, K. Pino-Lagos, M. Rosemblatt, R. J. Noelle, All-trans retinoic acid mediates enhanced T reg cell growth, differentiation, and gut homing in the face of high levels of co-stimulation, *J Exp Med* 204, 1765-1774 (2007).
18. J. L. Coombes et al., A functionally specialized population of mucosal CD103+ DCs induces Foxp3+ regulatory T cells via a TGF-beta and retinoic acid-dependent mechanism, *J Exp Med* 204, 1757-1764 (2007).
19. C.-M. Sun et al., Small intestine lamina propria dendritic cells promote de novo generation of Foxp3 T reg cells via retinoic acid, *J Exp Med* 204, 1775-1785 (2007).
20. A. M. Bilate, J. J. Lafaille, Induced CD4(+)Foxp3(+) Regulatory T Cells in Immune Tolerance, *Annu Rev Immunol* 30, 733-758 (2012).

21. H. K. Deng, D. Unutmaz, V. N. Kewalramani, D. R. Littman, Expression cloning of new receptors used by simian and human immunodeficiency viruses, *Nature* 388, 296-300 (1997).
22. M. Farzan et al., Two orphan seven-transmembrane segment receptors which are expressed in CD4-positive cells support simian immunodeficiency virus infection, *J Exp Med* 186, 405-411 (1997).
23. J. D. Fontenot, M. A. Gavin, A. Y. Rudensky, Foxp3 programs the development and function of CD4+CD25+ regulatory T cells, *Nat Immunol* 4, 330-336 (2003).
24. F. Pan et al., Eos mediates Foxp3-dependent gene silencing in CD4+ regulatory T cells, *Science* 325, 1142-1146 (2009).
25. C. Asseman, S. Mauze, M. W. Leach, R. L. Coffman, F. Powrie, An essential role for interleukin 10 in the function of regulatory T cells that inhibit intestinal inflammation, *J Exp Med* 190, 995-1004 (1999).
26. S. Sakaguchi, N. Sakaguchi, M. Asano, M. Itoh, M. Toda, Immunologic self-tolerance maintained by activated T cells expressing IL-2 receptor alpha-chains (CD25). Breakdown of a single mechanism of self-tolerance causes various autoimmune diseases, *J Immunol* 155, 1151-1164 (1995).
27. A. Thornton et al., Expression of Helios, an Ikaros Transcription Factor Family Member, Differentiates Thymic-Derived from Peripherally Induced Foxp3+ T Regulatory Cells, *The Journal of Immunology* 184, 3433 (2010).
28. G. E. Rovati, V. Capra, R. R. Neubig, The highly conserved DRY motif of class A G protein-coupled receptors: beyond the ground state, *Molecular Pharmacology* 71, 959-964 (2007).
29. K. Yoshinaga et al., Perturbation of transforming growth factor (TGF)-ss1 association with latent TGF-beta binding protein yields inflammation and tumors, *Proc Natl Acad Sci USA* 105, 18758-18763 (2008).
30. H. H. Uhlig et al., Differential Activity of IL-12 and IL-23 in Mucosal and Systemic Innate Immune Pathology, *Immunity* 25, 309-318 (2006).
31. K. J. Maloy et al., CD4+CD25+ T(R) cells suppress innate immune pathology through cytokine-dependent mechanisms, *J Exp Med* 197, 111-119 (2003).
32. W. S. Garrett et al., Communicable Ulcerative Colitis Induced by T-bet Deficiency in the Innate Immune System, *Cell* 131, 33-45 (2007).
33. J. M. Brenchley, D. C. Douek, HIV infection and the gastrointestinal immune system, *Mucosal immunology* 1, 23-30 (2008).
34. A. J. Chase et al., Severe depletion of CD4+CD25+ regulatory T cells from the intestinal lamina propria but not peripheral blood or lymph nodes during acute simian immunodeficiency virus infection, *J Virol* 81, 12748-12757 (2007).
35. Y. Y. Wan, R. A. Flavell, Identifying Foxp3-expressing suppressor T cells with a bicistronic reporter, *Proc Natl Acad Sci USA* 102, 5126-5131 (2005).
36. M. E. Brunkow et al., Disruption of a new forkhead/winged-helix protein, scurfin, results in the fatal lymphoproliferative disorder of the scurfy mouse, *Nat Genet* 27, 68-73 (2001).
37. J. H. Niess et al., CX3CR1-mediated dendritic cell access to the intestinal lumen and bacterial clearance, *Science* 307, 254-258 (2005).
38. T. C. Mitchell et al., Immunological adjuvants promote activated T cell survival via induction of Bcl-3, *Nat Immunol* 2, 397-402 (2001).
39. L. W. Collison, D. A. A. Vignali, In vitro Treg suppression assays, *Methods Mol Biol* 707, 21-37 (2011).
40. J. Rivera-Nieves et al., L-selectin, alpha 4 beta 1, and alpha 4 beta 7 integrins participate in CD4+ T cell recruitment to chronically inflamed small intestine, *J Immunol* 174, 2343-2352 (2005).
41. B. Cassani et al., Gut-tropic T cells that express integrin α4β7 and CCR9 are required for induction of oral immune tolerance in mice, *Gastroenterology* 141, 2109-2118 (2011).

What is claimed is:

1. A method for generating a population of CD4+CD3+CD25+T cells that migrates preferentially to the large intestine, the method comprising the steps of: isolating a population of CD4+CD3+CD25+ T cells from a mammal; and incubating the population of CD4+CD3+CD25+ T cells in culture medium comprising TGF-β and IL-21 to produce a population of CD4+CD3+CD25+T cells having enhanced GPR15 expression, wherein the enhanced GPR15 expression confers on the population of CD4+CD3+CD25+T cells an ability to migrate preferentially to the large intestine.

2. The method of claim 1, wherein the culture medium comprises TGF-β at a concentration of at least 0.1 ng/ml and IL-21 at a concentration of at least 0.1 ng/ml.

3. The method of claim 1, wherein the culture medium comprises TGF-β at a concentration of about 5-20 ng/ml and IL-21 at a concentration of about 10-20 ng/ml.

4. The method of claim 1, wherein the culture medium further comprises IL-2.

5. The method of claim 1, further comprising administering the population of CD4+CD3+CD25+T cells having enhanced GPR15 expression and ability to migrate preferentially to the large intestine to the mammal, wherein the mammal is afflicted with an inflammatory condition of the large intestine.

6. The method of claim 5, wherein the inflammatory condition of the large intestine is inflammatory bowel disease, idiopathic colitis, or infectious colitis.

7. The method of claim 6, wherein the inflammatory bowel disease is Crohn's disease or ulcerative colitis.

8. The method of claim 1, further comprising anti-CD3/CD28 activating agents in the incubating step.

9. The method of claim 1, wherein the mammal is a human.

10. The method of claim 1, wherein the culture medium does not comprise retinoic acid.

11. A population of CD4+CD3+CD25+T cells having enhanced GPR15 expression and ability to migrate preferentially to the large intestine and a composition thereof further comprising a pharmaceutically acceptable carrier, wherein the population is generated in accordance with the method of claim 1.

12. A population of CD4+CD3+CD25+T cells having enhanced GPR15 expression and ability to migrate preferentially to the large intestine, wherein the population comprises a nucleic acid sequence encoding exogenous GPR15 or a composition of said cells further comprising a pharmaceutically acceptable carrier.

13. A method of treating a mammal in need thereof comprising administering the population of claim 11 to the mammal in need thereof, wherein the population of CD4+CD3+CD25+T cells having enhanced GPR15 expression and ability to migrate preferentially to the large intestine is administered to the mammal in need thereof, wherein the mammal in need thereof is afflicted with an inflammatory condition of the large intestine, thereby treating the mammal in need thereof.

14. A method for generating a population of T cells that migrates preferentially to the large intestine, the method comprising the steps of: isolating a population of T cells from a mammal and transfecting/transducing/transforming the population of T cells with a nucleic acid sequence encoding GPR15 to produce a population of T cells having enhanced GPR15 expression, wherein the enhanced GPR15 expression confers on the population of T cells an ability to migrate preferentially to the large intestine.

15. The method of claim 14, wherein the mammal is a human.

16. The method of claim 14, further comprising transfecting/transducing the population of T cells with nucleic acid sequences encoding integrin α4 and integrin β7 to confer enhanced expression of integrin α4β7 heterodimer to the T cell population.

17. The method of claim 14 or 16, wherein the population of T cells is isolated from whole blood or buffy coats of adults.

18. The method of claim 14 or 16, wherein the population of T cells is activated prior to the transfecting/transducing/transforming step.

19. The method of claim 18, wherein the population of T cells is activated using anti-CD3/CD28 activating agents.

20. The method of claim 14 or 16, wherein the population of T cells comprises CD4+CD3+CD25+T cells, CD4+CD3+CD25+CD127−T cells, CD4+CD3+CD25−T cells, or CD8+CD3+ T cells and the transfecting/transducing produces a population of CD4+CD3+CD25+T cells, CD4+CD3+CD25+CD127−T cells, CD4+CD3+ effector T cells, or CD8+CD3+ effector T cells, respectively, having enhanced GPR15 expression and ability to migrate preferentially to the large intestine.

21. The method of claim 20, further comprising administering to a mammal the population of CD4+CD3+CD25+T cells or CD4+CD3+CD25+CD127−T cells having enhanced GPR15 expression and ability to migrate preferentially to the large intestine, wherein the mammal is afflicted with an inflammatory condition of the large intestine.

22. The method of claim 21, wherein the inflammatory condition of the large intestine is inflammatory bowel disease, idiopathic colitis, or infectious colitis.

23. The method of claim 22, wherein the inflammatory bowel disease is Crohn's disease or ulcerative colitis.

24. The method of claim 20, further comprising administering to a mammal the population of CD4+CD3+ effector T cells or CD8+CD3+ effector T cells having enhanced GPR15 expression and ability to migrate preferentially to the large intestine, wherein the mammal is afflicted with a cancer or an infection of the large intestine.

25. The method of claim 24, wherein the cancer is colon cancer or a cancer that has metastasized to the large intestine.

26. The method of claim 24, wherein the infection is a bacterial or viral infection.

27. A method for generating a population of T cells that migrates preferentially to the large intestine, the method comprising the steps of: isolating a population of T cells from a mammal and introducing a nucleic acid sequence encoding GPR15 into the population of T cells to produce a population of T cells having enhanced GPR15 expression, wherein the enhanced GPR15 expression confers on the population of T cells an ability to migrate preferentially to the large intestine.

* * * * *